US007241779B2

(12) United States Patent
Hudkins et al.

(10) Patent No.: US 7,241,779 B2
(45) Date of Patent: Jul. 10, 2007

(54) FUSED PYRROLOCARBAZOLES

(75) Inventors: Robert L. Hudkins, Chester Springs, PA (US); Allison L. Zulli, Wayne, PA (US); Dandu R. Reddy, Downingtown, PA (US); Ming Tao, Maple Glen, PA (US); Theodore L. Underiner, Malvern, PA (US)

(73) Assignee: Cephalon, Inc., Frazer, PA (US)

( * ) Notice: Subject to any disclaimer, the term of this patent is extended or adjusted under 35 U.S.C. 154(b) by 71 days.

(21) Appl. No.: 11/017,915

(22) Filed: Dec. 22, 2004

(65) Prior Publication Data

US 2005/0137245 A1    Jun. 23, 2005

Related U.S. Application Data

(60) Provisional application No. 60/532,252, filed on Dec. 23, 2003.

(51) Int. Cl.
| | | |
|---|---|---|
| *A61K 31/403* | (2006.01) |
| *A61K 31/4427* | (2006.01) |
| *A61K 31/497* | (2006.01) |
| *A61K 31/5355* | (2006.01) |
| *A61K 31/416* | (2006.01) |
| *A61K 31/4162* | (2006.01) |
| *C07D 487/22* | (2006.01) |

(52) U.S. Cl. ............... 514/338; 514/410; 514/406; 514/274; 514/255.05; 514/232.8; 548/417; 548/358.1; 544/316; 544/405; 544/111; 546/275.7

(58) Field of Classification Search ............ 548/417, 548/358.1; 544/316, 274, 405, 111; 546/275.7; 514/410, 406, 274, 338, 232.8, 255.05
See application file for complete search history.

(56) References Cited

U.S. PATENT DOCUMENTS

| 5,475,110 | A | 12/1995 | Hudkins et al. | 546/256 |
|---|---|---|---|---|
| 5,591,855 | A | 1/1997 | Hudkins et al. | 546/256 |
| 5,594,009 | A | 1/1997 | Hudkins et al. | 514/338 |
| 5,616,724 | A | 4/1997 | Hudkins et al. | 548/417 |
| 5,705,511 | A | 1/1998 | Hudkins et al. | 514/338 |
| 6,630,500 | B2 | 10/2003 | Gingrich et al. | 514/410 |
| 2004/0048915 | A1* | 3/2004 | Engler et al. | 514/410 |
| 2005/0143442 | A1* | 6/2005 | Hudkins et al. | 514/406 |

FOREIGN PATENT DOCUMENTS

| WO | WO 96/11933 | A1 | 4/1996 |
|---|---|---|---|
| WO | WO 98/07433 | A1 | 2/1998 |
| WO | WO 00/47583 | A1 | 8/2000 |
| WO | WO 02/17914 | A2 | 3/2002 |
| WO | WO 02/28861 | A2 | 4/2002 |
| WO | WO 02/28874 | A3 | 4/2002 |
| WO | WO 02/30942 | A3 | 4/2002 |
| WO | WO 02/092065 | A2 | 11/2002 |
| WO | 0 545 195 | A1 | 6/2003 |

OTHER PUBLICATIONS

Folkman, J. "Anti-Angiogenesis: New Concept for Therapy of Solid Tumors", Ann. Surg. vol. 175, No. 3, 1972.*
Angeles, et al., "Enzyme-linked immunosorbent assay for trkA tyrosine kinase activity," *Anal. Biochem.*, 1996, 236, 49-55.
Hudkins, R.L., et al., "Synthesis of benzo[b]furano-[2,3-a]pyrrolo[3,4-c]carbazole-5,-7-dione," *J. Heterocyclic Chemistry*, 2001, 38, 591-595.
Hudkins, R.L., "Synthesis of indeno[2,1-a]pyrrolo[3,4-c]carbzole lactam regioisomers using ethyl cis-β-cyanoacrylate as a dienophile and lactam precursor," *J. Heterocyclic Chemistry*, 2003, 40, 135-142.
*J. Chem. Res.*, 1986, 1401-1445.
Lehninger, A.L., "The amino acid building blocks of proteins," The Molecular Basis of Cell Structure and Function, *Biochemistry*, 2nd Ed. Worth Publishers, NY, 1975, 71-77.
Merritt, S.E., et al., "The mixed lineage kinase DLK utilizes MKK7 and not MKK4 as substrate," *J. Biol. Chem.*, 1999, 274(15), 10195-10202.
Peet, N., et al., "Synthesis of angular benzodipyrazoles and related systems," *Heterocycles*, 1991, 32(1), 41-72.
Pitt, A.M., et al., "High throughput screening protein kinase assays optimized for reaction, binding, and detection totally within a 96-well plate," *J. of Biomol. Screening*, 1996, 1(1), 47-51.
Rotin, et al., "SH2 domains prevent tyrosine dephosphorylation of the EGF receptor: identification of Tyr992 as the high-affinity biding site for SH2 domains of phospholipase C-γ," *EMBO J.*, 1992, 11(2), 559-567.
Rovin, L.J., "Preformulation," *Remington's Pharmaceutical Sciences*, 17th Ed., Mack Publishing Co., Easton, PA, 1985, Chapter 76, 1409-1423.
Schenone, P., et al., "Reaction of 2-dimethylaminomethylene-1,3-diones with dinucleophiles. I. Synthesis of 1,5-disubstituted 4-acylpyrazoles," *J. Heterocyclic Chem.*, 1982, 19, 1355-1361.
Wynne, J.H., et al., "Facile one-pot synthesis of S-alkyl thiocarbamates," *J. Org. Chem.*, 2003, 68, 3733-3735.
Engler, T.A., et al., "Novel, potent and selective cynclin D1/CDK4 inhibitors: indolo[6,7-a]pyrrolo[3,4-c]carbazoles," *Bioorganic & Medicinal Chem. Letts.*, 2003, 13:2261-2267.
Gingrich, D.E., et al., "A new class of potent vascular endothelial growth factor receptor tyrosine kinase inhibitors: structure-activity relationships for a series of 9-alkoxymethyl-12-(3-hydroxypropyl)indeno[2,1-a]pyrrolo[3,4-c]carbazole-5-ones and the identification of CEP-5214 and its dimethylglycine ester prodrug clinical candidate CEP-7055," *J. Med. Chem.*, 2003, 46, 5375-5388, Dec. 18, 2003.
Laird, A.D., et al., "Small molecule tyrosine kinase inhibitors: clinical development of anticancer agents," *Expert. Opin. Investig. Drugs*, 2003, 12(1), 51-64, Jan. 2003.

(Continued)

Primary Examiner—Joseph K. McKane
Assistant Examiner—Michael Barker
(74) Attorney, Agent, or Firm—Woodcock Washburn LLP

(57) ABSTRACT

The present invention relates generally to selected fused pyrrolocarbazoles, including pharmaceutical compositions thereof and methods of treating diseases therewith. The present invention is also directed to intermediates and processes for making these fused pyrrolocarbazoles.

21 Claims, No Drawings

OTHER PUBLICATIONS

Ruggeri, B., et al., "CEP-7055: A novel, orally active pan inhibitor of vascular endothelial growth factor receptor tyrosine kinases with potent antiangiogenic activity and antitumor efficacy in preclinical models," *Cancer Res.*, 2003, 63, 5978-5991, Sep. 15, 2003.

Sanchez-Martinez, C., et al., "Aryl[a]pyrrolo[3,4-*c*]carbazoles as selective cyclin D1-CDK4 inhibitors," *Bioorganic & Medicinal Chem. Letts.*, 2003, 13, 3835-3839.

\* cited by examiner

FUSED PYRROLOCARBAZOLES

CROSS-REFERENCE TO RELATED APPLICATIONS

This application claims priority of U.S. Provisional Application No. 60/532,252, filed Dec. 23, 2003, which is incorporated herein by reference in its entirety for all purposes.

FIELD OF THE INVENTION

The present invention relates generally to fused pyrrolocarbazoles, including pharmaceutical compositions, diagnostic kits, assay standards or reagents containing the same, and methods of using the same as therapeutics. The invention is also directed to intermediates and processes for making these novel compounds.

BACKGROUND OF THE INVENTION

Publications cited throughout this disclosure are incorporated in their entirety herein by reference.

Various synthetic small organic molecules that are biologically active and generally known in the art as "fused pyrrolocarbazoles" have been prepared (See U.S. Pat. Nos. 5,475,110; 5,591,855; 5,594,009; 5,616,724; and 6,630,500). In addition, U.S. Pat. No. 5,705,511 discloses fused pyrrolocarbazole compounds which possess a variety of functional pharmacological activities. The fused pyrrolocarbazoles were disclosed to be used in a variety of ways, including: enhancing the function and/or survival of cells of neuronal lineage, either singularly or in combination with neurotrophic factor(s) and/or indolocarbazoles; enhancing trophic factor-induced activity; inhibition of protein kinase C ("PKC") activity; inhibition of trk tyrosine kinase activity; inhibition of proliferation of a prostate cancer cell-line; inhibition of the cellular pathways involved in the inflammation process; and enhancement of the survival of neuronal cells at risk of dying. However, there remains a need for novel pyrrolocarbazole derivatives that possess beneficial properties. This invention is directed to this, as well as other important ends.

SUMMARY OF THE INVENTION

The present invention in one aspect is directed to fused pyrrolocarbazole compounds of Formula I:

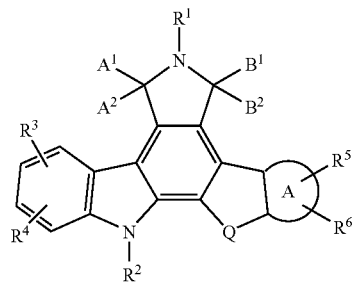

and its stereoisomeric forms, mixtures of stereoisomeric forms, or pharmaceutically acceptable salt forms thereof, wherein the constituent members are defined infra.

The fused pyrrolocarbazoles of the present invention may be used in a variety of ways, including: for inhibition of angiogenesis; as antitumor agents; for enhancing the function and/or survival of cells of neuronal lineage, either singularly or in combination with neurotrophic factor(s) and/or indolocarbazoles; for enhancing trophic factor-induced activity; inhibition of kinase activity, such as trk tyrosine kinase ("trk"), vascular endothelial growth factor receptor ("VEGFR") kinase, preferably VEGFR1 and VEGFR2, mixed lineage kinase ("MLK"), dual leucine zipper bearing kinase ("DLK"), platelet derived growth factor receptor kinase ("PDGFR"), protein kinase C ("PKC"), Tie-2, or CDK-1, -2, -3, -4, -5, -6; for inhibition of NGF-stimulated trk phosphorylation; for inhibition of proliferation of a prostate cancer cell-line; for inhibition of the cellular pathways involved in the inflammation process; and for enhancement of the survival of neuronal cells at risk of dying. In addition, the fused pyrrolocarbazoles may useful for inhibition of c-met, c-kit, and mutated Flt-3 containing internal tandem duplications in the juxtamembrane domain. Because of these varied activities, the disclosed compounds find utility in a variety of settings, including research and therapeutic environments.

In other embodiments, the compounds of the present invention are useful for treating or preventing angiogenesis and angiogenic disorders such as cancer of solid tumors, endometriosis, retinopathy, diabetic retinopathy, psoriasis, hemangioblastoma, ocular disorders or macular degeneration. In another embodiment, the compounds of the present invention are useful for treating or preventing neoplasia, rheumatoid arthritis, chronic arthritis, pulmonary fibrosis, myelofibrosis, abnormal wound healing, atherosclerosis, or restenosis. In further embodiments, the compounds of the present invention are useful for treating or preventing neurodegenerative diseases and disorders, such as Alzheimer's disease, amyotrophic lateral sclerosis, Parkinson's disease, stroke, ischemia, Huntington's disease, AIDS dementia, epilepsy, multiple sclerosis, peripheral neuropathy, chemotherapy induced peripheral neuropathy, AIDS related peripheral neuropathy, or injuries of the brain or spinal chord. In additional embodiments, the compounds of the present invention are useful for treating or preventing prostate disorders such as prostate cancer or benign prostate hyperplasia. In still other embodiments, the compounds of the present invention are useful for treating or preventing multiple myeloma and leukemias including, but not limited to, acute myelogenous leukemia, chronic myelogenous leukemia, acute lymphocytic leukemia, and chronic lymphocytic leukemia.

In further aspect, the present invention is directed to pharmaceutical compositions which comprises one or more pharmaceutically acceptable excipients and a therapeutically effective amount of a compound of the present invention.

DETAILED DESCRIPTION

Thus, in a first embodiment, the present invention provides a novel compound of Formula I:

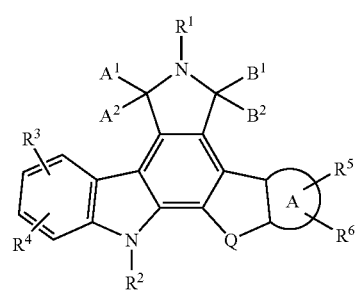

wherein:

ring A together with the carbon atoms to which it is attached, is selected from:
(a) a phenylene ring in which from 1 to 3 carbon atoms may be replaced by nitrogen atoms; and
(b) a 5-membered aromatic ring in which from 1 to 2 carbon atoms may be replaced by nitrogen atoms;

$A^1$ and $A^2$ are independently selected from H, H; and a group wherein $A^1$ and $A^2$ together form a moiety selected from =O;

$B^1$ and $B^2$ are independently selected from H, H; and a group wherein $B^1$ and $B^2$ together form a moiety selected from =O;

provided that at least one of the pairs $A^1$ and $A^2$, or $B^1$ and $B^2$ forms =O;

$R^1$ is H or optionally substituted alkyl, wherein said optional substituents are one to three $R^{10}$ groups;

$R^2$ is selected from H, C(=O)$R^{2a}$, C(=O)N$R^2R^{2d}$, SO$_2R^{2b}$, CO$_2R^{2b}$, optionally substituted alkyl, optionally substituted alkenyl, optionally substituted alkynyl, optionally substituted cycloalkyl, and optionally substituted heterocycloalkyl, wherein said optional substituents are one to three $R^{10}$ groups;

$R^{2a}$ is selected from optionally substituted alkyl, optionally substituted aryl, OR$^{2b}$, NR$^{2c}R^{2d}$, (CH$_2$)$_p$NR$^{2c}R^{2d}$, and O(CH$_2$)$_p$NR$^{2c}R^{2d}$, wherein said optional substituents are one to three $R^{10}$ groups;

$R^{2b}$ is selected from H and optionally substituted alkyl, wherein said optional substituents are one to three $R^{10}$ groups;

$R^{2c}$ and $R^{2d}$ are each independently selected from H and optionally substituted alkyl, or together with the nitrogen to which they are attached form an optionally substituted heterocycloalkyl, wherein said optional substituents are one to three $R^{10}$ groups;

at least one of $R^3$, $R^4$, $R^5$, and $R^6$ is selected from OR$^{14}$; C(=O)R$^{22}$; CH=NR$^{26}$; NR$^{11}$C(=O)R$^{20}$; NR$^{11}$C(=O)OR$^{15}$; OC(=O)R$^{20}$; OC(=O)NR$^{11}R^{21}$; O-(alkylene)-R$^{24}$; $Z^1$-(alkylene)-R$^{23}$, wherein $Z^1$ is selected from CO$_2$, O$_2$C, C(=O), NR$^{11}$, NR$^{11}$C(=O), and NR$^{11}$C(=O)O; and (alkylene)-$Z^2$-(alkylene)-R$^{23}$, wherein $Z^2$ is selected from O, S(O)$_y$, C(=O)NR$^{11}$, NR$^{11}$C(=O), NR$^{11}$C(=O)NR$^{11}$, OC(=O)NR$^{11}$, NR$^{11}$C(=O)O;
wherein said alkylene groups are optionally substituted with one to three $R^{10}$ groups;

the other $R^3$, $R^4$, $R^5$, or $R^6$ moieties can be selected independently from H, $R^{10}$, optionally substituted alkyl, optionally substituted alkenyl, and optionally substituted alkynyl, wherein said optional substituents are one to three $R^{10}$ groups;

Q is selected from an optionally substituted $C_{1-2}$ alkylene, wherein said optional substituents are one to three $R^{10}$ groups;

$R^{10}$ is selected from alkyl, cycloalkyl, spirocycloalkyl, aryl, heteroaryl, heterocycloalkyl, arylalkoxy, F, Cl, Br, I, CN, CF$_3$, NR$^{27A}R^{27B}$, NO$_2$, OR$^{25}$, OCF$_3$, =O, =NR$^{25}$, =N—OR$^{25}$, =N—N(R$^{25}$)$_2$, OC(=O)R$^{25}$, OC(=O)NHR$^{11}$, O—Si(R$^{16}$)$_4$, O-tetrahydropyranyl, ethylene oxide, NR$^{16}$C(=O)R$^{25}$, NR$^{16}$CO$_2R^{25}$, NR$^{16}$C(=O)NR$^{27A}R^{27B}$, NHC(=NH)NH$_2$, NR$^{16}$S(O)$_2R^{25}$, S(O)$_yR^{25}$, CO$_2R^{25}$, C(=O)N$^{27R}R^{27B}$, C(=O)R$^{25}$, CH$_2$OR$^{25}$, (CH$_2$)$_p$OR$^{25}$, CH=NNR$^{27A}R^{27B}$, CH=NOR$^{25}$, CH=NR$^{25}$, CH=NNHCH(N=NH)NH$_2$, S(=O)$_2$NR$^{27A}R^{27B}$, P(=O)(OR$^{25}$)$_2$, OR$^{13}$, and a monosaccharide wherein each hydroxyl group of the monosaccharide is independently either unsubstituted or is replaced by H, alkyl, alkylcarbonyloxy, or alkoxy;

$R^{11}$ is selected from H and optionally substituted alkyl, wherein said optional substituents are one to three $R^{10}$ groups;

$R^{12}$ is selected from optionally substituted alkyl, optionally substituted aryl, and optionally substituted heteroaryl, wherein said optional substituents are one to three $R^{10}$ groups;

$R^{13}$ is the residue of an amino acid after the removal of the hydroxyl moiety from the carboxyl group thereof;

$R^{14}$ is optionally substituted heteroaryl, wherein said optional substituents is one to three $R^{10}$ groups;

$R^{15}$ is optionally substituted alkyl, wherein said optional substituents is one to three $R^{10}$ groups;

$R^{16}$ is H or alkyl;

$R^{17}$ is selected from optionally substituted alkyl, optionally substituted aryl, optionally substituted heteroaryl, optionally substituted cycloalkyl, and optionally substituted heterocycloalkyl, wherein said optional substituents are one to three $R^{10}$ groups;

$R^{18}$ is selected from H, optionally substituted alkyl, optionally substituted aryl, optionally substituted heteroaryl, optionally substituted cycloalkyl, and optionally substituted heterocycloalkyl, wherein said optional substituents are one to three $R^{10}$ groups;

$R^{19}$ is selected from optionally substituted cycloalkyl, optionally substituted heterocycloalkyl, and optionally substituted heteroaryl, wherein said optional substituents are one to three $R^{10}$ groups;

$R^{20}$ is selected from optionally substituted aryl, optionally substituted heteroaryl, optionally substituted cycloalkyl, and optionally substituted heterocycloalkyl, wherein said optional substituents are one to three $R^{10}$ groups;

$R^{21}$ is selected from H, optionally substituted alkyl, optionally substituted alkenyl, optionally substituted alkynyl, optionally substituted aryl, optionally substituted arylalkyl, optionally substituted heteroaryl, optionally substituted cycloalkyl, and optionally substituted heterocycloalkyl, wherein said optional substituents are one to three $R^{10}$ groups;

$R^{22}$ is selected from optionally substituted aryl, and optionally substituted heteroaryl, wherein said optional substituents are one to three $R^{10}$ groups;

$R^{23}$ is selected from optionally substituted alkenyl, optionally substituted alkynyl, optionally substituted aryl, optionally substituted heteroaryl, optionally substituted cycloalkyl, optionally substituted heterocycloalkyl, OR$^{21}$, O(CH$_2$)$_p$OR$^{21}$, (CH$_2$)$_p$OR$^{21}$, SR$^{18}$, SOR$^{17}$, SO$_2R^{18}$, CN, N(R$^{20}$)$_2$, CHOH(CH$_2$)$_p$N(R$^{11}$)$_2$, C(=O)N(R$^{18}$)$_2$, NR$^{18}$C(=O)R$^{18}$, NR$^{18}$C(=O)N(R$^{18}$)$_2$, C(=NR$^{18}$)OR$^{18}$, C(R$^{12}$)=NOR$^{18}$, NHOR$^{21}$, NR$^{18}$C(=NR$^{18}$)N(R$^{18}$)$_2$, NHCN, CONR$^{18}$OR$^{18}$, CO$_2R^{18}$, OCOR$^{17}$, OC(=O)N(R$^{18}$)$_2$, NR$^{18}$C(=O)OR$^{17}$, and C(=O)R$^{18}$, wherein said optional substituents are one to three $R^{10}$ groups;

$R^{24}$ is selected from optionally substituted alkenyl, optionally substituted aryl, optionally substituted heteroaryl, optionally substituted cycloalkyl, optionally substituted heterocycloalkyl, CN, OR$^{21}$, O(CH$_2$)$_p$OR$^{21}$, (CH$_2$)$_p$OR$^{21}$, SR$^{19}$, SOR$^{17}$, SO$_2R^{18}$, N(R$^{18}$)$_2$, CHOH(CH$_2$)$_p$N(R$^{11}$)$_2$, NR$^{18}$C(=O)R$^{18}$, NR$^{18}$C(=O)N(R$^{18}$)$_2$, C(=NR$^{18}$)OR$^{18}$, NHOR$^{21}$, NR$^{18}$C(=NR$^{18}$)N(R$^{18}$)$_2$, NHCN, C(=O)N(R$^{18}$)$_2$, C(=O)NR$^{27A}R^{27B}$, C(=O)NR$^{11}R^{28}$, C(=O)NR$^{18}$OR$^{18}$, C(=O)NR$^{11}$N(R$^{11}$)$_2$, C(=O)NR$^{11}$(alkylene)NR$^{27A}R^{27B}$, CO$_2R^{18}$, OCOR$^{17}$, OC(=O)N(R$^{18}$)$_2$, NR$^{18}$C(=O)OR$^{17}$, C(=O)NR$^{11}R^{18}$ and C(=O)R$^{18}$, wherein said optional substituents are one to three $R^{10}$ groups;

$R^{25}$ is H, alkyl, aryl, heteroaryl, cycloalkyl, or heterocycloalkyl;

$R^{26}$ is selected from optionally substituted cycloalkyl and optionally substituted heterocycloalkyl, wherein said optional substituents are one to three $R^{10}$ groups;

$R^{27A}$ and $R^{27B}$ are each independently selected from H and alkyl, or together with the nitrogen to which they are attached form an optionally substituted heterocycloalkyl, wherein said optional substituents are selected from alkyl, aryl and heteroaryl;

$R^{28}$ is optionally substituted arylalkyl, wherein said optional substituent is one to three $R^{10}$ groups;

p is independently selected from 1, 2, 3, and 4;

y is independently selected from 0, 1 and 2; and a stereoisomer or a pharmaceutically acceptable salt form thereof.

In another embodiment, the compounds of Formula I as defined herein are not intended to include any compounds disclosed in PCT Publ. No. WO 98/07433. In particular, when $A^1, A^2$ is =O; $B^1$, $B^2$ are independently H or OH, or $B^1$, $B^2$ combine to form =O; rings A and B are each phenylene; Q is CH—$R^a$; and one of $R^2$ or $R^a$ is H and the other is optionally substituted

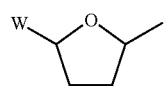 or 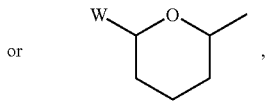

wherein W is optionally substituted $C_1$ alkyl, or $NR^{27A}R^{27B}$; then any of $R^3$, $R^4$, $R^5$, and $R^6$ cannot include $OR^{14}$ or O-(alkylene)-$R^{24}$.

Other aspects of the present invention include the compounds of Formula I as defined herein wherein ring A is phenylene; or a 5-membered aromatic ring containing one nitrogen atom, preferably pyrazolylene, and more preferably

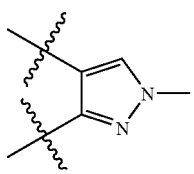 or 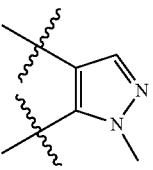

Further aspects include those compounds wherein $R^1$ is H or optionally substituted alkyl. Another aspect includes those compounds wherein $R^2$ is H, C(=O)$R^{2a}$, C(=O)NR$^{2c}$CR$^{2d}$, SO$_2$R$^{2b}$, CO$_2$R$^{2b}$, optionally substituted alkyl, optionally substituted alkenyl, optionally substituted alkynyl, or optionally substituted cycloalkyl, and preferably H, optionally substituted alkyl, optionally substituted alkenyl, optionally substituted alkynyl, or optionally substituted cycloalkyl, and more preferably $R^2$ is H or optionally substituted alkyl. Additional aspects include those compounds wherein groups $A^1A^2$ are H, H; and $B^1B^2$ together form =O. In yet another aspect, the invention includes compounds wherein Q is selected from an optionally substituted $C_{1-2}$ alkylene, or preferably Q is CH$_2$, or CH$_2$CH$_2$. Further aspects include those compounds wherein $R^{14}$ is benzoxazole, benzothiazole, pyrimidine, pyrazine or triazine; $R^{22}$ is a 5-membered heteroaryl group; $R^{20}$ is heterocycloalkyl or heteroaryl; $R^{23}$ is heteroaryl or heterocycloalkyl; $R^{24}$ is heteroaryl; and $R^{26}$ is heterocycloalkyl. Additional aspects of the present invention include any combination of the above preferred substituents, such as, for example, a compound of Formula I with the preferred moieties of groups $R^1$ and $R^2$; or $R^1$ and Q; or $R^1$, $R^2$; or Q; etc.

In another embodiment of the present invention, there are included compounds having a structure of Formula II:

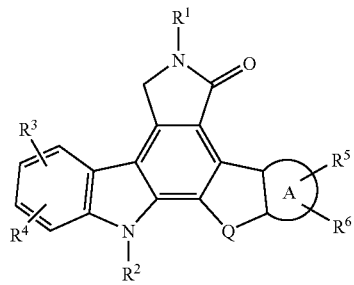

II

In one aspect, there are included compounds of Formula II wherein ring A is phenylene or pyrazolylene, preferably

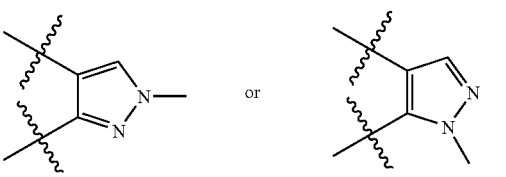

Another aspect includes those compounds wherein $R^1$ is H or optionally substituted alkyl. Further aspects include those compounds wherein $R^2$ is H, C(=O)$R^{2a}$, C(=O)NR$^{2c}$R$^{2d}$, SO$_2$R$^{2b}$, CO$_2$R$^{2b}$, optionally substituted alkyl, optionally substituted alkenyl, optionally substituted alkynyl, or optionally substituted cycloalkyl, and preferably H, optionally substituted alkyl, optionally substituted alkenyl, optionally substituted alkynyl, or optionally substituted cycloalkyl, and more preferably $R^2$ is H or optionally substituted alkyl. Additional aspects include compounds wherein Q is selected from an optionally substituted $C_{1-2}$ alkylene, or preferably Q is CH$_2$ or CH$_2$CH$_2$. Additional aspects of the present invention include any combination of the above preferred substituents, such as, for example, a compound of Formula II with the preferred moieties of groups $R^1$ and $R^2$; or $R^1$ and Q; or $R^1$, $R^2$; or Q; etc.

In yet another embodiment of the present invention, there are included compounds having a structure of Formula III:

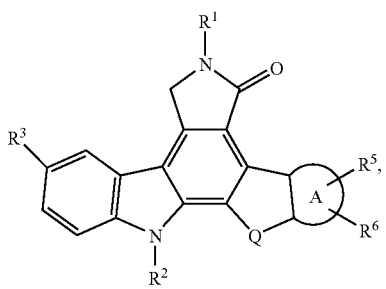

III where preferrably ring A is phenylene or pyrazolylene, preferably

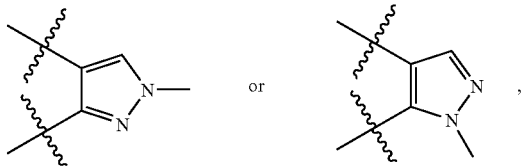

and $R^1$ is H or optionally substituted alkyl; and Formula IV:

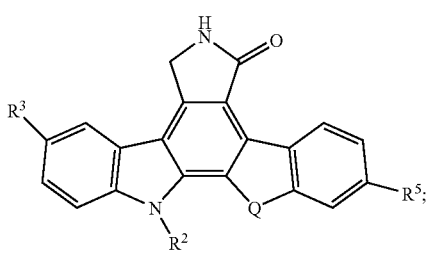

and Formula V:

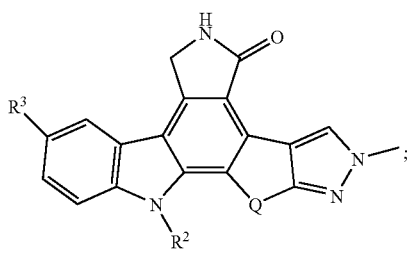

and Formula VI:

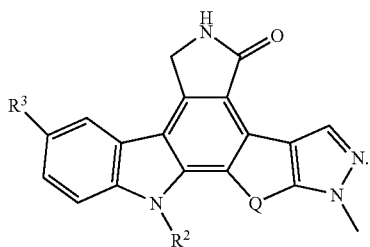

In certain aspects of the present invention, there are included compounds of Formulas III–VI wherein $R^2$ is H, $C(=O)R^{2a}$, $C(=O)NR^{2c}R^{2d}$, $SO_2R^{2b}$, $CO_2R^{2b}$, optionally substituted alkyl, optionally substituted alkenyl, optionally substituted alkynyl, or optionally substituted cycloalkyl, and preferably H, optionally substituted alkyl, optionally substituted alkenyl, optionally substituted alkynyl, or optionally substituted cycloalkyl, and more preferably $R^2$ is H or optionally substituted alkyl. Other aspects include those compounds wherein Q is selected from an optionally substituted $C_{1-2}$ alkylene, or preferably Q is $CH_2$ or $CH_2CH_2$. Additional aspects of the present invention include any combination of the above preferred substituents for each of Formulas III–VI.

The following paragraphs show additional aspects of the invention for at least one $R^3$, $R^4$, $R^5$, and $R^6$ for compounds of Formulas I–VI and their respective preferred embodiments described heretofore.

1. $OR^{14}$; paticularly those wherein $R^{14}$ is optionally substituted benzoxazole, optionally substituted benzothiazole, optionally substituted pyrimidine, optionally substituted pyrazine or optionally substituted triazine.
2. $C(=O)R^{22}$; paticularly those wherein $R^{22}$ is an optionally substituted 5-membered heteroaryl group.
3. $CH=NR^{26}$; paticularly those wherein $R^{26}$ is optionally substituted heterocycloalkyl.
4. $NR^{11}C(=O)R^{20}$; paticularly those wherein $R^{20}$ is optionally substituted heteroaryl.
5. $NR^{11}C(=O)OR^{15}$.
6. $OC(=O)R^{20}$; paticularly those wherein $R^{20}$ is optionally substituted heterocycloalkyl.
7. $OC(=O)NR^{11}R^{20}$; paticularly those wherein $R^{20}$ is optionally substituted cycloalkyl or optionally substituted heterocycloalkyl.
8. O-(alkylene)-$R^{24}$; paticularly those wherein $R^{24}$ is optionally substituted heterocycloalkyl
9. $Z^1$-(alkylene)-$R^{23}$, wherein $Z^1$ is selected from $CO_2$, $O_2C$, $C(=O)$, $NR^{11}$, $NR^{11}C(=O)$, and $NR^{11}C(=O)O$; paticularly those wherein $Z^1$ is $C(=O)$ or $NR^{11}$.
10. (alkylene)-$Z^2$-(alkylene)-$R^{23}$, wherein $Z^2$ is selected from O, $S(O)_y$, $C(=O)NR^{11}$, $NR^{11}C(=O)$, $NR^{11}C(=O)NR^{11}$, $OC(=O)NR^{11}$, $NR^{11}C(=O)O$; paticularly those wherein $Z^2$ is O, $C(=O)NR^{11}$, or $NR^{11}C(=O)$.

The preceding paragraphs may be combined to further define additional prefered embodiments of compounds of Formulas I–VI. For example, one such combination for $R^3$, $R^4$, $R^5$, or $R^6$ can include $OR^{14}$; $C(=O)R^{22}$; $NR^{11}C(=O)R^{20}$; $NR^{11}C(=O)OR^{15}$; $OC(=O)R^{20}$; or $OC(=O)NR^{11}R^{20}$.

Another such combination includes $OR^{14}$; $C(=O)R^{22}$; and $NR^{11}C(=O)OR^{15}$.

A third such combination includes $OR^{14}$, wherein $R^{14}$ is benzoxazole, benzothiazole, pyrimidine, pyrazine or triazine; $C(=O)R^{22}$, wherein $R^{22}$ is a 5-membered heteroaryl group; $NR^{11}C(=O)R^{20}$, wherein $R^{20}$ is heteroaryl; $NR^{11}C(=O)OR^{15}$; $OC(=O)R^{20}$, wherein $R^{20}$ is heterocycloalkyl; or $OC(=O)NR^{11}R^{20}$, wherein $R^{20}$ is cycloalkyl, wherein each $R^{14}$, $R^{22}$, and $R^{20}$ is optionally substituted as set forth above.

The following terms and expressions used herein have the indicated meanings.

In the formulas described and claimed herein, it is intended that when any symbol appears more than once in a particular formula or substituent, its meaning in each instance is independent of the other.

As used herein, the term "about" refers to a range of values from ±10% of a specified value. For example, the phrase "about 50 mg" includes ±10% of 50, or from 45 to 55 mg.

As used herein, a range of values in the form "x-y" or "x to y", or "x through y", include integers x, y, and the integers therebetween. For example, the phrases "1–6", or "1 to 6" or "1 through 6" are intended to include the integers 1, 2, 3, 4, 5, and 6. Preferred embodiments include each individual integer in the range, as well as any subcombination of integers. For example, preferred integers for "1–6" can include 1, 2, 3, 4, 5, 6, 1–2, 1–3, 1–4, 1–5, 2–3, 2–4, 2–5, 2–6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$–$C_4$ alkyl" refers to an alkyl radical containing from 1 to 4 carbon atoms.

As used herein, the term "alkenyl" refers to a straight chain, or branched hydrocarbon chains of 2 to 8 carbon atoms having at least one carbon-carbon double bond. A designation "$C_2$–$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkynyl" refers to a straight chain, or branched hydrocarbon chains of 2 to 8 carbon atoms having at least one carbon-carbon triple bond. A designation "$C_2$–$C_8$ alkynyl" refers to an alkynyl radical containing from 2 to 8 carbon atoms. Examples include ethynyl, propynyl, isopropynyl, 3,5-hexadiynyl, etc.

As used herein, the term "alkylene" refers to a branched or straight chained hydrocarbon of 1 to 8 carbon atoms, which is formed by the removal of two hydrogen atoms. A designation such as "$C_1$–$C_4$ alkylene" refers to an alkylene radical containing from 1 to 4 carbon atoms. Examples include methylene (—$CH_2$—), propylidene ($CH_3CH_2CH$=), 1,2-ethandiyl (—$CH_2CH_2$—), etc.

As used herein, the term "phenylene" refers to a phenyl group with an additional hydrogen atom removed, ie. a moiety with the structure of:

As used herein, the term "cycloalkyl" refers to a saturated or partially saturated mono- or bicyclic alkyl ring system containing 3 to 10 carbon atoms. A designation such as "$C_5$–$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include cyclopropyl, cyclobutyl, cyclopentyl, cyclohexyl, cyclohexenyl, cycloheptyl, cyclooctyl, etc.

As used herein, the term "spirocycloalkyl" refers to a cycloalkyl group bonded to a carbon chain or carbon ring moiety by a carbon atom common to the cycloalkyl group and the carbon chain or carbon ring moiety. For example, a $C_3$ alkyl group substituted with an R group wherein the R group is spirocycloalkyl containing 5 carbon atoms refers to:

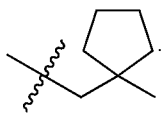

As used herein, the term "aryl" refers to a mono- or bicyclic hydrocarbon aromatic ring system having 6 to 12 ring carbon atoms. Examples include phenyl and naphthyl. Preferred aryl groups include phenyl or naphthyl groups. Included within the definition of "aryl" are fused ring systems, including, for example, ring systems in which an aromatic ring is fused to a cycloalkyl ring. Examples of such fused ring systems include, for example, indane and indene.

As used herein, the terms "heterocycle", "heterocyclic" or "heterocyclyl" refer to a mono- di-, tri- or other multicyclic aliphatic ring system that includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

Some heterocyclic groups containing one or more nitrogen atoms include pyrrolidine, pyrroline, pyrazoline, piperidine, morpholine, thiomorpholine, N-methylpiperazine, indole, isoindole, imidazole, imidazoline, oxazoline, oxazole, triazole, thiazoline, thiazole, isothiazole, thiadiazole, triazine, isoxazole, oxindole, pyrazole, pyrazolone, pyrimidine, pyrazine, quinoline, iosquinoline, and tetrazole groups. Some heterocyclic groups formed containing one or more oxygen atoms include furan, tetrahydrofuran, pyran, benzofurans, isobenzofurans, and tetrahydropyran groups. Some heterocyclic groups containing one or more sulfur atoms include thiophene, thianaphthene, tetrahydrothiophene, tetrahydrothiapyran, and benzothiophenes.

As used herein, the term "heterocycloalkyl" refers to a cycloalkyl group in which one or more ring carbon atoms are replaced by at least one hetero atom such as —O—, —N—, or —S—, and includes ring systems which contain a saturated ring group bridged or fused to one or more aromatic groups. Some heterocycloalkyl groups containing both saturated and aromatic rings include phthalamide, phthalic anhydride, indoline, isoindoline, tetrahydroisoquinoline, chroman, isochroman, and chromene.

As used herein, the term "heteroaryl" refers to an aryl group containing 5 to 10 ring carbon atoms in which one or more ring carbon atoms are replaced by at least one hetero atom such as —O—, —N—, or —S—. Some heteroaryl groups of the present invention include pyridyl, pyrimidyl, purinyl, pyrrolyl, pyridazinyl, pyrazinyl, triazinyl, imidazolyl, triazolyl, tetrazolyl, indolyl, isoindolyl, quinolyl, isoquinolyl, qunioxalinyl, quinazolinyl, cinnolinyl, phthalazinyl, benzoimidazolyl, pyrazolyl, thiazolyl, thiadiazolyl, isothiazolyl, oxazolyl, isoxazolyl, naphthyridinyl, oxindolyl, and benzothiazolyl groups.

As used herein, the term "arylalkyl" refers to an alkyl group that is substituted with an aryl group. Examples of arylalkyl groups include, but are not limited to, benzyl, phenethyl, benzhydryl, diphenylmethyl, triphenylmethyl, diphenylethyl, naphthylmethyl, etc.

As used herein, the term "arylalkoxy" refers to an aryl-substituted alkoxy group, such as benzyloxy, diphenylmethoxy, triphenylmethoxy, phenylethoxy, diphenylethoxy, etc.

As used herein, the term "monosaccharide" refers to a simple sugar of the formula $(CH_2O)_n$. The monosaccharides can be straight-chain or ring systems, and can include a saccharose unit of the formula —CH(OH)—C(=O)—. Examples of monosaccharides include erythrose, threose, ribose, arabinose, xylose, lyxose, allose, altrose, glucose, mannose, gulose, idose, galactose, talose, erythulose, ribulose, xyulose, psicose, fructose, sorbose, tagatose, erythropentulose, threopentulose, glycerotetrulose, glucopyranose, fructofuranose, etc.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-NH$_2$. The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. Biochemistry, 2$^{nd}$ ed.; Worth Publishers: New York, 1975; 71–77, the disclosure of which is incorporated herein by reference. Non-naturally occurring amino acids also include α-amino acids wherein the side chains are replaced with synthetic derivatives. In certain embodiments, substituent groups for the compounds of the present invention include the residue of an amino acid after removal of the hydroxyl moiety of the carboxyl group thereof; i.e., groups of formula —C(=O)CH(side chain)-NH$_2$. Representative side chains of naturally occurring and non-naturally occurring α-amino acids include are shown below in Table A.

As used herein, the term "trk" refers to the family of high affinity neurotrophin receptors presently comprising trk A, trk B, and trk C, and other membrane associated proteins to which a neurotrophin can bind.

As used herein, the term "VEGFR" refers to the family of high affinity vascular endothelial growth factor receptors presently comprising VEGFR1, VEGFR2, VEGFR3, and other membrane associated proteins to which a VEGF can bind.

As used herein, the term "MLK" refers to the family of high affinity mixed lineage kinases presently comprising MLK1, MLK2, MLK3, MLK4α & β, DLK, LZK, ZAK α & β, and other serine/threonine kinases classified within this family.

As used herein, the terms "enhance" or "enhancing" when used to modify the terms "function" or "survival" means that the presence of a compound of the present invention has a positive effect on the function and/or survival of a trophic factor responsive cell compared with a cell in the absence of the compound. For example, and not by way of limitation, with respect to the survival of, e.g., a cholinergic neuron, a compound of the present invention would evidence enhancement of survival of a cholinergic neuronal population at risk of dying (due to, e.g., injury, a disease condition, a degenerative condition or natural progression) when compared to a cholinergic neuronal population not presented with such a compound, if the treated population has a comparatively greater period of functionality than the non-treated population. As a further example, and again not by way of limitation, with respect to the function of, e.g., a sensory neuron, a compound of the present invention would evidence enhancement of the function (e.g. neurite extension)

TABLE A

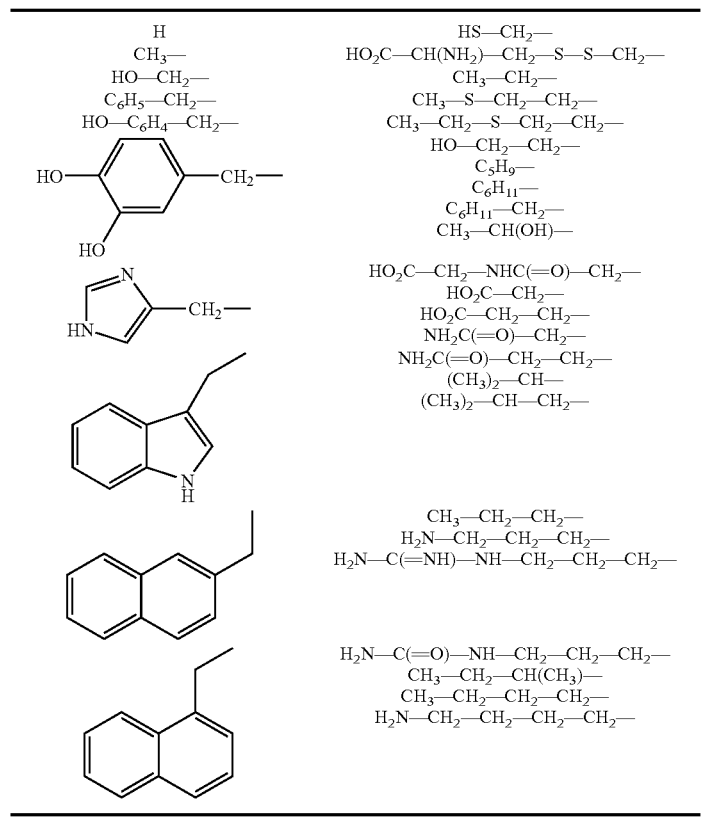

of a sensory neuronal population when compared to a sensory neuronal population not presented with such a compound, if the neurite extension of the treated population is comparatively greater than the neurite extension of the non-treated population.

As used herein, the terms "inhibit" or "inhibition" refer to a specified response of a designated material (e.g., enzymatic activity) is comparatively decreased in the presence of a compound of the present invention.

As used herein, the terms "cancer" or "cancerous" refer to any malignant proliferation of cells in a mammal. Examples include prostate, benign prostate hyperplasia, ovarian, breast, brain, lung, pancreatic, colorectal, gastric, stomach, solid tumors, head and neck, neuroblastoma, renal cell carcinoma, lymphoma, leukemia, other recognized malignancies of the hematopoietic systems, and other recognized cancers.

As used herein the terms "neuron", "cell of neuronal lineage" and "neuronal cell" refer to a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain and spinal cord neurons. As used herein, the phrase "sensory neuron" includes neurons responsive to environmental cues (e.g., temperature, movement) from, e.g., skin, muscle and joints; exemplary is a neuron from the DRG.

As used herein the term "trophic factor" refers to a molecule that directly or indirectly affects the survival or function of a trophic factor responsive cell. Exemplary trophic factors include Ciliary Neurotrophic Factor (CNTF), basic Fibroblast Growth Factor (bFGF), insulin and insulin-like growth factors (e.g., IGF-I, IGF-II, IGF-III), interferons, interleukins, cytokines, and the neurotrophins, including Nerve Growth Factor (NGF), Neurotrophin-3 (NT-3), Neurotrophin-4/5 (NT-4/5) and Brain Derived Neurotrophic Factor (BDNF).

As used herein the term "trophic factor-responsive cell" refers to a cell which includes a receptor to which a trophic factor can specifically bind; examples include neurons (e.g., cholinergic and sensory neurons) and non-neuronal cells (e.g., monocytes and neoplastic cells).

As used herein the terms "trophic factor activity" and "trophic factor-induced activity", refer to both endogenous and exogenous trophic factors, where "endogenous" refers to a trophic factor normally present and "exogenous" refers to a trophic factor added to a system. As defined, "trophic factor induced activity" includes activity induced by (1) endogenous trophic factors; (2) exogenous trophic factors; and (3) a combination of endogenous and exogenous trophic factors.

As used herein, the term "at risk of dying" in conjunction with a biological material, e.g., a cell such as a neuron, refers to a state or condition which negatively impacts the biological material such that the material has an increased likelihood of dying due to such state or condition. For example, compounds disclosed herein can "rescue" or enhance the survival of motoneurons which are naturally at risk of dying in an in ovo model of programmed cell death. Similarly, for example, a neuron may be at risk of dying due to the natural aging process which occasions the death of a neuron, or due to an injury, such as a trauma to the head, which may be such that neurons and/or glia, for example, impacted by such trauma may be at risk of dying. Further, for example, a neuron may be at risk of dying due to a disease state or condition, as in the case of neurons at risk of dying as occasioned by the disease ALS. Thus, by enhancing the survival of a cell at risk of dying by use of a compound of the claimed invention is meant that such compound decreases or prevents the risk of the death of the cell.

As used herein the term "contacting" refers to directly or indirectly causing placement together of moieties, such that the moieties directly or indirectly come into physical association with each other, whereby a desired outcome is achieved. Thus, as used herein, one can "contact" a target cell with a compound as disclosed herein even though the compound and cell do not necessarily physically join together (as, for example, is the case where a ligand and a receptor physically join together), as long as the desired outcome is achieved (e.g., enhancement of the survival of the cell). Contacting thus includes acts such as placing moieties together in a container (e.g., adding a compound as disclosed herein to a container comprising cells for in vitro studies) as well as administration of the compound to a target entity (e.g., injecting a compound as disclosed herein into a laboratory animal for in vivo testing, or into a human for therapy or treatment purposes).

As used herein, a "therapeutically effective amount" refers to an amount of a compound of the present invention effective to prevent or treat the symptoms of a particular disorder.

As used herein, the term "subject" refers to a warm blooded animal such as a mammal, preferably a human, or a human child, which is afflicted with, or has the potential to be afflicted with one or more diseases and conditions described herein.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

As used herein, "prodrug" is intended to include any covalently bonded carriers which release the active parent compound as defined in the present invention in vivo when such prodrug is administered to a mammalian subject. Since prodrugs are known to enhance numerous desirable qualities of pharmaceuticals (e.g., solubility, bioavailability, manufacturing, etc.) the compounds of the present invention may be delivered in prodrug form. Thus, the present invention contemplates prodrugs of the claimed compounds, compositions containing the same, and methods of delivering the same. Prodrugs of a compound of the present invention may be prepared by modifying functional groups present in the compound in such a way that the modifications are cleaved, either in routine manipulation or in vivo, to the parent compound. Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

It is recognized that compounds of the present invention may exist in various stereoisomeric forms. As such, the compounds of the present invention include their respective diastereomers or enantiomers. The compounds are normally prepared as racemates and can conveniently be used as such, but individual diastereomers or enantiomers can be isolated or synthesized by conventional techniques if so desired. Such racemates and individual diastereomers or enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: N.Y., 1994, and Jacques, J, et al. *Enantiomers, Racemates, and Resolutions*; Wiley: N.Y., 1981, each incorporated by reference herein in their entireties.

It is further recognized that functional groups present on the compounds of the present invention may contain protecting groups. For example, the amino acid side chain substituents of the compounds of the present invention can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl, and methoxybenzyl groups. Preferred groups for protecting hydroxy groups include TBS, acyl, benzyl ("Bn"), benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

Synthesis

The general routes to prepare the examples shown in Tables 1–3 of the present invention are shown in the Schemes 1–4. The intermediates used to prepare the examples and their mass spectral data are shown in the Table B. The reagents and starting materials are commercially available, or readily synthesized by well-known techniques by one of ordinary skill in the arts. All processes disclosed in association with the present invention are contemplated to be practiced on any scale, including milligram, gram, multigram, kilogram, multikilogram or commercial industrial scale. All substituents in the synthetic schemes, unless otherwise indicated, are as previously defined.

TABLE B

I-14
399
(M + 1)

I-18
383 (M − 1)

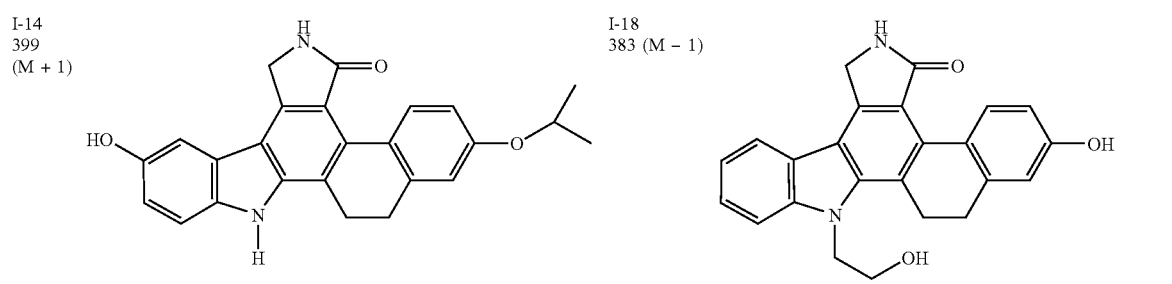

TABLE B-continued
I-19
339
(M − 1)
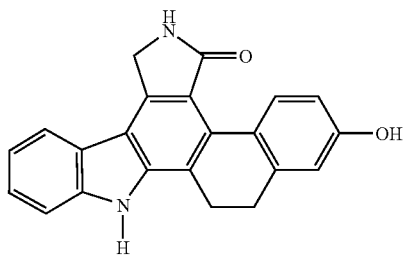
I-22
504 (M + 1)
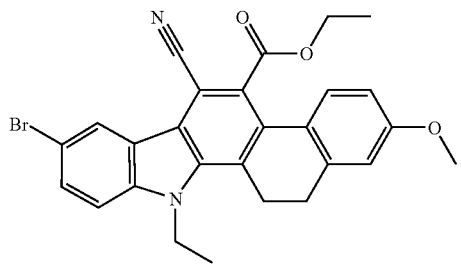
I-23
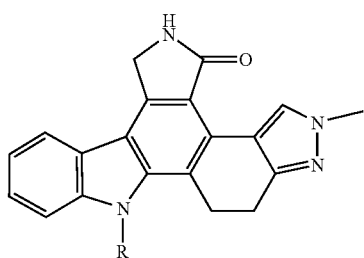
I-29
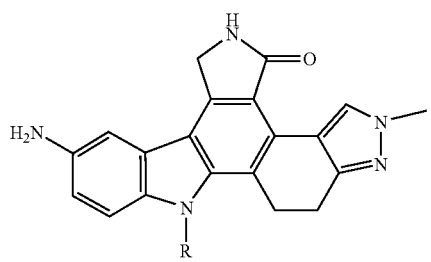
| | R |
|---|---|
| 357 (M + 1) | 23-1: Ethyl |
| 371 (M + 1) | 23-2: nPropyl |
| 385 (M + 1) | 23-3: i-butyl |
| 369 (M + 1) | 23-4: allyl |
| 426 (M + 1) | 23-5: CH$_2$CH$_2$NC$_4$H$_8$ |
| 400 (M + 1) | 23-6: CH$_2$CH$_2$NMe$_2$ |
| 482 (M + 1) | 23-7: (CH$_2$)$_6$NC$_4$H$_8$ |
| | R |
|---|---|
| 386 (M + 1) | 29-1: i-Propyl |
| 386 (M + 1) | 29-2: nPropyl |
| 400 (M + 1) | 29-3: i-Butyl |
| 400 (M + 1) | 29-4: nButyl |
I-33
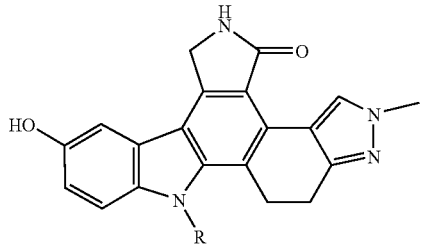
I-36
385 (M + 1)
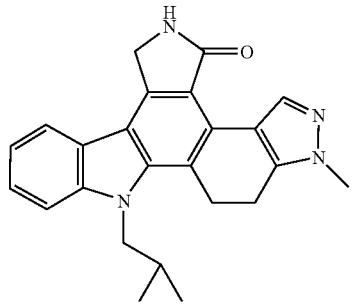
| | R |
|---|---|
| 373 (M + 1) | 33-1: Ethyl |
| 401 (M + 1) | 33-2: i-Butyl |
| 387 (M + 1) | 33-3: i-Propyl |
| 387 (M + 1) | 33-4: Propyl |

TABLE B-continued

I-39
401
(M + 1)

I-41
399 (M + 1)

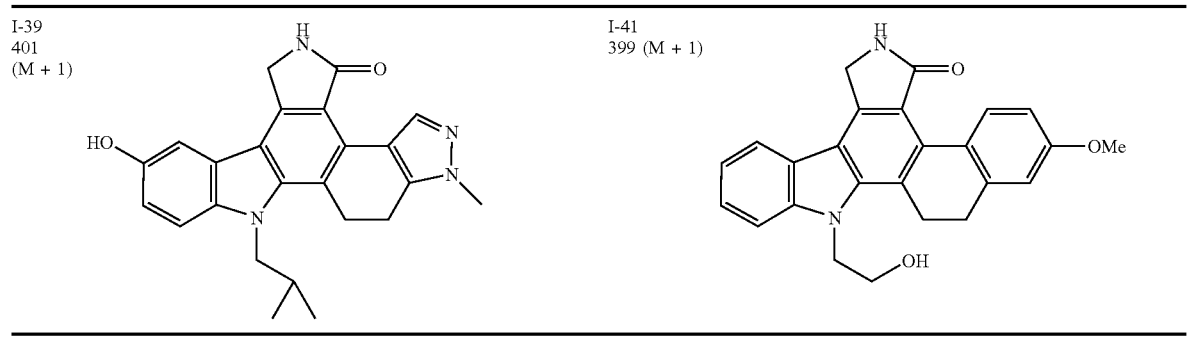

The general procedures to prepare the pyrrolocarbazoles of the present invention are described in U.S. Pat. No. 5,705,511 ("the '511 patent") and U.S. Pat. No. 6,630,500, PCT Publ. No. WO 00/47583, *J. Heterocyclic Chemistry*, 2001, 38, 591, and *J. Heterocyclic Chemistry*, 2003, 40, 135. In general, the lactam nitrogen or intermediate alcohol groups of the intermediates outlined in Table B may be protected with such groups as acetyl, substituted silyl, benzyl, Boc, or dimethoxybenzhydrol.

Intermediate I-23 (wherein R is hydrogen) used to prepare examples in Table 2, was prepared from the β-ketone, 2-methyl-1,4,6,7-tetrahydro-5H-indazol-5-one (Peet, N. P.; LeTourneau, M. E.; *Heterocycles*, 1991, 32, 41) using methods described in the '511 patent and in *J. Heterocyclic Chemistry*, 2003, 40, 135.

Scheme 1.

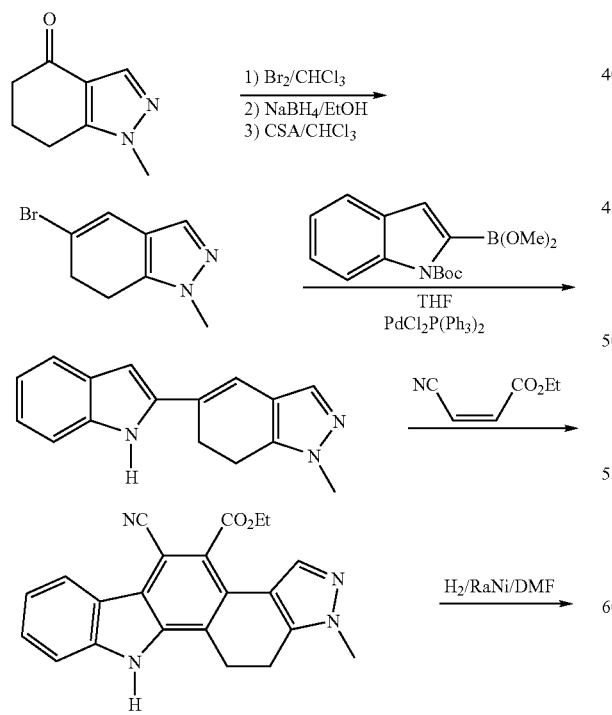

-continued

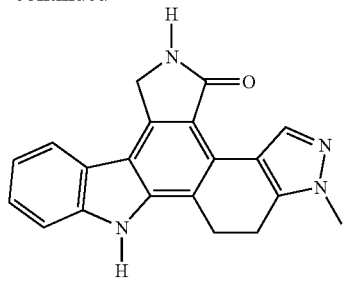

As shown in Scheme 1, the N1-methyl pyrazole derivatives in Table 3 were prepared from the 1-methyl α-ketone (*J. Chem. Res.*, 1986, 1401). The N2-methyl pyrazole intermediates were prepared according to procedures in *J. Heterocyclic Chem.* 1992, 19, 1355.

Scheme 2.

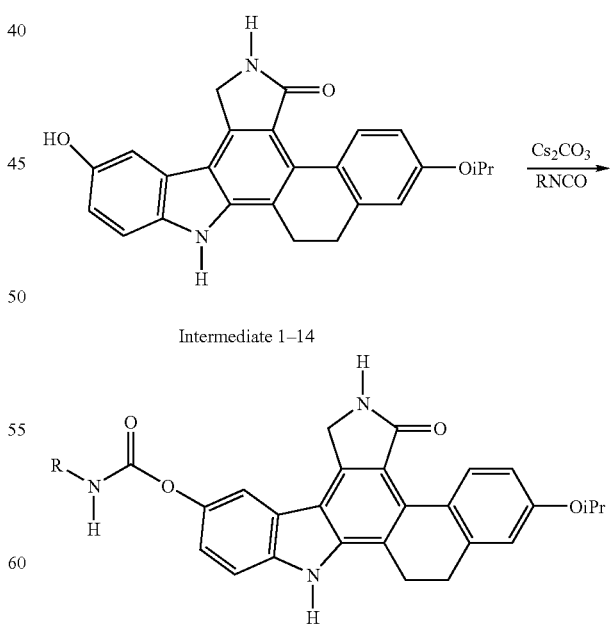

Intermediate 1–14

Examples 1–2, 70–72

-continued

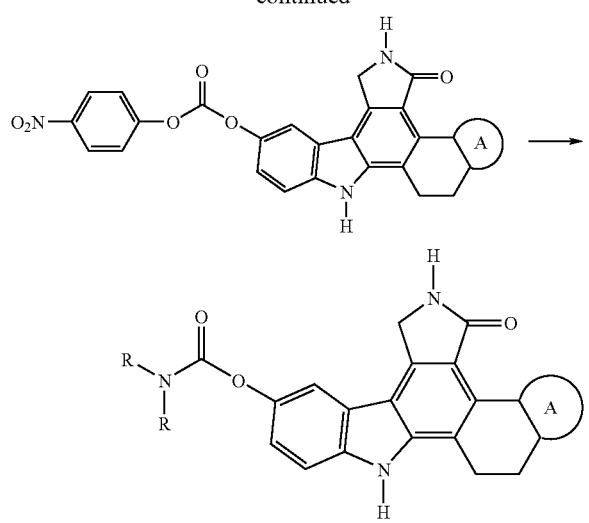

Scheme 2 outlines the route to prepare carbamate-type derivatives, such as Examples 1–2, and 70–72. An alternate method to preparing N,N-di-substituted carbamates utilized a nitrophenyl carbonate intermediate which may be treated with various primary or secondary amines. Similarly urea, O-carbamate, and N-carbamate derivatives may be prepared from reaction of the appropriate amine or phenol intermediate with an isocyanate or chloroformate or from the appropriate nitrophenyl carbonate, nitrophenyl carbamate, or trichloromethylcarbonyl (see *J. Org. Chem.* 2003, 68, 3733–3735).

Scheme 3.

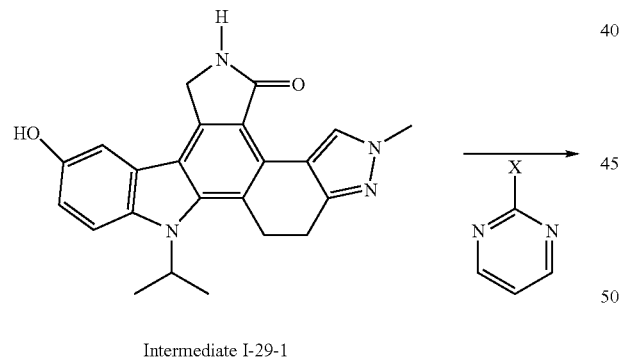

Intermediate I-29-1

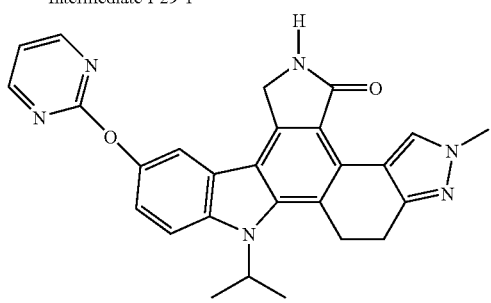

Example 19

Scheme 3 outlines a route to prepare heteroaryl ethers from the corresponding phenol using a base such as sodium hydride and a heteroaryl bromide or chloride.

Scheme 4.

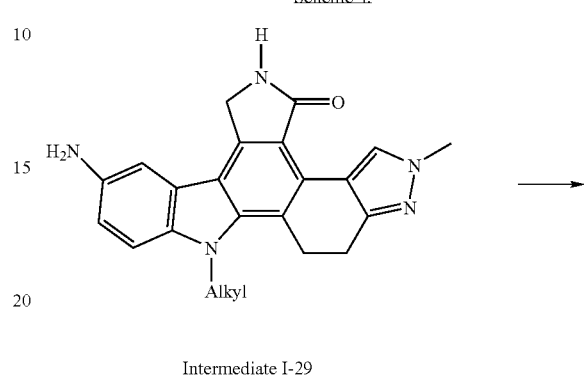

Intermediate I-29

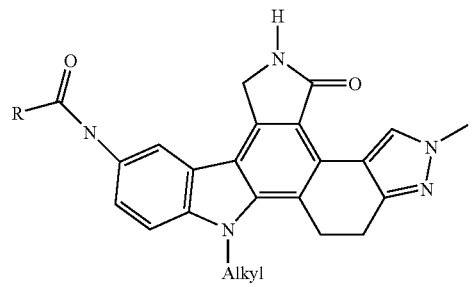

R = OR$^{15}$ Examples 50–69
R = R$^{20}$ Examples 74–82

Scheme 4 shows a route for the preparation of N-carbamates (examples 50–69) or amides (examples 74–82) from the corresponding aniline intermediates I-29. Amino intermediates I-29 were prepared by alkylation of the appropriate cyano-esters with the appropriate alkyl iodide or bromide followed by nitration, and subsequent RaNi reduction to provide the amino-lactam. The desired compounds were readily prepared from the amine.

Heteroaryl ketones may be prepared using standard Friedel-Crafts type acylation reactions.

EXAMPLES

Other features of the invention will become apparent in the course of the following descriptions of exemplary embodiments as shown in the following Tables 1–5. The compounds of Tables 1–5 show activity in the targets described herein at concentrations ranging from 0.1 nM to 10 μM. These examples are given for illustration of the invention and are not intended to be limiting thereof.

TABLE 1

| Ex. No. | R³ | R² | Q | R⁵ |
|---|---|---|---|---|
| 1 | cyclopentyl-NH-C(O)-O-CH₃ | H | CH₂CH₂ | OiPr |
| 2 | cyclohexyl-NH-C(O)-O-CH₃ | H | CH₂CH₂ | OiPr |
| 3 | 2-methoxy-pyrimidinyl | H | CH₂CH₂ | OiPr |
| 4 | 2-methoxy-benzoxazolyl | H | CH₂CH₂ | OiPr |
| 5 | 2-methoxy-benzothiazolyl | H | CH₂CH₂ | OiPr |
| 6 | 2-(O-l)-pyrimidinyl | CH₂CH₂CH₃ | CH₂CH₂ | O$^i$Pr |
| 7 | 2-(O-l)-pyrazinyl | H | CH₂CH₂ | O$^i$Pr |
| 8 | 2-(O-l)-pyrazinyl | CH₂CH₂CH₃ | CH₂CH₂ | O$^i$Pr |
| 9 | H | CH₂CH₂OH | CH₂CH₂ | 2-methoxy-benzothiazolyl |
| 10 | H | l-CH₂CH₂-O-benzothiazol-2-yl | CH₂CH₂ | 2-methoxy-benzothiazolyl |
| 11 | H | CH₂CH₂OH | CH₂CH₂ | 2-methoxy-benzoxazolyl |

TABLE 1-continued
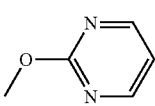
| Ex. No. | R³ | R² | Q | R⁵ |
|---|---|---|---|---|
| 12 | H | H | CH₂CH₂ | ![2-methoxypyrimidine] |
TABLE 2
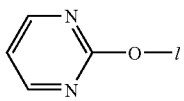
*R¹ is H, unless otherwise noted
| Ex. No. | R³ | R² | Q |
|---|---|---|---|
| 13 | pyrimidin-2-yloxy-l | H | CH₂CH₂ |
| 14 | pyrimidin-2-yloxy-l | CH₂CH₃ | CH₂CH₂ |
| 15 | pyrimidin-2-yloxy-l | CH₃ | CH₂CH₂ |
| 16 | pyrimidin-2-yloxy-l | cyclopentylmethyl | CH₂CH₂ |
| 17 | pyrazin-2-yloxy-l | H | CH₂CH₂ |
| 18 | pyrimidin-2-yloxy-l | CH₂CH₂CH₂CH₃ | CH₂CH₂ |

TABLE 2-continued

[Structure: tetracyclic core with R¹ on lactam N, R³ on indole benzene ring, R² on indole N, and pyrazole fused via O (Q linker) with N-methyl pyrazole]

*R¹ is H, unless otherwise noted

| Ex. No. | R³ | R² | Q |
|---|---|---|---|
| 19 | pyrimidin-2-yl-O— | CH(CH₃)₂ | CH₂CH₂ |
| 20 | pyrimidin-2-yl-O— | CH₂-cyclopropyl | CH₂CH₂ |
| 21 | pyrimidin-2-yl-O— | R² = CH₂-cyclopropyl; *R¹ = CH₂-cyclopropyl | CH₂CH₂ |
| 22 | 2-methoxypyrimidin-4-yl | CH₂CH(CH₃)₂ | CH₂CH₂ |
| 23 | 2-methoxypyrazin-5-yl | CH₂CH₃ | CH₂CH₂ |
| 24 | 2,6-dimethoxy-1,3,5-triazin-4-yl-O— | CH₂CH(CH₃)₂ | CH₂CH₂ |
| 25 | 2-furoyl | CH₂CH₃ | CH₂CH₂ |
| 26 | 2-thienoyl | H | CH₂CH₂ |
| 27 | 2-thienoyl | CH₂CH₃ | CH₂CH₂ |

TABLE 2-continued

*R¹ is H, unless otherwise noted

| Ex. No. | R³ | R² | Q |
|---|---|---|---|
| 28 | 2-furanyl-C(=O)- | H | CH₂CH₂ |
| 29 | 2-furanyl-C(=O)- | CH₂CH₂CH₃ | CH₂CH₂ |
| 30 | 2-furanyl-C(=O)- | CH₂CH(CH₃)₂ | CH₂CH₂ |
| 31 | 2-thienyl-C(=O)- | CH₂CH(CH₃)₂ | CH₂CH₂ |
| 32 | 2-furanyl-C(=O)- | CH₂CH=CH₂ | CH₂CH₂ |
| 33 | 2-furanyl-C(=O)- | CH₂COOEt | CH₂CH₂ |
| 34 | 2-furanyl-C(=O)- | CH₂COOH | CH₂CH₂ |
| 35 | 3-chloro-2-thienyl-C(=O)- | CH₂CH(CH₃)₂ | CH₂CH₂ |
| 36 | 3-thienyl-C(=O)- | CH₂CH(CH₃)₂ | CH₂CH₂ |

TABLE 2-continued
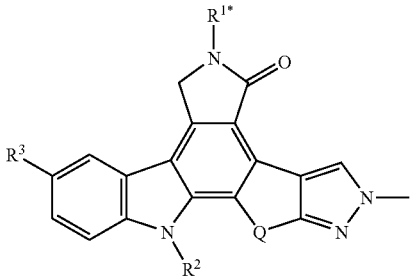
*R¹ is H, unless otherwise noted
| Ex. No. | R³ | R² | Q |
|---|---|---|---|
| 37 | 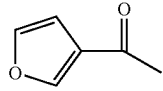 | CH₂CH(CH₃)₂ | CH₂CH₂ |
| 38 | 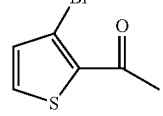 | CH₂CH(CH₃)₂ | CH₂CH₂ |
| 39 | 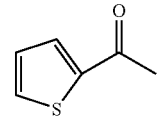 | CH₂CH₂CH₃ | CH₂CH₂ |
| 40 | 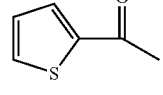 | CH(CH₃)₂ | CH₂CH₂ |
| 41 | 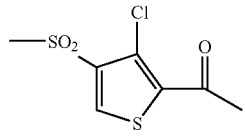 | CH₂CH(CH₃)₂ | CH₂CH₂ |
| 42 | 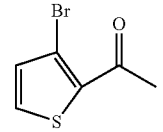 | CH₂CH₂NMe₂ | CH₂CH₂ |
| 43 | 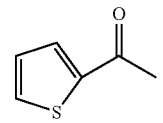 | (CH₂)₂—N(pyrrolidine) | CH₂CH₂ |
| 44 | 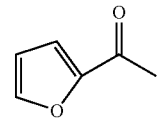 | (CH₂)₂—N(pyrrolidine) | CH₂CH₂ |
| 45 | 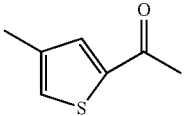 | CH₂CH(CH₃)₂ | CH₂CH₂ |

TABLE 2-continued

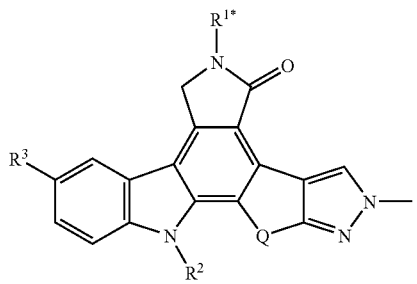

*R¹ is H, unless otherwise noted

| Ex. No. | R³ | R² | Q |
|---|---|---|---|
| 46 | 2-acetylthiophene | $(CH_2)_6$-pyrrolidine | $CH_2CH_2$ |
| 47 | 3-methyl-2-acetylthiophene | $(CH_2)_2$-pyrrolidine | $CH_2CH_2$ |
| 48 | 4-methyl-2-acetylthiophene | $(CH_2)_2$-pyrrolidine | $CH_2CH_2$ |
| 49 | 3-chloro-2-acetylthiophene | $(CH_2)_2$-pyrrolidine | $CH_2CH_2$ |
| 50 | isopropyl carbamate | $CH_2CH_2CH_3$ | $CH_2CH_2$ |
| 51 | ethyl carbamate | $CH_2CH_2CH_3$ | $CH_2CH_2$ |
| 52 | isobutyl carbamate | $CH_2CH_2CH_3$ | $CH_2CH_2$ |
| 53 | propyl carbamate | $CH_2CH_2CH_3$ | $CH_2CH_2$ |
| 54 | 2-fluoroethyl carbamate | $CH_2CH_2CH_3$ | $CH_2CH_2$ |

TABLE 2-continued

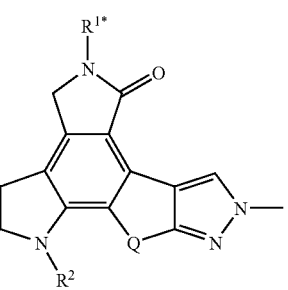

*R¹ is H, unless otherwise noted

| Ex. No. | R³ | R² | Q |
|---|---|---|---|
| 55 | ClCH₂CH₂OC(O)NH- | CH₂CH₂CH₃ | CH₂CH₂ |
| 56 | CH₃CH₂OC(O)NH- | CH(CH₃)₂ | CH₂CH₂ |
| 57 | (CH₃)₂CHCH₂OC(O)NH- | CH₂CH(CH₃)₂ | CH₂CH₂ |
| 58 | (CH₃)₂CHOC(O)NH- | CH₂CH(CH₃)₂ | CH₂CH₂ |
| 59 | CH₃CH₂CH₂OC(O)NH- | CH₂CH(CH₃)₂ | CH₂CH₂ |
| 60 | CH₃CH₂OC(O)NH- | CH₂CH(CH₃)₂ | CH₂CH₂ |
| 61 | (CH₃)₂CHOC(O)NH- | CH(CH₃)₂ | CH₂CH₂ |
| 62 | BrCH₂CH₂OC(O)N(CH₃)- | CH₂CH₂CH₃ | CH₂CH₂ |
| 63 | FCH₂CH₂OC(O)N(CH₃)- | CH₂CH(CH₃)₂ | CH₂CH₂ |
| 64 | ClCH₂CH₂OC(O)N(CH₃)- | CH₂CH(CH₃)₂ | CH₂CH₂ |

TABLE 2-continued

*R¹ is H, unless otherwise noted

| Ex. No. | R³ | R² | Q |
|---|---|---|---|
| 65 | Br-phenyl-CH₂CH₂-O-C(O)-NH-CH₃ | CH₂CH(CH₃)₂ | CH₂CH₂ |
| 66 | (CH₃)₂CHCH₂-O-C(O)-NH-CH₃ | CH(CH₃)₂ | CH₂CH₂ |
| 67 | pyrrolidinyl-CH₂CH₂-O-C(O)-NH-CH₃ | CH(CH₃)₂ | CH₂CH₂ |
| 68 | piperidinyl-CH₂CH₂-O-C(O)-NH-CH₃ | CH(CH₃)₂ | CH₂CH₂ |
| 69 | pyridyl-CH₂CH₂-O-C(O)-NH-CH₃ | CH(CH₃)₂ | CH₂CH₂ |
| 70 | pyrrolidinyl-C(O)-O- | CH₂CH₃ | CH₂CH₂ |
| 71 | pyrrolidinyl-C(O)-O- | CH₂CH(CH₃)₂ | CH₂CH₂ |
| 72 | pyrrolidinyl-C(O)-O-CH₃ | CH(CH₃)₂ | CH₂CH₂ |
| 73 | (N-methyl-piperidin-4-yl)-N(CH₃)-C(O)-O- | CH₂CH(CH₃)₂ | CH₂CH₂ |

TABLE 2-continued

*R¹ is H, unless otherwise noted

| Ex. No. | R³ | R² | Q |
|---|---|---|---|
| 74 | pyridine-4-carboxamide | CH(CH$_3$)$_2$ | CH$_2$CH$_2$ |
| 75 | thiophene-2-carboxamide | CH$_2$CH$_2$CH$_3$ | CH$_2$CH$_2$ |
| 76 | furan-2-carboxamide | CH$_2$CH$_2$CH$_3$ | CH$_2$CH$_2$ |
| 77 | pyridine-3-carboxamide | CH(CH$_3$)$_2$ | CH$_2$CH$_2$ |
| 78 | pyridine-4-carboxamide | CH(CH$_3$)$_2$ | CH$_2$CH$_2$ |
| 79 | thiophene-2-carboxamide | CH$_2$CH(CH$_3$)$_2$ | CH$_2$CH$_2$ |
| 80 | furan-2-carboxamide | CH$_2$CH(CH$_3$)$_2$ | CH$_2$CH$_2$ |
| 81 | isoxazole-5-carboxamide | CH$_2$CH$_2$CH$_3$ | CH$_2$CH$_2$ |
| 82 | isoxazole-5-carboxamide | CH$_2$CH(CH$_3$)$_2$ | CH$_2$CH$_2$ |

TABLE 3
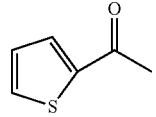
| Ex. No. | R³ | R² | Q |
|---|---|---|---|
| 83 | 2-acetylthiophene | CH₂CH(CH₃)₂ | CH₂CH₂ |
| 84 | 2-acetylfuran | CH₂CH(CH₃)₂ | CH₂CH₂ |
| 85 | 2-methoxypyrimidine | CH₂CH(CH₃)₂ | CH₂CH₂ |
TABLE 4
| Example No. | Structure | MS m/e (M + 1) |
|---|---|---|
| 86 | 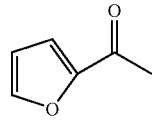 | 509 |
| 87 | 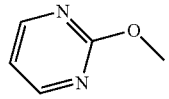 | 511 |

TABLE 4-continued

| Example No. | Structure | MS m/e (M + 1) |
|---|---|---|
| 88 | 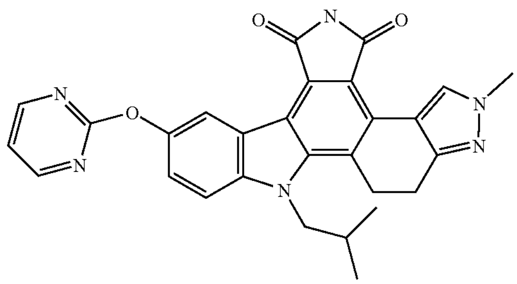 | 493 |
| 89 | 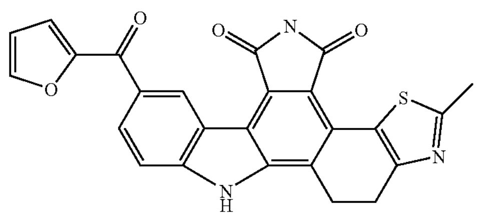 | 454 |
| 90 | 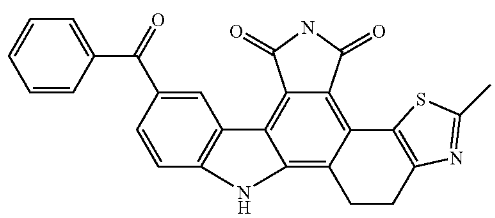 | 464 |
| 91 | 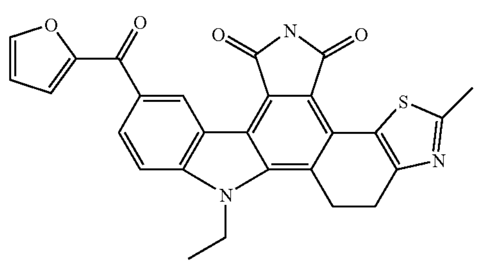 | 482 |
| 92 | 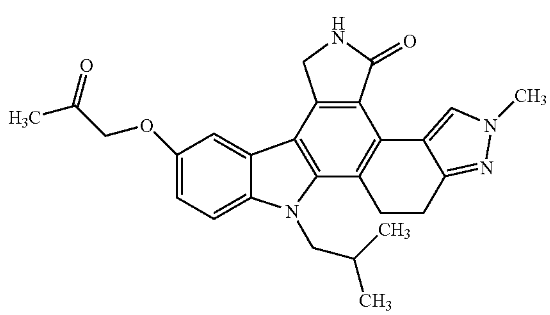 | 457 |

TABLE 4-continued
| Example No. | Structure | MS m/e (M + 1) |
|---|---|---|
| 93 | 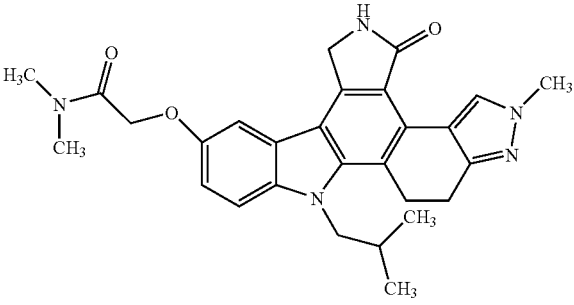 | 486 |
| 94 | 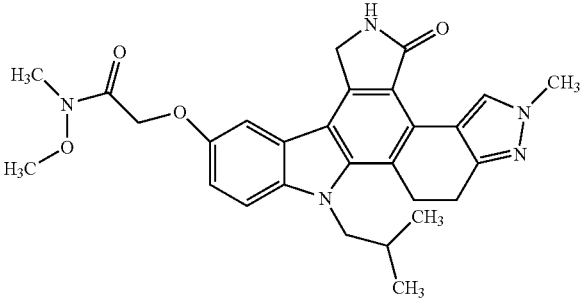 | 502 |
| 95 | 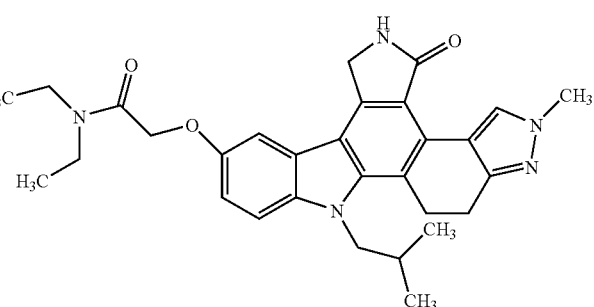 | 514 |
| 96 | 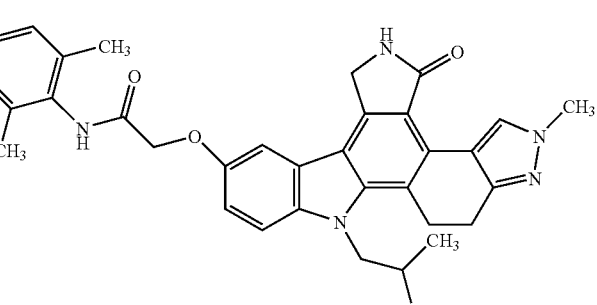 | 562 |
| 97 | 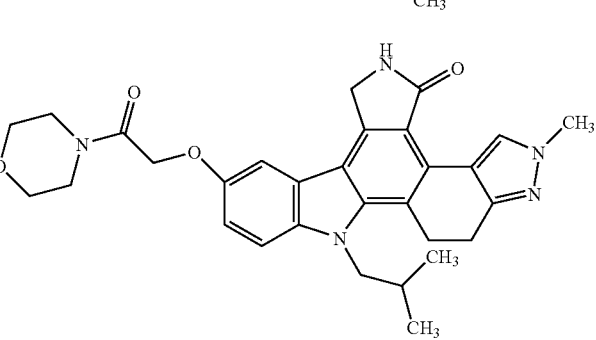 | 528 |

TABLE 4-continued
| Example No. | Structure | MS m/e (M + 1) |
|---|---|---|
| 98 | 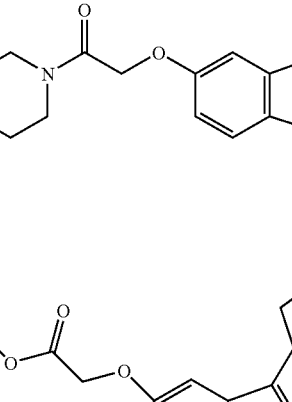 | 555 |
| 99 | 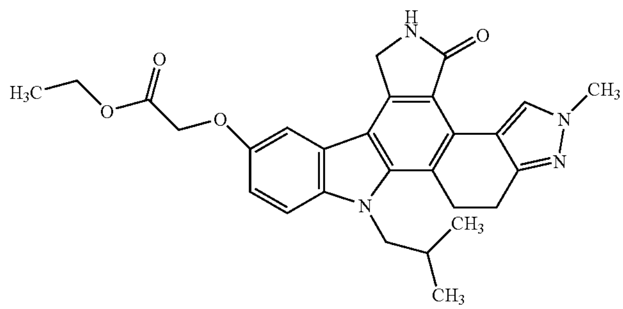 | 487 |
| 100 | 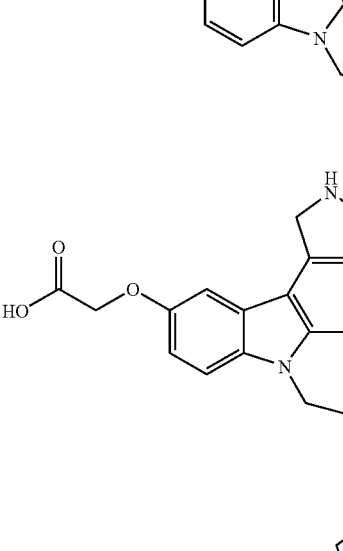 | 459 |
| 101 | 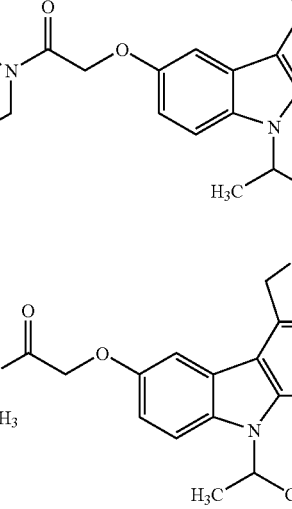 | 500 |
| 102 | 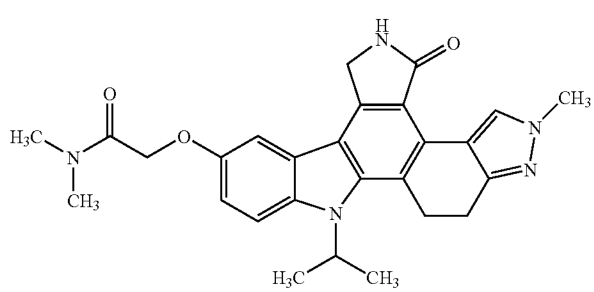 | 472 |

TABLE 4-continued
| Example No. | Structure | MS m/e (M + 1) |
|---|---|---|
| 103 | 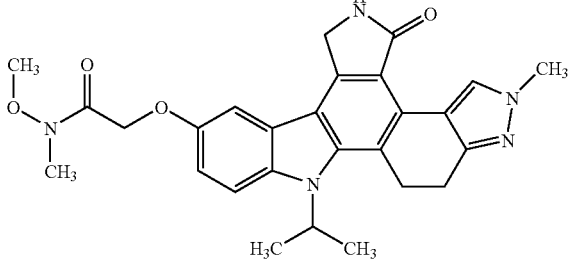 | 488 |
| 104 | 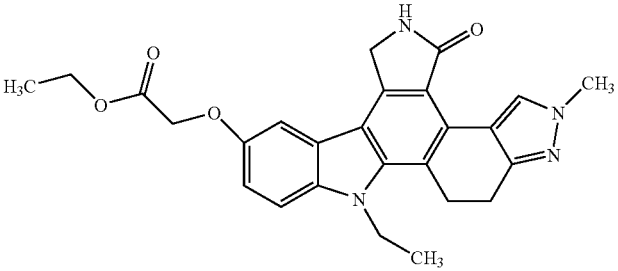 | 459 |
| 105 | 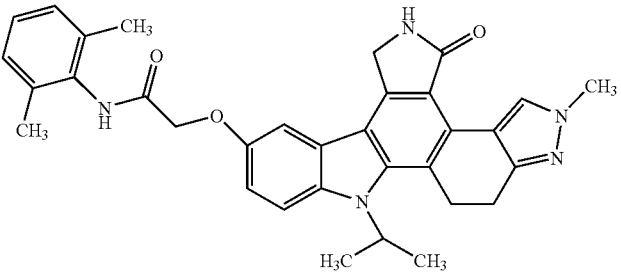 | 548 |
| 106 | 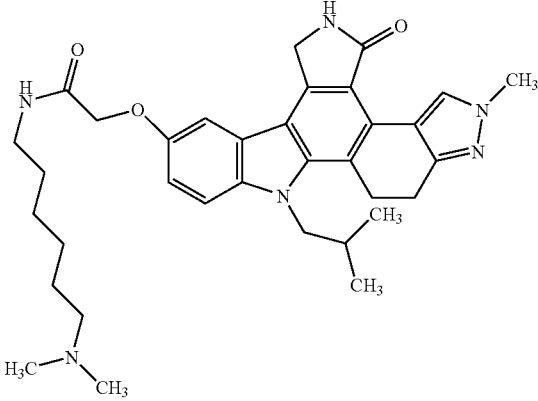 | 585 |
| 107 | 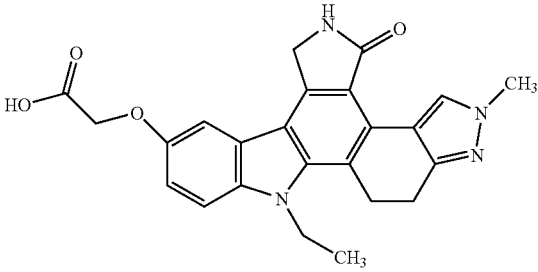 | 430 |

TABLE 4-continued
| Example No. | Structure | MS m/e (M + 1) |
|---|---|---|
| 108 | 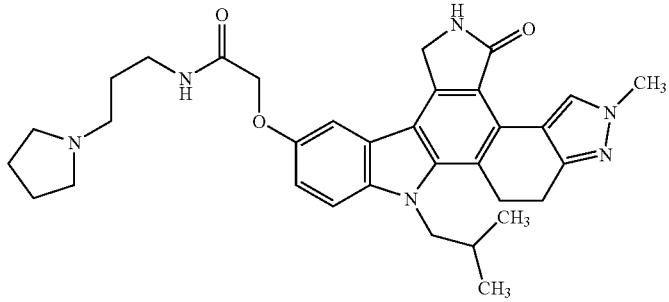 | 569 |
| 109 | 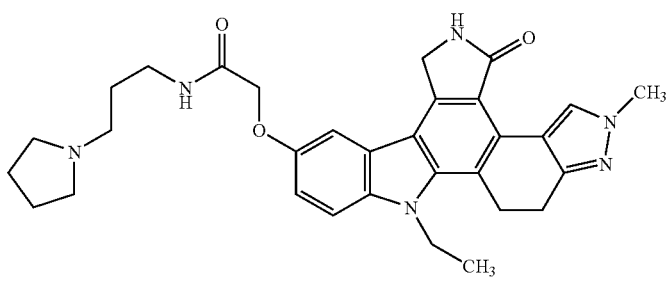 | 541 |
| 110 | 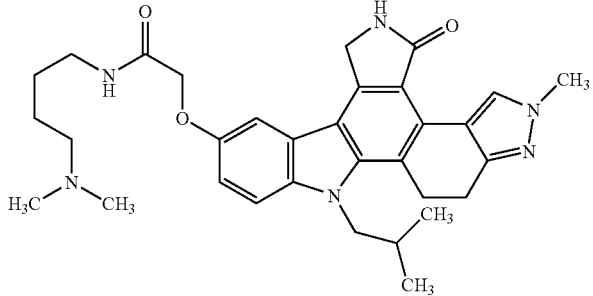 | 557 |
| 111 | 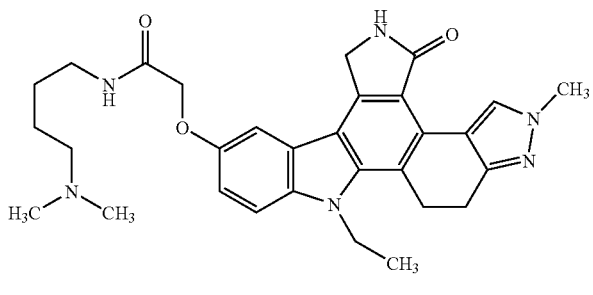 | 529 |
| 112 | 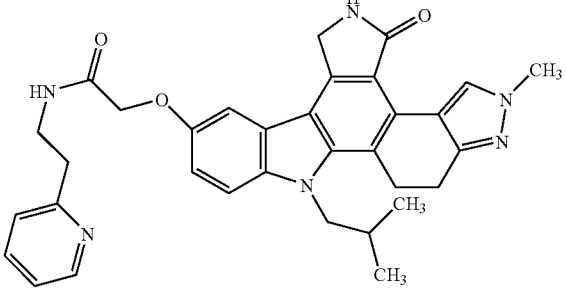 | 563 |

TABLE 4-continued
| Example No. | Structure | MS m/e (M + 1) |
|---|---|---|
| 113 | 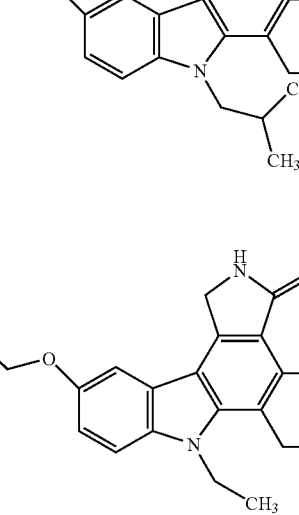 | 577 |
| 114 | 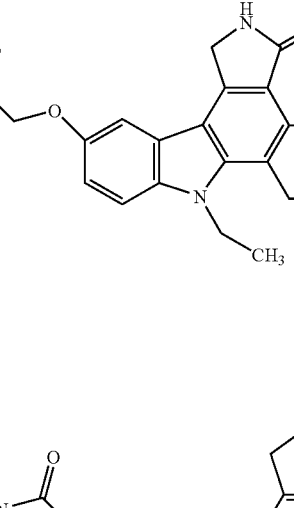 | 535 |
| 115 | 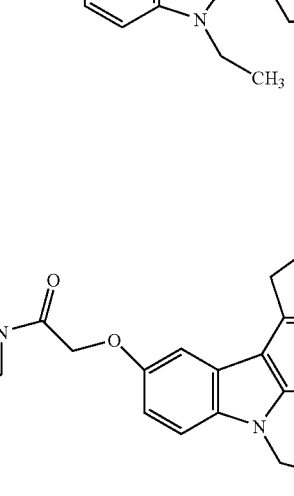 | 549 |
| 116 | 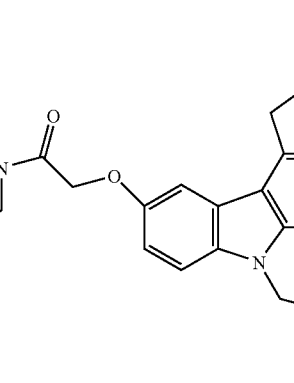 | 571 |

TABLE 4-continued

| Example No. | Structure | MS m/e (M + 1) |
|---|---|---|
| 117 | 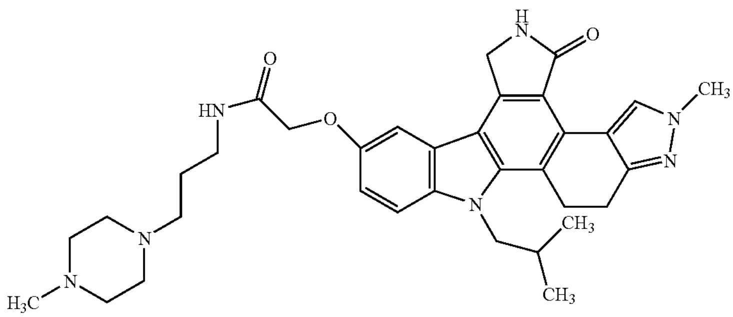 | 598 |
| 118 | 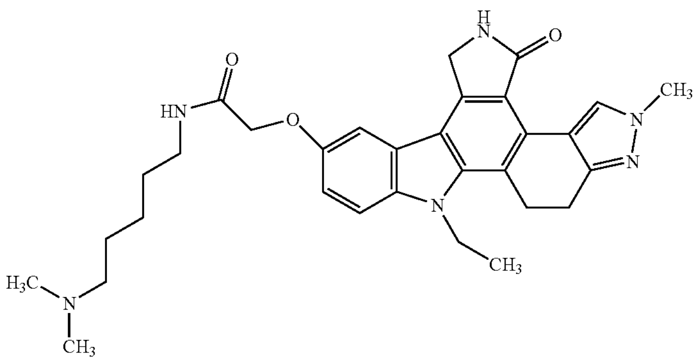 | 543 |
| 119 | 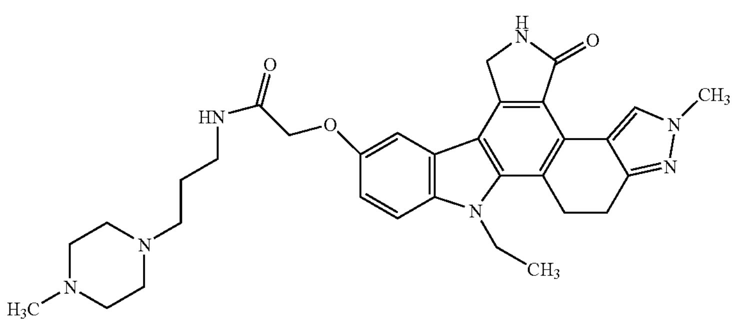 | 570 |
| 120 | 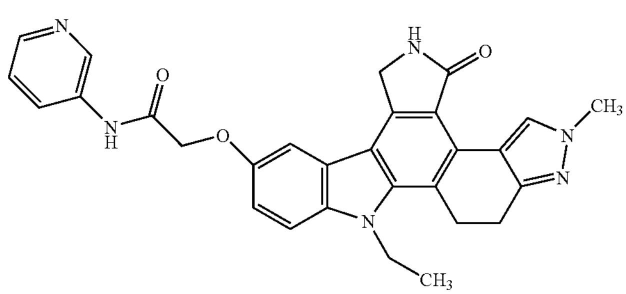 | 507 |

TABLE 4-continued

| Example No. | Structure | MS m/e (M + 1) |
|---|---|---|
| 121 | 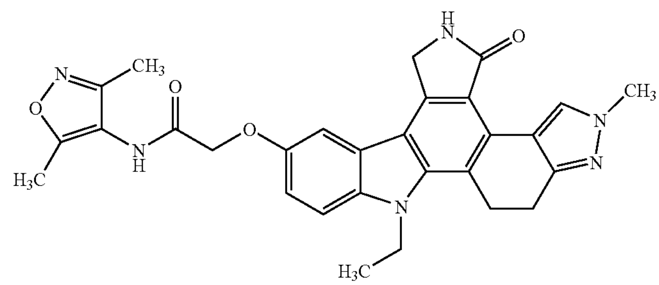 | 525 |
| 122 | 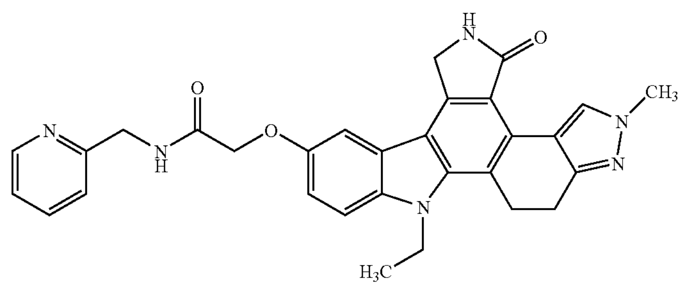 | 521 |
| 123 | 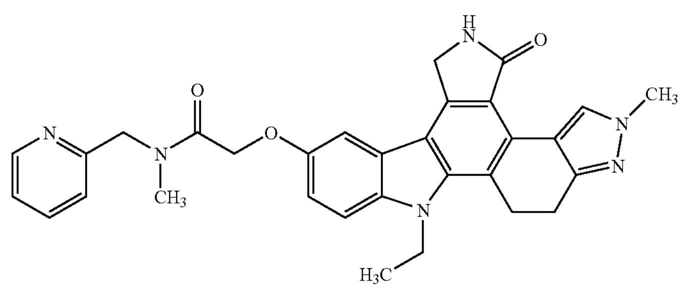 | 535 |
| 124 | 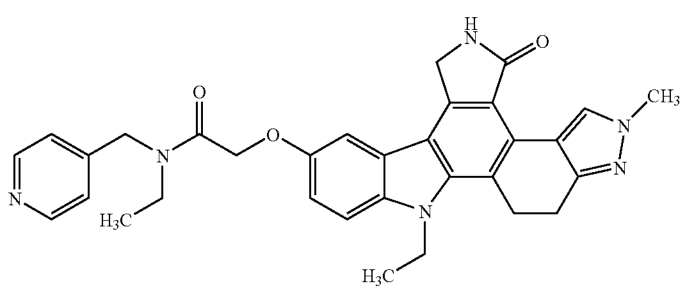 | 549 |
| 125 | 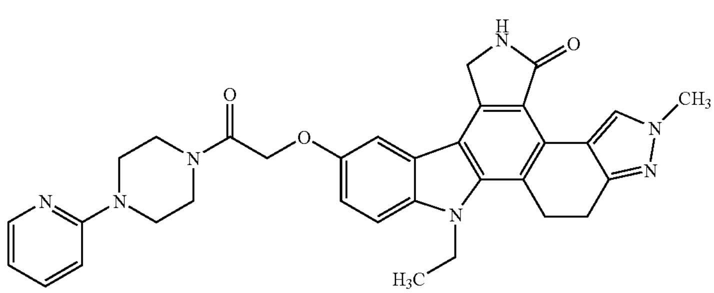 | 576 |

TABLE 4-continued
| Example No. | Structure | MS m/e (M + 1) |
|---|---|---|
| 126 | 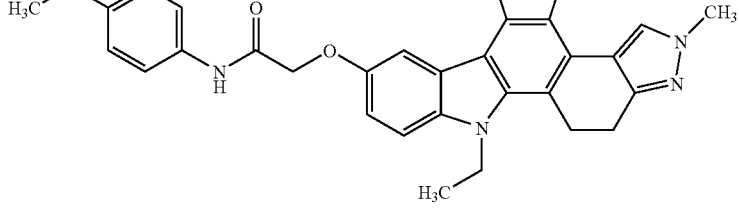 | 549 |
| 127 | 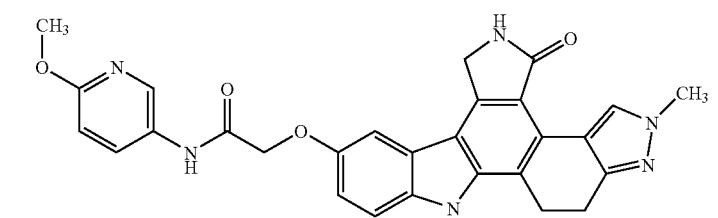 | 537 |
| 128 | 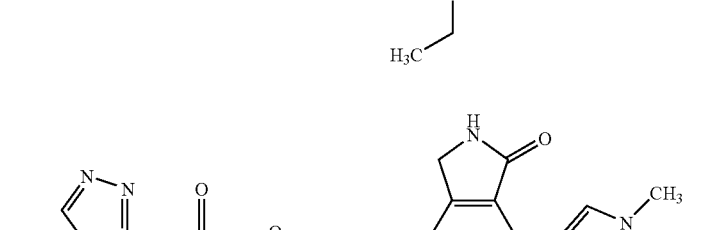 | 542 |
| 129 | 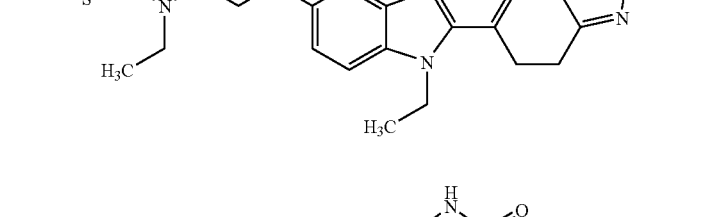 | 573 |
| 130 | 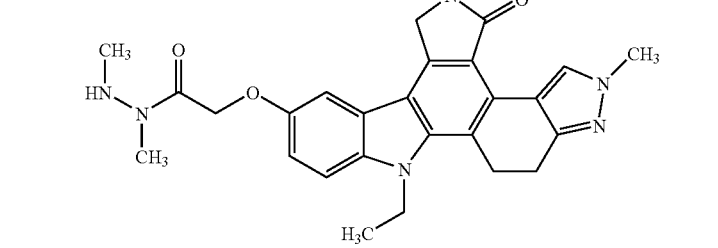 | 563 |

TABLE 4-continued

| Example No. | Structure | MS m/e (M + 1) |
|---|---|---|
| 131 | 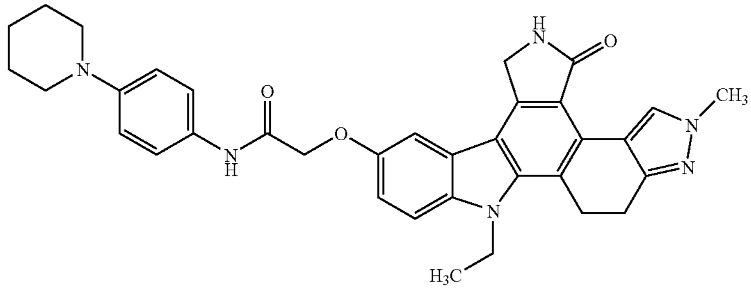 | 589 |
| 132 | 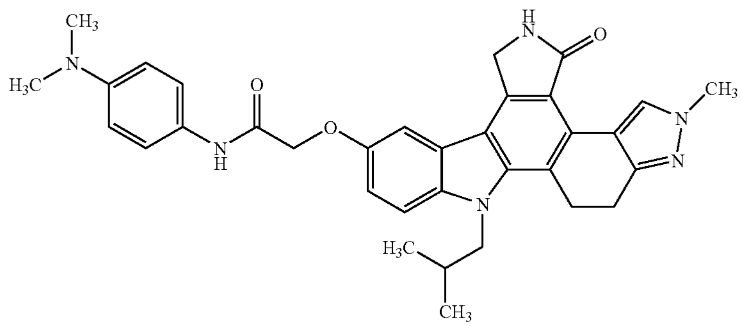 | 577 |
| 133 | 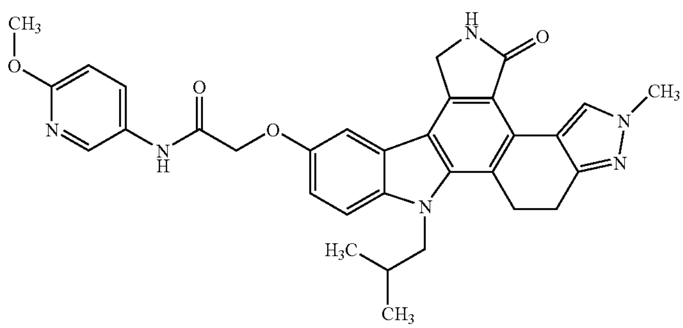 | 565 |
| 134 | 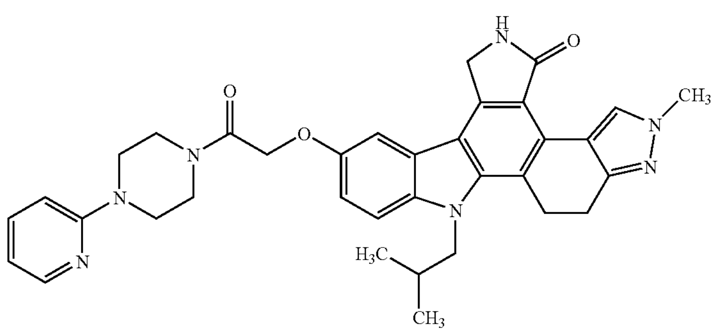 | 604 |
| 135 | 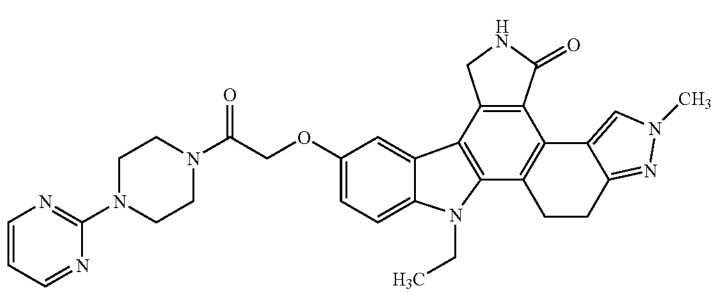 | 577 |

TABLE 4-continued

| Example No. | Structure | MS m/e (M + 1) |
|---|---|---|
| 200 | 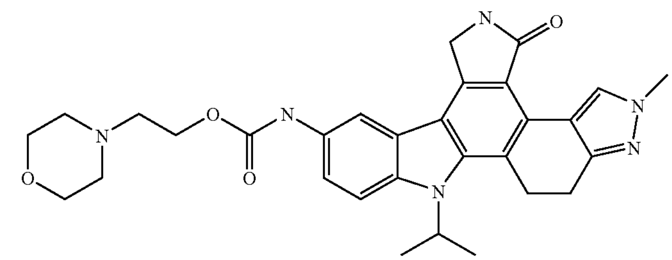 | 543 |
| 201 | 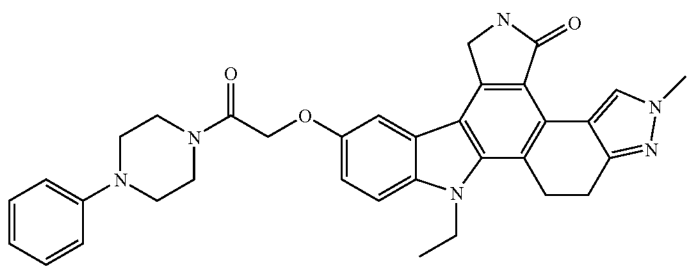 | 575 |
| 202 | 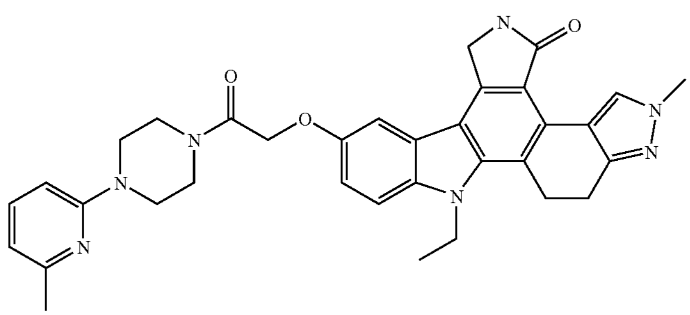 | 590 |
| 203 | 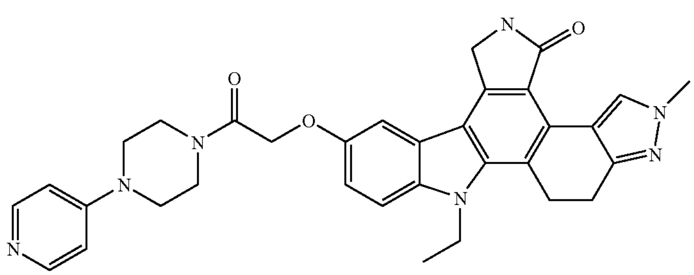 | 576 |
| 204 | 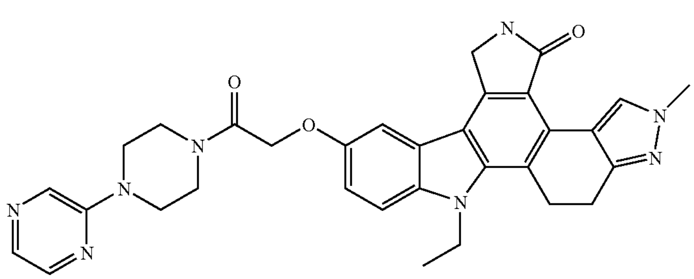 | 577 |

TABLE 4-continued

| Example No. | Structure | MS m/e (M + 1) |
|---|---|---|
| 205 | 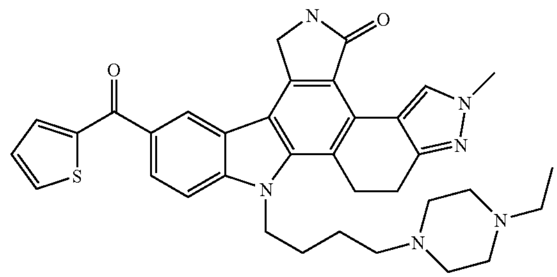 | 607 |
| 206 | 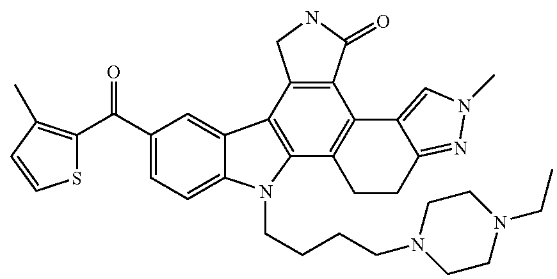 | 621 |
| 207 | 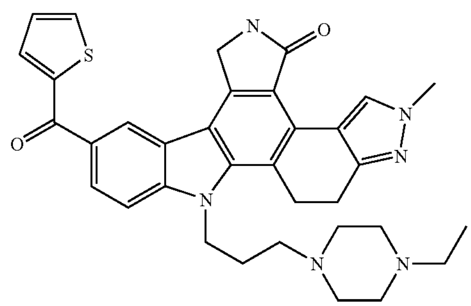 | 593 |
| 208 | 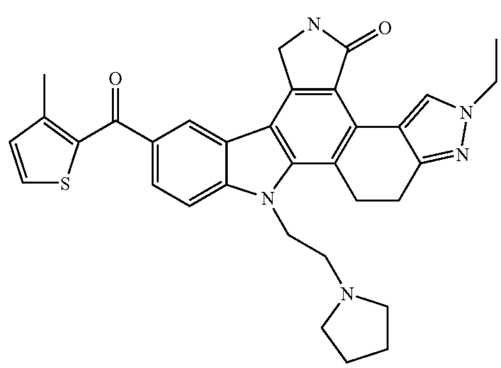 | 564 |
| 209 | 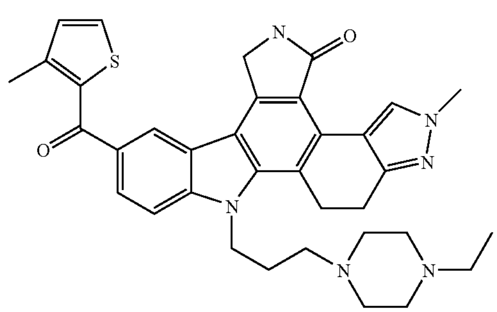 | 607 |

TABLE 4-continued

| Example No. | Structure | MS m/e (M + 1) |
|---|---|---|
| 210 | 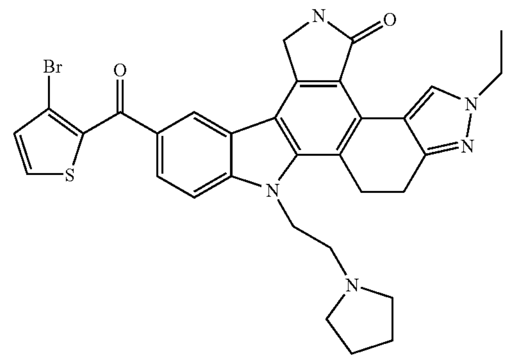 | 629 |
| 211 | 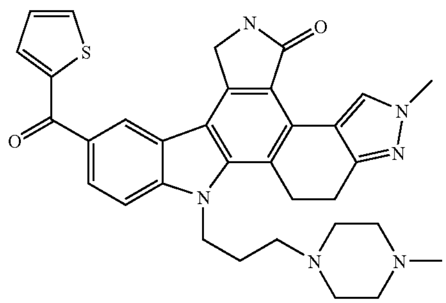 | 579 |
| 212 | 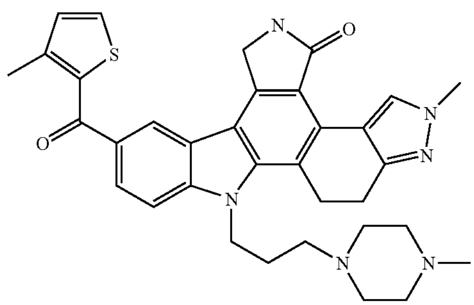 | 593 |

TABLE 5

| Eg. | R³ | R² | Q | R⁵ |
|---|---|---|---|---|
| 136 | (pyrrolidinone-N-CH₂CH₂-O-CH₂-) | CH₂CH₂CH₂OH | CH₂ | H |

TABLE 5-continued
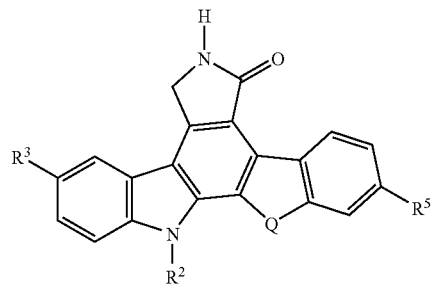
| Eg. | R³ | R² | Q | R⁵ |
|---|---|---|---|---|
| 137 | 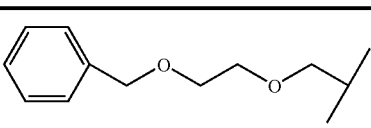 | CH₂CH₂CH₂OH | CH₂ | H |
| 138 | 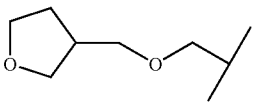 | CH₂CH₂CH₂OH | CH₂ | H |
| 139 | 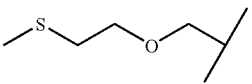 | CH₂CH₂CH₂OH | CH₂ | H |
| 140 | 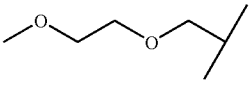 | CH₂CH₂CH₂OH | CH₂ | H |
| 141 | 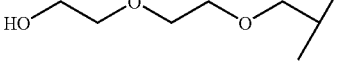 | CH₂CH₂CH₂OH | CH₂ | H |
| 142 | 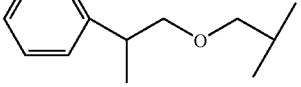 | CH₂CH₂CH₂OH | CH₂ | H |
| 143 | 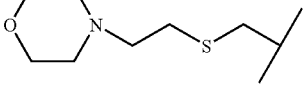 | CH₂CH₂CH₂OH | CH₂ | H |
| 144 | 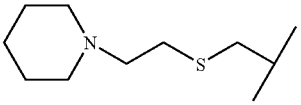 | CH₂CH₂CH₂OH | CH₂ | H |
| 145 | 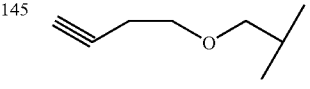 | CH₂CH₂CH₂OH | CH₂ | H |
| 146 | 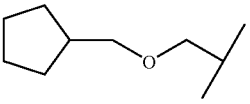 | CH₂CH₂CH₂OH | CH₂ | H |
| 147 | 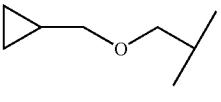 | H | CH₂CH₂ | OCH₃ |

TABLE 5-continued
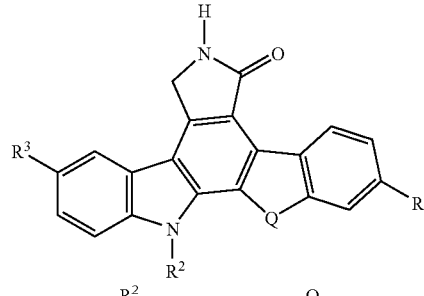
| Eg. | R³ | R² | Q | R⁵ |
|---|---|---|---|---|
| 148 | 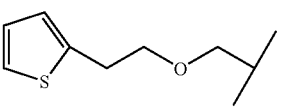 | CH₂CH₂OH | CH₂ | OCH₃ |
| 149 | 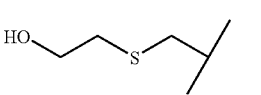 | CH₂CH₂OH | CH₂CH₂ | OCH₃ |
| 150 | 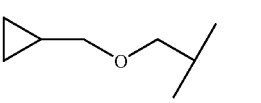 | CH₂CH₂CH₂OH | CH₂ | H |
| 151 | 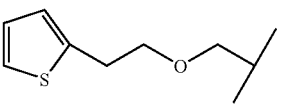 | CH₂CH₂CH₂OH | CH₂ | H |
| 152 | 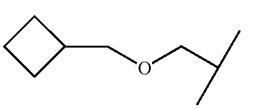 | H | CH₂ | H |
| 153 | 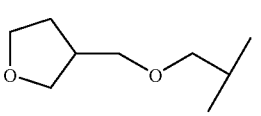 | H | CH₂ | H |
| 154 | 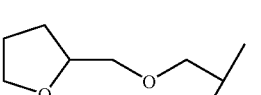 | H | CH₂ | H |
| 155 | 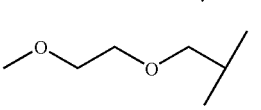 | H | CH₂ | H |
| 156 | 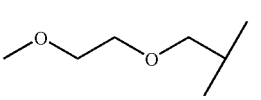 | H | CH₂ | OCH₃ |
| 157 | 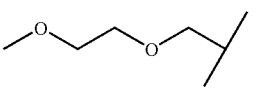 | 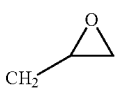 | CH₂ | H |
| 158 | 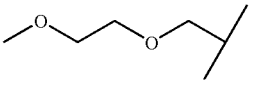 | CH₂CH(OH)—CH₃ | CH₂ | H |
| 159 | 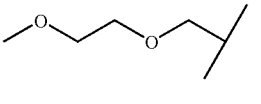 | H | CH(OH)CH₃ | H |

TABLE 5-continued
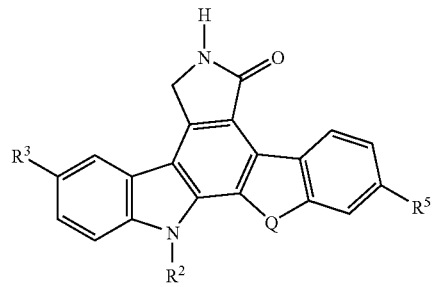
| Eg. | R³ | R² | Q | R⁵ |
|---|---|---|---|---|
| 160 | 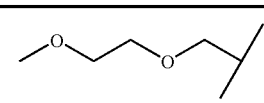 | CH₂CH₂OH | CH₂CH₂ | OCH₃ |
| 161 | 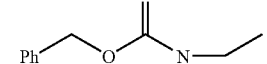 | H | CH₂CH₂ | OiPr |
| 162 | 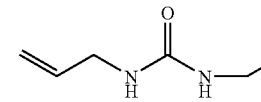 | CH₂CH₂OH | CH₂CH₂ | OCH₃ |
| 163 | 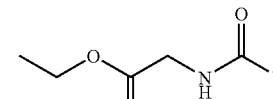 | H | CH₂CH₂ | OCH₃ |
| 164 | 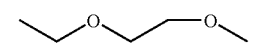 | H | CH₂CH₂ | OiPr |
| 165 | 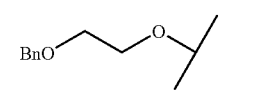 | H | CH₂CH₂ | OiPr |
| 166 | 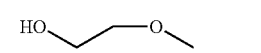 | H | CH₂CH₂ | OiPr |
| 167 | H | CH₂CH₂OH | CH₂CH₂ | 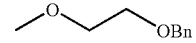 |
| 168 | H | CH₂CH₂OH | CH₂CH₂ | O(CH₂)₂OH |
| 169 | H | CH₂CH₂OH | CH₂CH₂ | 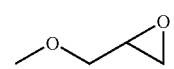 |
| 170 | H | CH₂CH₂OH | CH₂CH₂ | O[(CH₂)₂O]₂Me |
| 171 | H | CH₂CH₂OH | CH₂CH₂ | 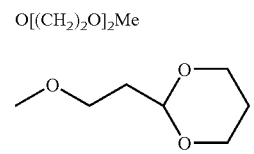 |
| 172 | H | CH₂CH₂OH | CH₂CH₂ | 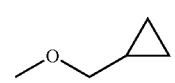 |
| 173 | H | CH₂CH₂OH | CH₂CH₂ | 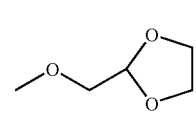 |

TABLE 5-continued

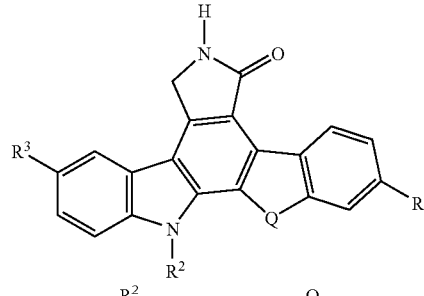

| Eg. | R³ | R² | Q | R⁵ |
|---|---|---|---|---|
| 174 | H | CH₂CH₂OH | CH₂CH₂ | 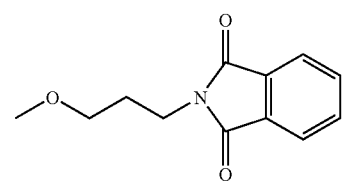 |
| 175 | H | CH₂CH₂OH | CH₂CH₂ | OCH(CH₃)CO₂Et |
| 176 | H | CH₂CH₂OH | CH₂CH₂ | 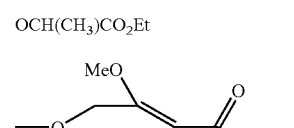 |
| 177 | H | CH₂CH₂OH | CH₂CH₂ | OCH₂CO₂tBu |
| 178 | H | H | CH₂CH₂ | 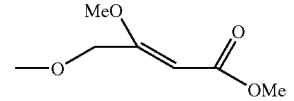 |
| 179 | H | CH₂CH₂OH | CH₂CH₂ | OCH₂CO₂Et |
| 180 | H | CH₂CH₂OH | CH₂CH₂ | 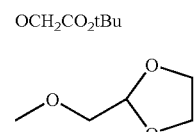 |
| 181 | H | CH₂CH₂OH | CH₂CH₂ | O(CH₂)₂OMe |
| 182 | H | CH₂CH₂OH | CH₂CH₂ | O(CH₂)₃CN |
| 183 | H | CH₂CH₂OH | CH₂CH₂ | O(CH₂)₅CN |
| 184 | H | CH₂CH₂OH | CH₂CH₂ | O(CH₂)₂OEt |
| 185 | H | CH₂CH₂OH | CH₂CH₂ | O(CH₂)₄CN |
| 186 | H | CH₂CH₂OH | CH₂CH₂ | O(CH₂)₆CN |
| 187 | H | CH₂CH₂OH | CH₂CH₂ | OCH₂CN |
| 188 | H | CH₂CH₂OH | CH₂CH₂ | O(CH₂)₄C(=NH)OEt |
| 189 | H | CH₂CH₂OH | CH₂CH₂ | O(CH₂)₄CO₂H |
| 190 | H | CH₂CH₂OH | CH₂CH₂ | O(CH₂)₆CONH₂ |
| 191 | H | CH₂CO₂Et | CH₂ | OCH₂CO₂Et |
| 192 | H | H | CH₂ | OCH₂CO₂Et |
| 193 | H | H | CH₂ | OCH₂CN |
| 194 | H | H | CH₂ | OCH₂CH₂OH |
| 195 | H | CH₂CH₂OH | CH₂ | OCH₂CH₂OH |
| 196 | H | H | CH₂ | OCH₂CH(OH)CH₂OH |
| 197 | H | H | CH₂ | OCH₂CONMe₂ |
| 198 | H | H | CH₂ | OCH₂CH(OH)CH₂NMe₂ |
| 199 | H | H | CH₂ | 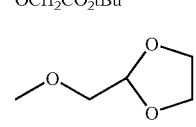 |

General Procedure for Examples 1 and 2

A mixture of phenol intermediate I-14 (0.05 mmol.), isocyanate (0.05 mmol.), cesium hydrogen carbonate (0.5 mg) and tetrahydrofuran (0.5 mL) was stirred at room temperature for 1 day. The solvent was evaporated and the residue stirred for 8 hours with ethyl acetate and 3N HCl. The ethyl acetate was removed by evaporation and the aqueous solution was decanted from the solid. The residue was triturated with methanol and the product collected.

Example 1

(26%) MS m/e 510 (M+1); $^1$H NMR (DMSO-$d_6$) δ 11.60 (s, 1H), 8.33 (s, 1H), 8.16 (d, 1H), 7.63 (d, 1H), 7.53 (s, 1H), 7.51 (d, 1H), 7.18 (d, 1H), 6.86 (s, 1H), 6.77 (d, 1H), 4.77 (s, 2H), 4.68 (m, 1H), 3.87 (m, 1H), 2.98 (t, 2H), 2.83 (t, 2H), 1.85 (m, 2H), 1.69 (m, 2H), 1.52 (m, 4H), 1.31 (d, 6H).

Example 2

(36%) MS m/e 524 (M+1); $^1$H NMR (DMSO-$d_6$) 11.59 (s, 1H), 8.33 (s, 1H), 8.16 (d, 1H), 7.63 (s, 1H), 7.52 (d, 1H), 7.17 (d, 1H), 6.86 (s, 1H), 6.78 (d, 1H), 4.77 9s, 2H), 4.68 m, 1H), 3.00 (t, 2H), 2.83 (t, 2H), 1.87 (m, 2H), 1.72 (m, 2H), 1.56 (d, 1H), 1.30 (d, 6H).

Example 3

A suspension of sodium hydride (2.44 mg, 1.22 eq.) in 0.5 mL of THF was stirred under $N_2$ as phenol intermediate I-14 (20.6 mg, 0.05 mmol) in 2.0 mL of THF:DMF (1:1) was added dropwise. After 10 minutes of stirring, 2-bromopyrimidine (8.9 mg, 1.12 equivalents) in 0.5 mL of THF was added. The mixture was stirred at 60° C. for 14 hours. The mixture was cooled to room temperature, diluted with $CH_2Cl_2$/MeOH, filtered through celite and concentrated. Purification was achieved by preparative TLC with $CH_2Cl_2$/MeOH (9:1) to afford the product (4.0 mg, 17%) (MS: 477 m/e (M+H)$^+$).

Example 4

The compound was prepared according to the procedure of Example 3 using phenol intermediate I-14 and 2-chlorobenzoxazole; 40 hr; preparative TLC (10% MeOH in $CH_2Cl_2$); yield 28%; MS: 516 m/e (M+1)$^+$.

Example 5

The compound was prepared according to the procedure of Example 3 using intermediate I-14 and 2-chlorobenzothiazole; 40 hr; preparative TLC (10% MeOH in $CH_2Cl_2$); yield 13%; MS: 531 m/e (M+1)$^+$.

Example 6

To a mixture of Example 3 (25.0 mg, 0.052 mmol) and cesium carbonate (81 mg, 5.0 eq) in 2.0 mL of $CH_3CN$ was added n-propyl bromide (47 ul, 10.0 eq.) under $N_2$. After stirring at 90° C. for 14 hours, the mixture was diluted with $CH_2Cl_2$, filtered through celite and concentrated. Purification by preparative TLC with 95% of $CH_2Cl_2$/MeOH afforded the product (15.0 mg, 56%); MS: m/e 519 (M+1)$^+$.

Example 7

The compound was prepared using to the procedure of Example 3 using intermediate I-14 and 2-bromopyrazine; preparative TLC (10% MeOH in $CH_2Cl_2$); MS 499 m/e (M+1)$^+$.

Example 8

The compound was prepared according to the procedure of Example 6 using Example 7 as starting material. MS m/e 519 (M+1).

Synthesis of Phenol Intermediates I-18 and I-19.

A mixture of $AlCl_3$ (800 mg, 6 mmol) in dichloroethane (8 mL) was stirred at 0° C. as EtSH (1.40 mL) was added and followed by intermediate I-41 (398 mg, 1 mmol). The reaction was stirred at 50° C. for 48 hr. To the reaction mixture was added 5 mL of 1N HCl and the mixture was stirred at rt for 0.5 hr. Filtration provided 240 mg (63%) of intermediate I-18 (MS: 385 m/e (M+1)$^+$. By a similar method intermediate I-19 was prepared from the methoxy N-H derivative.

Examples 9 and 10

A suspension of sodium hydride (12.2 mg, 1.22 eq.) in 0.5 mL of THF was stirred under $N_2$ as phenol intermediate I-18 (76.8 mg, 0.2 mmol) in 4.0 mL of THF:DMF (1:1) was added dropwise at room temperature. After 10 minutes stirring, 2-chloro-benzothiazole (38 mg, 1.12 eq.) in 0.5 mL of THF was added. The mixture was then stirred at 60° C. for 40 hours, diluted with $CH_2Cl_2$/MeOH, filtered through celite and concentrated. Purification by preparative TLC with (9:1) $CH_2Cl_2$/MeOH afforded the mono product Example 9 (6.0 mg, yield 6%) (MS: 517 m/e (M+H)$^+$) and the dialkylated product Example 10 (60 mg, yield 46%) (MS: 651 m/e (M+H)$^+$).

Example 11

The compound was prepared according to the procedure of Example 10 using phenol intermediate I-18 and 2-chlorobenzoxazole; 36 hr; preparative TLC (10% MeOH in $CH_2Cl_2$); yield 11%; MS: 502 m/e (M+1)$^+$.

Example 12

The compound was prepared according to the procedure of Example 10 using intermediate I-19 and 2-bromopyrimidine; 36 hr; preparative TLC (10% MeOH in $CH_2Cl_2$); yield 25%; MS: 419 m/e (M+1)$^+$.

Example 13

The compound was prepared according to the procedure for Example 3 using phenol intermediate I-22 and 2-bromopyrimidine; 30 hr; preparative TLC (10% MeOH in $CH_2Cl_2$); yield 53%; MS: 423 m/e (M+1)$^+$.

Example 14

The compound was prepared according to the procedure for Example 6 using Example 13 and iodoethane; 14 hr; preparative TLC (10% MeOH in $CH_2Cl_2$); yield 19%; MS: 451 m/e (M+1)$^+$.

Example 15

The compound was prepared according to the procedure for Example 6 using Example 13 and iodomethane; 14 hr; preparative TLC (10% MeOH in $CH_2Cl_2$); yield 28%; MS: 459 m/e (M+23)$^+$.

Example 16

The compound was prepared according to the procedure for Example 6 using Example 13 and cyclopentyl bromide; 14 hr; preparative TLC (10% MeOH in $CH_2Cl_2$); yield 38%; MS: 513 m/e (M+23)$^+$.

Example 17

A mixture of phenol intermediate I-22 (17.2 mg, 0.05 mmol), potassium t-butoxide (33.7 mg, 6 eq.) and t-butylammonium bromide (0.97 mg, 0.06 eq) was mixed and stirred for 5 minutes, then 1.0 mL of chloropyrazine was added, then stirred at room temperature for 5 minutes and at 90° C. for 1 hour. The mixture was cooled to room temperature, excess of the chloropyrazine was evaporated off and the resulting residue was diluted with $CH_2Cl_2$/MeOH. Purification by preparative TLC with (9:1) $CH_2Cl_2$/MeOH afforded the mono product (11.0 mg, yield 52%) MS: 423 m/e $(M+1)^+$.

Example 18

The compound was prepared according to the procedure for Example 6 using Example 13 and butyl bromide; 14 hr; preparative TLC (10% MeOH in $CH_2Cl_2$); yield 38%; MS: 479 m/e $(M+1)^+$.

Example 19

The compound was prepared according to the procedure for Example 10 using Example 13 and 2-propyl bromide; 60 hr; preparative TLC (10% MeOH in $CH_2Cl_2$); yield 10%; MS: 465 m/e $(M+1)^+$.

Example 20

The compound was prepared according to the procedure for Example 6 using Example 13 and 2-cyclopropylmethyl bromide; 14 hr; preparative TLC (10% MeOH in $CH_2Cl_2$); yield 5%; MS: 477 m/e $(M+1)^+$.

Example 21

The compound was prepared according to the procedure for Example 6 using Example 13 and 2-cyclopropylmethyl bromide; 14 hr; preparative TLC (10% MeOH in $CH_2Cl_2$); MS: 507 m/e $(M+1)^+$.

Example 22

The compound was prepared according to the procedure for Example 6 using Example 13 and isobutyl bromide; preparative TLC (10% MeOH in $CH_2Cl_2$); MS: 493 m/e $(M+1)^+$.

Example 23

The compound was prepared according to the procedure for Example 6 using Example 17 and ethyl iodide; preparative TLC (10% MeOH in $CH_2Cl_2$); MS: 451 m/e $(M+1)^+$.

Example 24

The compound was prepared according to the procedure for Example 6 using Example 13 and 1-bromo-3,5-dimethoxytriazine; preparative TLC (10% MeOH in $CH_2Cl_2$); MS: 540 m/e $(M+1)^+$.

Example 25

To 25 mg (0.07 mmol) of the N-ethyl intermediate I-23-1 in methylene chloride/nitromethane (3 mL/2 mL) was slowly added 2-furoyl chloride (69 μl, 0.7 mmol, 10 eq) followed by aluminum chloride (93 mg, 0.7 mmol, 10 eq). The reaction mixture was stirred at room temperature overnight. The reaction mixture was concentrated, water and a few drops of 1N HCl were added to the residue and the mixture was extracted with methylene chloride. The combined organic extracts were dried with sodium sulfate, the drying agents removed by filtration, and the solvent was removed by evaporation. The crude mixture was dissolved in methanol/methylene chloride and purified by preparative TLC eluting with 10% methanol/methylene chloride. The desired band was collected, stirred with methylene chloride/methanol, filtered through a fritted funnel, and concentrated. The sample was dried at 80° C. under high vacuum overnight. MS m/e 451 (M+1).

Example 26

The compound was prepared by the method described for Example 25. MS m/e 438 (M+1).

Example 27

To the N-ethyl intermediate I-23-1 (25 mg, 0.07 mmol) in nitromethane (5 mL) was added 2-thiophene carbonyl chloride (75 μl 0.7 mmol, 10 eq) followed by addition of aluminum chloride (94 mg, 0.7 mmol, 10 eq) in small portions. The reaction mixture was stirred at room temperature overnight. The reaction was then concentrated, stirred with water and a few drops of 1 N HCl were added. The product was collected by filtration, dissolved in methylene chloride/methanol and purified by preparative TLC eluting with 10% methanol/methylene chloride. The desired band was collected, stirred with methylene chloride/methanol, filtered, and concentrated. The sample was dried at 80° C. under vacuum overnight. MS m/e 467 (M+1).

Examples 28–49 were prepared using the general method described for Example 27 using the appropriate N-alkyl intermediate 1–23, and heteroaryl acid chloride with $AlCl_3$ or $FeCl_3$ as catalyst.

Example 28

MS m/e 423 (M+1)

Example 29

MS m/e 465 (M+1)

Example 30

MS m/e 479 (M+1)

Example 31

MS m/e 495 (M+1)

Example 32

MS m/e 463 (M+1)

Example 33

MS m/e 509 (M+1)

Example 34

MS m/e 481 (M+1)

Example 35
MS m/e 530 (M+1)

Example 36
MS m/e 495 (M+1)

Example 37
MS m/e 479 (M+1)

Example 38
MS m/e 574 (M+1)

Example 39
MS m/e 481 (M+1)

Example 40
MS m/e 481 (M+1)

Example 41
MS m/e 608 (M+1)

Example 42
MS m/e 588 (M+1)

Example 43
MS m/e 536 (M+1)

Example 44
MS m/e 520 (M+1)

Example 45
MS m/e 509 (M+1)

Example 46
MS m/e 592 (M+1)

Example 47
MS m/e 550 (M+1)

Example 48
MS m/e 550 (M+1)

Example 49
MS m/e 570 (M+1)

Example 50

To a stirred solution of 3-amino intermediate I-29-2 (25 mg, 0.0649 mmol) in CH$_2$Cl$_2$ (5 mL) was added isopropyl chloroformate (1.0 M in toluene, 125 µL, 0.125 mmol) and pyridine (20 µL, 0.247 mmol). After stirring 3 h at room temperature, the resulting precipitate was filtered and dried to give 28 mg (91%) of the desired product. $^1$H NMR (DMSO-d$_6$) δ 9.51 (s, 1H), 8.85 (s, 1H), 8.36 (s, 1H), 8.08 (s, 1H), 7.61–7.49 (m, 2H), 4.98 (m, 1H), 4.68 (s, 2H), 4.51 (m, 2H), 3.86 (s, 3H), 3.45 (m, 2H), 2.83 (m, 2H), 1.80 (m, 2H), 1.29 (m, 6H), 0.89 (m, 3H); MS (m/e) 472 (M+1).

Example 51
MS m/e 458 (M+H).

Example 52
MS m/e 486 (M+H).

Example 53
MS m/e 472 (M+H).

Example 54
MS m/e 476 (M+H).

Example 55
MS m/e 492 (M+H).

Example 56
MS m/e 458 (M+H).

Example 57
MS m/e 500 (M+H).

Example 58
MS m/e 486 (M+H).

Example 59
MS m/e 486 (M+H).

Example 60
MS m/e 472 (M+H).

Example 61
MS m/e 472 (M+H).

Example 62
MS m/e 536 (M+H).

Example 63
MS m/e 490 (M+H).

Example 64
MS m/e 506 (M+H).

Example 65
MS m/e 550 (M+H).

Example 66
MS m/e 486 (M+H).

Example 68

To 25 mg (0.045 mmol) of the N-p-nitrophenyl intermediate was added 500 μl N-piperidinylethanol. The reaction was stirred at room temperature for approximately 5 hours, diluted with methylene chloride, washed with water/brine and dried over sodium sulfate. The crude product was purified by preparative TLC eluting with 8–10% MeOH/CH$_2$Cl$_2$. The pure product was collected, stirred with solvent, filtered, and concentrated. The sample was dried at 80° C. under high vacuum. $^1$H NMR (DMSO-d$_6$) δ 9.80 (s, 1H), 8.77 (s, 1H), 8.36 (s, 1H), 8.10 (s, 1H), 7.72 (d, 1H), 7.50 (d, 1H), 5.20 (m, 1H), 4.78 (s, 2H), 4.19 (m, 2H), 3.86 (s, 3H), 2.78 (m, 2H), 2.41 (m, 4H), 1.59 (d, 6H), 1.40 (m, 10H). MS m/e 541 (M+1).

Example 67

The compound was prepared by the method described for Example 68 using the N-p-nitrophenyl intermediate and N-pyrrolidinylethanol. MS m/e 527 (M+1).

Example 69

The compound was prepared by the method described for Example 68 using the N-p-nitrophenyl intermediate and N-pyrrolidinylethanol. MS m/e 538 (M+1).

Example 70

Step 1: O-Nitrophenylcarbonate intermediate: A mixture of the phenol intermediate I-33-1 (192 mg, 0.525 mmol) and p-nitrophenyl carbonate (314 mg, 1.03 mmol) in DMF (4 mL) was heated to 100° C. for 20 h. Solvent was removed by rotary evaporation and the residue was extracted into CH$_2$Cl$_2$ and washed with aqueous NaHCO$_3$. The organic layer was dried over MgSO$_4$, filtered, and evaporated. The resulting residue was purified by column chromatography (silica gel, 3% MeOH in CH$_2$Cl$_2$) to afford the carbonate intermediate (156 mg, 56%). $^1$H NMR (CDCl$_3$) δ 8.86 (s, 1H), 8.34 (d, 2H, J=9.1), 7.69 (d, 1H, J=2.1), 7.53 (d, 2H, J=9.1), 7.49, (d, 1H, J=8.8), 7.41, (d, 1H, J=8.8), 6.01 (s, 1H), 4.84 (s, 2H), 4.62 (q, 2H, J=7.1), 3.96 (s, 3H), 3.55 (t, 2H, 8.0), 3.01 (t, 2H, J=8.0), 1.55 (t, 3H, J=7.1). MS m/e 538 (M+H).

Step 2: A suspension of the carbonate intermediate (52 mg, 97 umol) in THF (2 mL) was treated with pyrrolidine (20 uL, 227 umol). The mixture was warmed to 40° C. for 2 h. Solvent was removed by rotary evaporation, and the residue was extracted into CH$_2$Cl$_2$ and washed with dilute aqueous NaOH. The organic layer was dried over MgSO$_4$, filtered, and evaporated. The resulting residue was purified by triturating with water (2×1 mL) and ether (2×1 mL). $^1$H NMR (CDCl$_3$, δ) 8.86 (s, 1H), 7.55 (d, 1H, J=2.1), 7.40, (d, 1H, J=8.8), 7.26, (d, 1H, J=8.8), 6.01 (s, 1H), 4.78 (s, 2H), 4.57 (q, 2H, J=7.1), 3.95 (s, 3H), 3.65 (t, 2H, 7.0), 3.55–3.45 (m, 4H), 2.99 (t, 2H, J=7.0), 2.02–1.96 (m, 4H), 1.53 (t, 3H, J=7.1). MS m/e 470 (M+H).

Example 71

MS m/e 498 (M+H).

Example 72

MS m/e 484 (M+H).

Example 73

MS m/e 555 (M+H).

Example 74

To 20 mg (0.052 mmol) of the amine intermediate I-29-1 in 2 mL CH$_2$Cl$_2$/12.6 μl pyridine was added 28 mg (0.156 mmol, 3 eq.) nicotinoyl chloride. The reaction was heated to 49° C. for 1 hr, cooled to room temperature, concentrated, stirred with ether, and the solid was filtered off. The solid was taken up in CH$_2$Cl$_2$/MeOH and purified on preparative TLC eluting with 10% MeOH/CH$_2$Cl$_2$. The pure product was collected and dried at 80° C. under high vacuum. $^1$H NMR (DMSO-d$_6$) 10.53 (s, 1H), 9.18 (s, 1H), 8.79 (s, 2H), 8.40 (m, 3H), 7.83 (s, 2H), 7.6 (m, 114), 5.25 (m, 1H), 4.74 (s, 2H), 3.87 (s, 3H), 3.41 (m, 2H), 2.80 (m, 2H), 1.61 (d, 6H). MS m/e 491(M+1).

Examples 75–82 were prepared by the method described for Example 74 using the appropriate amine intermediate I-29 and acid chloride.

Example 75

MS m/e 496 (M+H).

Example 76

MS m/e 480 (M+H).

Example 77

MS m/e 491 (M+H).

Example 78

MS m/e 491 (M+H).

Example 79

MS m/e 510 (M+H).

Example 80

MS m/e 494 (M+H).

Example 81

MS m/e 481 (M+H).

Example 82

MS m/e 495 (M+H).

Example 83

The compound was prepared using the N-sec-butyl intermediate I-36 and 2-thiophene carbonyl chloride by the general procedure described for Example 25. MS m/e 495 (M+H).

Example 84

The compound was prepared using the N-sec-butyl indazole intermediate I-36 and 2-furoyl chloride by the general procedure described for Example 25. MS m/e 479 (M+H).

Example 85

The compound was prepared using the intermediate I-39 by the general procedure described for Example 13. MS m/e 479 (M+H).

General Procedure A for Examples 136–140

A solution of diol intermediate I in the appropriate alcohol (0.05 M) in a sealable glass reaction tube was added camphorsulfonic acid (1.1 equiv.). The reaction tube was flushed with nitrogen and sealed. The reaction mixture was heated to 80° C. for 2–26 h and monitored for loss of starting material by HPLC. Upon completion of the reaction the mixture was cooled to room temperature and poured into ether. The precipitate that formed was collected by filtration and purified by flash chromatography or preparative TLC on silica gel using ethyl acetate or a mixture ethyl acetate and hexane to yield the pure products. The following Examples were prepared.

Example 136

Tan solid (58% yield). $^1$H NMR (CDCl$_3$, 300 MHz): δ 2.03 (m, 2H), 2.13 (m, 2H), 2.40 (m, 2H), 3.56 (m, 4H), 3.72 (m, 4H), 4.37 (s, 2H), 4.71 (s, 4H), 4.89 (s, 2H), 6.12 (s, 1H), 7.34–7.62 (6H, m), 7.99 (s, 1H), 9.53 (d, 1H); MS (ESI): m/e 510 (M+1)$^+$;

Example 137

(71% yield). $^1$H NMR (CDCl$_3$, 300 MHz): δ 1.97 (t, 2H), 3.61 (t, 2H), 3.79 (m, 4H), 4.14 (s, 2H), 4.41 (m, 4H), 4.62 (s, 2H), 4.76 (s, 2H), 6.10 (s, 1H), 7.28–7.57 (m, 11 H), 7.68 (s, 1H), 9.47 (d, 1H); MS (ESI): m/e 533 (M+1)+; 555 (M+Na)$^+$.

Example 138

(19% yield). $^1$H NMR (CDCl$_3$, 300 MHz): δ 1.66 (m, 1H), 2.01–2.22 (m, 3H), 2.67 (m, 1H), 3.51 (m, 2H), 3.74 (m, 4H), 3.88 (m, 2H), 4.38 (s, 2H), 4.71 (s, 2H), 4.72 (m, 2H), 4.90 (s, 2H), 6.07 (s, 1H), 7.36 (t, 1H), 7.44–7.68 (m, 5H), 7.80 (s, 1H), 9.53 (d, 1H); MS (ESI): m/e 483 (M+1)$^+$;

Example 139

(21.2 mg) $^1$H NMR (CDCl$_3$, 300 MHz): δ 1.95 (m, 2H), 2.04 (s, 3H), 2.68 (t, 2H), 3.49 (m, 2H), 3.64 (t, 2H), 4.52 (s, 2H), 4.66 (s, 2H), 4.73 (m, 2H), 4.90 (s, 2H), 7.27–7.43 (m, 2H), 7.48 (d, 1H), 7.63 (d, 1H), 7.69 (d, 1H), 7.94 (s, 1H), 8.55 (s, 1H), 9.46 (d, 1H); MS (ESI): m/e 473 (M+1)$^+$;

Example 140

Off-white solid (25% yield). $^1$H NMR (CDCl$_3$, 300 MHz): δ 1.93 (m, 2H), 3.22 (s, 3H), 3.46 (m, 4H), 3.58 (m, 2H), 4.49 (s, 2H), 4.64 (s, 2H), 4.70 (m, 2H), 4.78 (m, 1H), 4.87 (s, 2H), 7.23–7.43 (m, 2H), 7.47 (d, 1H), 7.62 (d, 1H), 7.70 (d, 1H), 7.89 (s, 1H), 8.54 (s, 1H), 9.46 (d, 1H);

General Procedure B Examples 141–144

In a sealed reaction tube, a suspension of the diol intermediate I (1 equivalent) in either the appropriate alcohol or methylene chloride or chloroform containing the appropriate alcohol, at room temperature was added trifluoroacetic anhydride (1–2 equiv.) slowly. The tube was flushed with nitrogen and sealed tightly. The mixture was stirred at room temperature for 1–2 hours then heated to 80° C. for 2–60 h and monitored for disappearance of starting material by HPLC. Upon completion the reaction was allowed to cool to room temperature, concentrated and worked up by both triturating the residue with ether and collecting the resulting precipitate by filtration, or extraction of the product from the reaction mixture with a suitable organic solvent. The solid product was purified by triturating with ether or flash chromatography on silica gel using ethyl acetate or a mixture of ethyl acetate and hexane. The following Examples were prepared.

Example 141

Light yellow solid (17% yield). $^1$H NMR (DMSO-d6, 300 MHz): δ 1.93 (m, 2H), 3.45 (m, 6H), 3.58 (s, 4H), 4.53 (s, 2H), 4.56 (m, 1H), 4.65 (s, 2H), 4.74 (m, 3H), 4.91 (s, 2H), 7.33–7.39 (m, 2H), 7.48 (d, 1H), 7.63–7.71 (m, 2H), 7.92 (s, 1H), 8.55 (s, 1H), 9.47 (d, 1H); MS (ESI): m/e 487 (M+1)$^+$, 509 (M+Na)$^+$.

Example 142

Pale yellow solid (26% yield). $^1$H NMR (CDCl$_3$, 300 MHz): δ1.33 (d, 3H), 2.11 (m, 2H), 3.19 (m, 1H), 3.56–3.77 (m, 4H), 4.30 (s, 2H), 4.65 (m, 2H), 4.68 (s, 2H), 4.74 (s, 2H), 6.07 (s, 1H), 7.20–7.50 (m, 1H), 7.56 (d, 1H), 7.69 (s, 1H), 9.48 (d, 1H); MS (ESI): m/e 517 (M+1)$^+$, 539 (M+Na)$^+$.

Example 143

Orange residue (21% yield). $^1$H NMR (DMSO-d6, 300 MHz): δ 1.93 (m, 2H), 2.30 (m, 4H), 2.50 (m, 2H), 3.48 (m, 6H), 3.94 (s, 2H), 4.52 (s, 2H), 4.72 (m, 4H), 4.88 (s, 2H), 7.33–7.43 (m, 2H), 7.48 (d, 1H), 7.66 (m, 2H), 7.88 (s, 1H), 8.57 (s, 1H), 9.46 (d, 1H); MS (ESI): m/e 528 (M+1)$^+$.

Example 144

Light orange solid (9% yield). $^1$H NMR (DMSO-d6, 300 MHz): δ 1.29 (m, 2H), 1.39 (m, 4H), 1.95 (m, 2H), 2.26 (m, 4H), 2.51 (m, 2H), 3.47 (m, 2H), 3.94 (s, 2H), 4.52 (s, 2H), 4.72 (m, 4H), 4.88 (s, 2H), 7.33–7.39 (m, 2H), 7.47 (d, 1H), 7.66 (m, 2H), 7.88 (s, 1H), 8.57 (s, 1H), 9.46 (d, 1H); MS (ESI): m/e 526 (M+1)$^+$.

General Procedure C for Examples 145–156

To a well-stirred suspension of the CH$_2$OH intermediates I, II, or III in 7 mL of methylene chloride were added sequentially trifluoroacetic anhydride (5 equivalents) and N-methyl morpholine (5 eq) at 5° C. and under argon atmosphere. The resulted suspension was stirred at room temperature for 3 hours and the low boiling solvents were removed under vacuum. A stirred solution of this tritrifluoroacetate intermediate in an appropriate alcohol was heated to 80° C. for 6–48 hours in an oil bath. Gradually, the heterogeneous reaction mixture became homogeneous. When no starting material was observed by HPLC the reaction mixture was worked up by removing the solvent in vacuo. The residues was purified by either triturating with water or ether or alternatively, flash chromatography or preparative plate chromatography on silica gel using ethyl acetate or an ethyl acetate/hexane mixture.

Example 145

(12.6 mg, 44% yield). $^1$H NMR (CDCl$_3$, 300 MHz): δ 2.18 (m, 2H), 2.09 (m, 1H), 3.73 (m, 4H), 4.42 (s, 2H), 4.76 (s, 2H), 4.80 (m, 2H), 4.98 (s, 2H), 6.12 (s, 1H), 7.23 (m, 2H), 7.43 (m, 2H), 7.48 (m, 2H), 7.68 (m, 1H), 7.88 (s, 1H), 9.56 (d, 1H); MS (ESI): m/e 451 (M+1)$^+$, 473 (M+Na)$^+$.

Example 146

Light orange solid (35.3 mg, 74% yield). $^1$H NMR (DMSO-d6, 300 MHz): δ 1.23 (m, 2H), 1.50 (m, 4H), 1.67 (m, 2H), 1.93 (m, 2H), 2.13 (m, 1H), 3.35 (m, 2H), 3.48 (m, 2H), 4.52 (s, 2H), 4.62 (s, 2H), 4.72 (m, 2H), 4.89 (s, 2H), 7.33–7.39 (m, 2H), 7.47 (d, 1H), 7.62–7.70 (m, 2H), 7.90 (d, 1H), 8.53 (s, 1H), 9.47 (d, 1H); MS (ESI): m/e 481 (M+1)$^+$.

Example 147

Pale yellow solid (31 mg, 54% yield). $^1$H NMR (DMSO-d6, 300 MHz): δ 0.05 (m, 2H), 0.49 (m, 2H), 1.06 (m, 1H), 2.79 (m, 2H), 3.82 (m, 5H), 4.65 (m, 4H), 4.79 (s, 2H), 4.97 (t, 1H), 6.80 (d, 1H), 6.89 (s, 1H), 7.46 (d, 1H), 7.65 (d, 1H), 7.87 (s, 1H), 7.89 (d, 1H), 8.36 (s, 1H); MS (ESI): m/e 483 (M+1)$^+$.

Example 148

Pale orange solid (12.4 mg, 24% yield). $^1$H NMR (DMSO-d6, 300 MHz): δ 2.79 (m, 2H), 3.12 (t, 2H), 3.30 (m, 2H), 3.72 (t, 2H), 3.82 (m, 5H), 4.65 (m, 2H), 4.70 (s, 2H), 4.76 (s, 2H), 4.97 (t, 2H), 6.79 (d, 1H), 6.90 (s, 1H), 6.93 (s, 1H), 6.97 (d, 2H), 7.35 (s, 1H), 7.46 (d, 1H), 7.65 (d, 1H), 7.89 (d, 2H), 8.39 (s, 1H); MS (ESI): m/e 539 (M+1)$^+$.

Example 149

Pale yellow solid (42.6 mg, 57% yield). $^1$H NMR (DMSO-d6, 300 MHz): δ 2.55 (m, 2H), 2.80 (t, 2H), 3.86 (m, 4H), 3.98 (s, 2H), 4.61 (s, 1H), 4.73 (t, 1H), 4.80 (s, 2H), 4.98 (t, 1H), 6.78 (d, 1H), 6.89 (s, 1H), 7.50 (d, 1H), 7.68 (d, 1H), 7.88 (s, 1H), 7.90 (d, 1H), 8.38 (s, 1H); MS (ESI): m/e 489 (M+1)$^+$, 512 (M+Na)$^+$.

Example 150

Yellow-tan solid (77% yield). $^1$H NMR (DMSO-d6, 300 MHz): δ 0.2 (m, 2H), 0.47 (m, 2H), 1.05 (m, 1H), 1.94 (m, 2H), 3.49 (m, 2H), 4.53 (s, 2H), 4.64 (s, 2H), 4.75 (m, 2H), 4.92 (s, 2H), 7.32–7.45 (m, 2H), 7.49 (d, 1H), 7.62–7.77 (m, 2H), 7.93 (s, 1H), 8.64 (s, 1H), 9.47 (d, 1H); MS (ESI): m/e 453 (M+1)$^+$.

Example 151

Tan solid (32% yield). $^1$H NMR (DMSO-d6, 300 MHz): δ 1.97 (m, 4H), 3.51 (s, 2H), 3.73 (t, 2H), 4.56 (s, 2H), 4.71 (s, 2H), 4.77 (m, 2H), 4.91 (s, 2H), 6.98 (m, 2H), 7.35–7.43 (m, 3H), 7.52 (d, 1H), 7.70 (m, 2H), 7.96 (s, 1H), 8.60 (s, 1H), 9.51 (d, 1H); MS (ESI): m/e 509 (M+1)$^+$.

Example 152

Yellow solid (69%). $^1$H NMR (DMSO-d6, 300 MHz): δ 1.62–2.00 (m, 8H), 2.54 (m, 1H), 3.38–3.50 (m, 4H), 4.51 (s, 2H), 4.61 (s, 2H), 4.72 (m, 2H), 4.89 (s, 2H), 7.3–7.41 (m, 2H), 7.46 (d, 1H), 7.62–7.70 (m, 2H), 7.89 (s, 1H), 8.53 (s, 1H), 9.47 (d, 1H); MS (ESI): m/e 467 (M+1)$^+$.

Example 153

(80%) $^1$H NMR (DMSO-d6, 300 MHz): δ 1.55 (m, 3H), 3.4–3.8 (m, 6H), 4.14 (m, 2H), 4.66 (s, 2H), 4.91 (s, 2H), 7.29–7.73 (m, 5H), 7.98 (s, 1H), 8.55 (s, 1H), 9.39 (d, 1H), 11.94 (s, 1H).

Example 154

(150 mg, 89% yield). $^1$H NMR (DMSO-d6, 300 MHz): δ 1.80 (m, 4H), 3.58–3.78 (m, 4H), 4.02 (m, 1H), 4.18 (s, 2H), 4.69 (s, 2H), 4.93 (s, 2H), 7.43–7.49 (m, 2H), 7.56 (t, 2H), 7.70 (d, 1H), 7.94 (s, 1H), 8.53 (s, 1H), 9.39 (d, 1H), 11.92 (s, 1H).

Example 155

$^1$H NMR (DMSO-d6, 300 MHz): δ 3.24 (s, 3H), 3.47 (m, 2H), 3.58 (m, 2H), 4.13 (m, 2H), 4.62 (s, 2H), 4.89 (s, 2H), 7.30–7.42 (m, 3H), 7.56 (d, 1H), 7.64 (d, 1H), 7.91 (s, 1H), 8.51 (s, 1H), 9.35 (d, 1H), 11.89 (s, 1H); MS (ESI): m/e 421 (M+Na)$^+$.

Example 156

(10%). MS m/e 429 (M+1); $^1$H-NMR δ (DMSO-d$_6$) 11.79 (s, 1H), 9.20 (d, 1H), 8.44 (s, 1H), 7.87 (s, 1H), 7.52 (d, 1H), 7.38 (d, 1H), 7.24 (s, 1H), 6.96 (d, 1H), 4.86 (s, 2H), 4.61 (s, 2H), 4.08 (s, 2H), 3.81 (s, 4H), 3.58 (d, 1H), 3.52 (d, 1H).

Example 157

A stirred solution of Example 155 (370 mg, 0.93 mmol) in DMF (20 mL) was placed under vacuum and DMF (10 mL) was removed by distillation. The mixture was cooled to room temperature and sodium hydride (45 mg, 0.93 mmol) was added and stirred for 30 min. Glycidol mesylate (170 mg, 1.1 mmol) was added and the reaction mixture heated to 60° C. After 18 h, the mixture was cooled to room temperature, filtered, and concentrated in vacuo. The solid was triturated with methanol, filtered, and purified by flash chromatography on silica gel using hexane/ ethyl acetate (1:1) then methanol/ethyl acetate (10%) to give product (90 mg, 22% yield). MS (ESI): m/e 455 (M+1)$^+$.

Example 158

To a stirred solution of Example 157 (80 mg, 0.18 mmol) in THF (10 mL) was added super hydride (724 uL, 0.72 mmol) dropwise at 0° C. The reaction mixture was warmed to room temperature and stirred for 2 h. The reaction solvent was removed in vacuo and 1N HCl was added. The mixture was stirred, filtered, triturated with methanol and collected by filtration. The solid was purified by flash chromatography using hexane/ethyl acetate (3:1) to ethyl acetate (100%). Further purification of the solid involved crystallization from ethyl acetate/methanol followed by acetonitrile to give product (40 mg, 50% yield). MS (ESI): m/e 457 (M+1)$^+$.

Example 159

Using the general procedure for Example 158, a suspension of ester (1.45 g, 2.27 mmol) in methylene chloride (30 mL) was cooled to 0° C. and DIBAL-H (5.7 mL, 5.7 mmol)

was added dropwise. The reaction mixture was warmed to room temperature for 2 h then quenched with methanol (20 mL). HCl (1N, 20 mL) was added and the reaction solvent removed in vacuo to give the product as a yellow solid (1.2 g, 78% yield). Alcohol (522 mg, 0.92 mmol), trifluoroacetic anhydride (130 uL), methoxyethanol (4 mL) and methylene chloride (6 mL) were combined and heated to 70° C. for 18 h. Additional trifluoroacetic anhydride (100 ul) was added and heated for 24 h. The reaction solvent was removed in vacuo and the solid triturated with methanol to give the product as a yellow solid (325 mg, 91% yield). A solution of the previous product (100 mg, 0.16 mmol) in methylene chloride (3 mL)/methanol (1 mL)/hexamethylphosphoramide (500 uL) was added cesium carbonate (212 mg, 0.65 mmol). The reaction mixture was stirred at room temperature for 20 min. and acetaldehyde was added and the mixture was stirred for 18 h. Additional cesium carbonate and acetaldehyde was added and the mixture stirred for 3 h. The mixture was diluted with methylene chloride, washed with water and brine, and purified by flash chromatography on silica gel using ethyl acetate/methylene chloride (10%) to give product (45 mg, 43% yield). The product (45 mg) was dissolved in methylene chloride (4 mL) and ethanethiol followed by trifluoroacetic anhydride was added at 0° C. After 1.5 h, the reaction solvent was removed in vacuo and the material purified by flash chromatography on silica gel using methanol/ethyl acetate (10%) to give product (11 mg, 37% yield). MS (ESI): m/e 443 (M+1)$^+$.

Example 160

To the tritrifluoroacetate (27 mg) prepared using general method C was added 1 mL 2-methoxyethanol and the reaction was heated to 90° C. in a sealed tube for 2 hours. The reaction was concentrated, the product triturated with ether, collected and dried. $^1$HNMR(400 MHz, DMSO) δ 8.38(1H, s), 7.89 (2H, d), 7.66 (1H, d), 7.47(1H, d), 6.90(1H, s), 6.81(1H, d), 4.98(2H, m), 4.79(1H, s), 4.67(3H, m), 3.96(6H, m), 3.82((2H, m), 3.62 (2H, m), 3.50(3H, m), 3.10(2H, m), 2.79(2H, m) MS m/e 487 (M+1)$^+$ Example 161

To the amino methyl intermediate XII CEP7668 (30 mg, 0.066 mmol) in THF (1 mL) was added TEA (9 μl, 0.066 mmol), followed by benzyl chloroformate (9 μl, 0.066 mmol) and the reaction mixture was stirred at room temperature overnight. Additional TEA and benzyl chloroformate were added while heating to 50° C. The reaction was concentrated, dissolved in ethyl acetated, washed with sodium bicarbonate, brine and dried over magnesium sulfate. The drying agent was removed by filtration and the solvent evaporated. The product was purified by preparative TLC using 2% methanol/methylene chloride. The product was collected and dried at 80° C. overnight. MS m/e=590 (m+1)$^+$.

Example 162

This compound was prepared using the general procedure as Example 161 starting with 3-aminomethyl-N-ethanol intermediate XIII MS m/e 540 (m+1)$^+$.

Example 163

This compound was prepared from XII intermediate and ethyl isocyanato acetate. MS m/e 513 (m+1)$^+$.

Example 164

Phenol intermediate X CEP 7143 (15 mg, 0.037 mmol), bromoethylethylether (66 mg., 0.57 mmol) (added in 3 portions), acetone (7 mL) and 10N sodium hydroxide (4 mL) were stirred at room temperature for 7 hr. The acetone was evaporated and the solution acidified to pH 3. The solid was collected, triturated with hexane and then extracted with methylene chloride. The extract was evaporated to give the product (0.004 g.) (23%) MS m/e 471 (M+1); $^1$H-NMR (DMSO-d$_6$) 11.40 (s, 1H), 8.33 (s, 1H), 8.16 (d, 1H), 7.47 (d, 2H), 7.11 (d, 1H), 6.86 (s, 1H), 6.78 (d, 1H), 4.80 (s, 2H), 4.69 (m, 1H), 4.24 (m, 2H), 3.85 (m, 2H), 3.65 (t, 2H), 2.98 (t, 2H), 2.81 (t, 2H), 1.30 (d, 6H), 1.23 (t, 3H).

Example 165

A mixture of intermediate X (16.5 mg, 0.041 mmol) and cesium carbonate (88 mg, 1.1 eq) in 2.0 mL of CH$_3$CN was added cyclopentyl bromide (8.0 ul, 2.0 eq.) under N$_2$. After stirred at 70° C. for 24 hours, the mixture was diluted with CH$_2$Cl$_2$ and filtered through celite and concentrated. Purification by preparation TLC plate with CH$_2$Cl$_2$/MeOH afforded the product. MS m/e 533 (M+1).

Example 166

Prepared by hydrogenation of Example 1C in DMF using Pd(OH)$_2$ and a drop of HCl. MS m/e 443 (M+1)

Example 1C

A suspension of sodium hydride (2.44 mg, 1.22 eq.) in 0.5 mL of THF was stirred under N$_2$ as phenol intermediate X (3-hydroxy-10-isopropoxy-12,13-dihydro-6H,7H,14H-nephthyl(3,4-a)pyrrolo(3,3-a)pyrrolo(3,4-c)carbazole-7 (7H)one) (20.6 mg, 0.05 mmol) in 2.0 mL of THF:DMF (1:1) was added dropwise. After 10 minutes of stirring, 2-bromopyrimidine (8.9 mg, 1.12 eq.) in 0.5 mL of THF was added. The mixture was stirred at 60° C. for 14 hours. Then, the mixture was cooled to room temperature, diluted with CH$_2$Cl$_2$/MeOH, filtered through celite and concentrated. Purification was achieved by preparation TLC plate with CH$_2$Cl$_2$/MeOH (9:1) to afford the product (4.0 mg, 17%) (MS: 477 m/z (M+H)$^+$).

General Methods for Synthesis of Examples 167–191

Method A: A mixture of hydroxyl intermediate (0.2 mmol), potassium iodide (3.3 mg, 0.1 eq.), N-tetrabutylammonium bromide (0.1 eq), cesium hydroxide hydrate (3 eq) and 20 mg of 4 Å sieves in 2.0 mL of CH$_3$CN was added the appropriate alkyl bromide or iodide under N$_2$. After the mixture was stirred at 50° C. for 14–72 hours, the reaction mixture was diluted with CH$_3$CN and filtered through celite and concentrated. The residue was diluted with CH$_2$Cl$_2$ and washed with water and dried over magnesium sulfate. Purification by preparation TLC plate or crystallization with CH$_2$Cl$_2$/MeOH afforded the desired products.

Method B: A mixture of hydroxy intermediate (0.2 mmol) and cesium carbonate (3 eq) in 2.0 mL of CH$_3$CN was added the appropriate alkyl bromide or iodide under N$_2$. After the mixture was stirred at 50–80° C. for 14–72 hours, the reaction mixture was diluted with CH$_3$CN and filtered through celite and concentrated. The residue was diluted with CH$_2$Cl$_2$ and washed with water and dried over magnesium sulfate. Purification by preparation TLC plate or crystallization with $CH_2Cl_2$/MeOH afforded the desired product.

Method C: A mixture of hydroxyl intermediate (0.1 mmol), sodium hydroxide (1.5 eq.) and N-tetrabutylammonium bromide (0.1 eq) in 0.5 mL of $CH_2Cl_2$ and 0.5 mL of water was added the appropriate alkyl bromide under $N_2$. After the mixture was stirred at room temperature for 14–72 hours, the reaction mixture was concentrated and the residue was washed with water and dried over magnesium sulfate. Purification by preparation TLC plate with $CH_2Cl_2$/MeOH or crystallization afforded the desired product.

Example 167

A mixture of intermediate phenol XV (19.5 mg, 0.05 mmol), potassium carbonate (34.6 mg, 5 eq.) and potassium iodide (8.7 mg, 1.05 eq) in 1.5 mL of acetone and 0.25 mL of DMF was added the benzyl 2-bromoethyl ether (8.3 uL, 1.05 eq.) under $N_2$. After the mixture was stirred at reflux for 24 hours, the reaction mixture was diluted with EtOAc and washed with water, saturated NaCl solution and dried over magnesium sulfate. Purification by preparation TLC plate with 5% of MeOH/$CH_2Cl_2$ afforded the desired product (10 mg, 39%). MS m/e 519 m/z $(M+1)^+$.

Example 168

The product was obtained by first forming compound 168I by Method A, using phenol XV and cyclopentyl bromide; 14 hr; prep. TLC (10% MeOH in $CH_2Cl_2$); yield 10%; MS: m/e 453 m/z $(M+1)^+$. A mixture of compound 168I 110 (5 mg, 0.01 mmol), 10% $Pd(OH)_2$/C and 0.1 mL of conc. HCl in 1.0 mL of EtOH was hydrogenated under 42 psi $H_2$ on a Parr apparatus for 24 hours at room temperature. Filtration and concentration afforded 2.2 mg (27%) of the title compound. MS: m/e 451 m/z $(M+1)^+$.

Example 169

Method C from phenol XV and epibromohydrin; 22 hour, preparative TLC (10% MeOH in $CH_2Cl_2$); yield 30%; MS: m/e 463 m/z $(M+Na)^+$.

Example 170.

Method C; phenol XV and 1-bromo-2-(2-methoxyethoxy)ethane, 14 hr; prep. TLC (10% MeOH in $CH_2Cl_2$); yield 11%; MS: 509 m/z $(M+Na)^+$.

Example 171

Method B; phenol XV and 2-(2-bromoethyl)-1,3-dioxane, 14 hr reflux; prep. TLC (10% MeOH in $CH_2Cl_2$); yield 54%; MS: 521 m/z $(M+1)^+$.

Example 172

Method A; phenol XV and (bromomethyl)cyclopropane, 14 hr; prep. TLC (10% MeOH in $CH_2Cl_2$); yield 17%; MS: m/e 439 m/z $(M+1)^+$.

Example 173

Method A; phenol XV and 2-bromomethyl-1,3-dioxolane; 64 hr; prep. TLC (10% MeOH in $CH_2Cl_2$); yield 15%; MS: 471 m/z $(M+1)^+$.

Example 174

Method B; phenol XV and N-(3-bromopropyl)phthalimide; 48 hr at 80° C.; prep. TLC (10% MeOH in $CH_2Cl_2$); yield 17%; MS: m/e 494 m/z $(M+Na)^+$.

Example 175

Method B; phenol XV and ethyl 2-bromopropionate; 14 hr at 80° C.; prep. TLC (10% MeOH in $CH_2Cl_2$); yield 9%; MS: m/e 507 m/z $(M+Na)^+$.

Example 176

Method A; phenol XV and methyl 4-chloro-3-methoxy-(E)-2-butenoate; 40 hr at 80° C.; prep. TLC (10% MeOH in $CH_2Cl_2$); yield 21%; MS: m/e 535 m/z $(M+Na)^+$.

Example 177

Method A; phenol XV and 1-bromopinacolone; 14 hr at 60° C.; prep. TLC (10% MeOH in $CH_2Cl_2$); yield 29%; MS: m/e 505 m/z $(M+Na)^+$.

Example 178

Method A; 20 hr at 50° C.; prep. TLC (10% MeOH in $CH_2Cl_2$); yield (5%); MS: 449 m/z $(M+Na)^+$.

Example 179

Method B. (38%) MS m/e 471 (M+1); $^1$H-NMR (DMSO-$d_6$) 8.37 (s, 1H), 7.90 (d, 1H), 7.83 (d, 1H), 7.64 (d, 1H), 7.46 (t, 1H), 7.25 (t, 1H), 6.86 (s, 1H), 6.75 (d, 1H), 4.97 (t, 1H), 4.77 (d, 4H), 4.60 (t, 2H), 4.16 (m, 2H), 3.78 (m, 2H), 2.45 (s, 2H), 1.21 (t, 3H).

Example 180

Method B (19%) MS m/e 476 (M+1); $^1$H-NMR (DMSO-$d_6$) 8.56 (s, 1H), 8.36 (s, 1H), 7.92 (d, 1H), 7.85 (m, 2H), 7.66 (d, 1H), 7.51 (d, 2H), 7.48 (t, 1H), 7.33 (m, 1H), 7.27 (t, 1H), 6.97 (s, 1H), 6.85 (d, 1H), 5.20 (s, 1H), 4.97 (m, 1H), 4.75 (s, 2H), 4.62 (m, 2H).

Example 181

Method B (43%) MS m/e 443 (M+1); $^1$H-NMR (DMSO-$d_6$) 8.36 (s, 1H), 7.90 (d, 1h), 7.83 (d, 1H), 7.64 (d, 1H), 7.45 (t, 1H), 7.24 (t, 1H), 6.87 (s, 1H), 6.77 (d, 1H), 4.97 (t, 1H), 4.75 (s, 2H), 4.61 (s, 2H), 4.11 (s, 2H), 3.77 (d, 2H), 3.65 (s, 2H), 2.73 (s, 2H).

Example 182

Method B (63%) M S m/e 452 (M+1); $^1$H-NMR (DMSO-$d_6$) 8.36 (s, 1H), 7.90 (d, 1H), 7.83 (d, 1H), 7.65 (d, 1H), 7.46 (t, 1H), 7.24 (t, 1H), 6.88 (s, 1H), 6.78 (d, 1H), 4.96 (t, 1H), 4.75 (s, 2H), 4.60 (m, 2H), 4.07 (t, 2H), 3.78 (m, 2H), 2.74 (m, 2H), 2.64 (t, 2H), 2.02 (m, 2H).

Example 183

Method B (72%) M S m/e 480 (M+1); $^1$H-NMR (DMSO-$d_6$) 8.35 (s, 1H), 7.91 (d, 1H), 7.82 (d, 1H), 7.64 (d, 1H), 6.85 (t, 1H), 6.76 (t, 1H), 4.96 (t, 1H), 4.75 (s, 2H), 4.60 (s, 2H), 4.00 (t, 2H), 3.77 (d, 2H), 2.73 (m, 2H), 1.73 (t, 3H), 1.52 (m, 8H), Example 184

Method B (67%) MS m/e 456 (M+1); $^1$H-NMR (DMSO-$d_6$) 8.35 (s, 1H), 7.91 (d, 1H), 7.83 (d, 1H), 7.64 (d, 1H), 7.46 (t, 1H), 7.24 (t, 1H), 6.87 (s, 1H), 6.75 (d, 1H), 4.96 (t, 1H), 4.75 (s, 2H), 4.60 (t, 2H), 4.10 (s, 2H), 3.78 (m, 2H), 3.70 (s, 2H), 3.00 (m, 2H), 2.70 (m, 2H), 1.11 (T, 3h).

Example 185

Method B (88%) M S m/e 466 (M+1); $^1$H-NMR (DMSO-$d_6$) 8.35 (s, 1H), 7.91 (d, 1H), 7.83 (d, 1H), 7.64 (d, 1H), 7.46 (t, 1H), 7.24 (t, 1H), 6.86 (s, 1H), 6.77 (d, 1H), 4.96 (t, 1H), 4.75 (s, 2H), 4.61 (m, 2H), 4.03 (t, 2H), 3.78 (m, 2H), 2.74 (m, 2H), 2.54), (t, 2H), 1.73 (m, 6H).

Example 186

Method B. MS m/e 516 (M+1); $^1$H-NMR (DMSO-$d_6$) 8.35 (s, 1H), 7.90 (d, 1H), 7.81 (d, 1H), 7.64 (d, 1H), 7.46 (t, 1H), 7.24 (t, 1H), 6.85 (s, 1H), 6.76 (d, 1H), 4.96 (t, 1H), 4.75 (s, 2H), 4.60 (t, 2H), 3.99 (t, 2H), 3.78 (m, 2H), 2.74 (m, 2H), 1.71 (m, 2H), 1.56 (t, 4H), 1.42 (m, 6H).

Example 187

Method B. MS m/e 438 (M+1).

Example 188

This compound was formed from Example 185B, ethanol and gaseous hydrogen chloride (85%) MS m/e 512 (M+1); $^1$H-NMR (DMSO-$d_6$) 8.35 (s, 1H), 7.91 (s, 1H), 7.83 (d, 1H), 7.65 (d, 1H), 7.46 (t, 1H), 7.26 (t, 1H), 6.85 (s, 1H), 6.76 (d, 1H), 4.75 (s, 1H), 4.61 (m, 2H), 4.35 (m, 2H), 4.00 (m, 2H), 3.79 (m, 2H), 2.73 (m, 2H), 2.66 (m, 2H), 1.77 (m, 6H), 1.33 (t, 3H).

Example 189

Example 188 was refluxed in ethanol and concentrated hydrochloric acid for 18 hr. The solution was made basic with sodium hydroxide to pH 10 and refluxed 4 hours. The solution was acidified to precipitate the product. MS m/e 485 (M+1); $^1$H-NMR (DMSO-$d_6$) 12.00 (s, 1H), 7.91 (d, 1H), 7.82 (d, 1H), 7.65 (d, 1H), 7.45 (t, 1H), 7.24 (m, 2H), 6.85 (s, 1H), 6.76 (d, 2H), 4.96 (t, 1H), 4.75(s, 2H), 4.61 (m, 2H), 3.98 (t, 1H), 3.77 (m, 2H), 2.73(m, 2H), 2.23 (m, 4H), 1.71(m, 8H).

Example 190

The product was obtained from a reaction of Example 186 with ethanol and gaseous hydrogen chloride (45%) MS m/e 512 (M+1); $^1$H-NMR (DMSO-$d_6$) 8.37 (s, 1H), 7.91 (d, 1H), 7.82 (d, 1H), 7.65 (d, 1H), 7.47 (t, 1H), 7.23 (m, 2H), 6.86 (s, 1H), 6.77 (d, 2H), 6.67 (s, 1H), 4.99 (t, 1H), 4.76 (s, 2H), 4.61 (m, 2H), 3.98 (t, 1H), 3.80 (m, 2H), 2.74 (m, 2H), 2.02 (t, 2H), 1.71 (m, 2H), 1.38 (m, 8H).

Synthesis of intermediate phenol XVII CEP 5108: To aluminum trichloride (1.2 g, 9 mmol) in 12 mL anhydrous dichloroethane was added 2 mL ethanethiol followed by methoxy derivative CEP 3371 (500 mg, 1.47 mmol). The mixture was stirred at 50° C. for 48 h. The reaction was concentrated and stirred with 10 mL 1N hydrochloric acid for thirty minutes. The product was isolated by filtration and was dried in vacuo to afford 483 mg (quantitative) of a grey solid, the phenol. NMR ($d_6$-DMSO): 11.8 (s, 1H), 9.53 (s, 1H), 9.2 (d, 1H), 8.45 (s, 1H), 7.95 (s, 1H), 7.6 (d, 1H), 7.45 (dd, 1H), 7.25 (dd, 1H), 7.08 (s, 1H), 6.8 (dd, 1H), 4.85 (s, 2H), 4.08 (s, 2H). MS (ES+): 327 (M+1).

Example 191 and Example 192

Phenol intermediate XVII (25 mg, 79 µmole), potassium carbonate (17 mg, 123 µmole), and ethyl bromoacetate (17 µL, 155 µmole) were combined in 10 mL dry acetone. A drop of N,N-dimethylformamide was and the mixture was heated at 50° C. for three days. HPLC analysis revealed the presence of two products. The two products were separated employing reverse phase C8 high performance liquid chromatography (1:1 acetonitrile:water with 0.1% trifluoroacetic acid). The first product eluted was identified as the mono adduct Example 191B. 2 mg. NMR ($d_6$-DMSO): 11.7 (s, 1H), 9.25 (d, 1H), 8.5 (s, 1H), 7.95 (d, 1H), 7.60 (d, 1H), 7.45 (dd, 1H), 7.25–7.3 (m, 2H), 7.0 (dd, 1H), 4.93 (s, 2H), 4.85 (s, 2H), 4.22 (q, 2H), 4.15 (s, 2H), 1.20 (t, 3H). MS (ES+): 435 (M+Na). Retention time: 13.03 min (gradient elution 10%–95% acetonitrile:water (0.1% trifluoroacetic acid) at 1.6 mL/min on a Zorbax RX-C8 4.6 by 150 mm column). The second product eluted was identified as the bis adduct Example 192B. NMR ($d_6$-DMSO): 8.3 (d, 1H), 8.06 (s, 1H), 7.96 (d, 1H), 7.72 (d, 1H), 7.45 (dd, 1H), 7.27 (dd, 1H), 7.20 (br s, 1H), 6.95 (dd, 1H), 5.6 (s, 2H), 5.42 (s, 2H), 5.35 (s, 2H), 4.25 (s, 2H), 4.18 (q, 2H), 3.75 (q, 2H), 1.2 (m, 6H). 2 mg. MS (ES+): 521 (M+Na).

Example 193

Prepared by the method described for Example 192 from bromoacetonitrile: NMR ($d_6$-DMSO): 11.85 (s, 1H), 9.3 (d, 1H), 8.48 (s, 1H), 7.95 (d, 1H), 7.58 (d, 1H), 7.4 (m, 2H), 7.2 (dd, 1H), 7.1 (d, 1H), 5.2 (s, 2H), 4.85 (s, 2H), 4.18 (s, 2H). MS(ES+): 366 (M+1).

Example 194

Example 192 (10 mg, 24 µmol) in 10 mL dry tetrahydrofuran was treated with lithium borohydride (0.5 mL of a 2.0 M solution in tetrahydrofuran, 1.0 mmol) and heated at 40° C. for 72 h. 1 mL water was then added and the solution was concentrated. The crude solid was taken up into 1 mL DMF and concentrated onto 600 mg silica. The silica was applied to the top of a bed of silica and medium pressure liquid chromatography was effected eluting with 4% methanol: dichloromethane to afford 3.0 mg of a tan solid. NMR ($d_6$-DMSO): 11.8 (s, 1H), 9.2 (d, 1H), 8.45 (s, 1H), 7.92 (d, 1H), 7.55 (d, 1H), 7.41 (dd, 1H), 7.25 (m, 2H), 6.95 (dd, 1H), 4.85 (s, 2H), 4.08 (s, 2H), 4.06 (m, 2H), 3.75 (m, 2H), 3.56 (t, 1H). MS (ES+): 371 (M+1).

Example 195

This compound was prepared by the method described for Example 194 from Example 193: NMR ($d_6$-DMSO): 9.3 (d, 1H), 8.48 (s, 1H), 7.95 (d, 1H), 7.70 (d, 1H), 7.45 (dd, 1H), 7.28 (m, 1H), 7.22 (s, 1H), 6.95 (d, 1H), 4.9 (s, 2H), 4.7 (br s, 2H), 4.46 (s, 2H), 4.06 (br s, 2H), 3.80 (br s, 2H), 3.70 (br s, 2H), 3.52 (overlapping s, 2H). MS (ES+): 415 (M+1).

Example 196

The O-allyl intermediate was prepared using allyl bromide as described for Example 194: NMR (d$_6$-DMSO): 11.8 (s, 1H), 9.27 (d, 1H), 8.48 (s, 1H), 7.98 (d, 1H), 7.60 (d, 1H), 7.45 (dd, 1H), 7.30 (s, 1H), 7.25 (m, 1H), 7.05 (dd, 1H), 6.10 (m, 1H), 5.4 (dd, 1H), 5.3 (dd, 1H), 4.95 (s, 2H), 4.7 (d, 2H), 4.18 (s, 2H). MS (ES+): 367 (M+1). Intermediate O-allyl (20 mg, 55 μmol), osmium tetroxide (0.1 mL of a 25 mg/mL solution in carbon tetrachloride), N-methylmorpholine-N-oxide (50 mg) were combined in 10 mL tetrahydrofuran to which was added 0.1 mL water. The mixture was stirred in the dark for 48 h. The mixture was concentrated onto 0.6 g silica and applied to a bed of silica. Medium pressure liquid chromatography eluting with 5% methanol:dichloromethane afforded 23 mg of a yellow solid. NMR (d$_6$ DMSO): 11.8 (s, 1H), 9.23 (d, 1H), 8.43 (s, 1H), 7.92 (d, 1H), 7.55 (d, 1H), 7.40 (dd, 1H), 7.25 (s, 1H), 7.22 (m, 1H), 6.95 (d, 1H), 4.95 (d, 1H), 4.88 (s, 2H), 7.70 (dd, 1H), 4.10 (s, 2H), 4.05 (d, 1H), 3.7–3.95 (m, 4H). MS (ES+): 401 (M+1).

Example 197

Example 194 (63 mg, 153 μmol), dimethylamine (3 mL of a 40% solution in water), and ammonium chloride (100 mg) were combined in N,N-dimethylformamide and stirred at ambient temperature in a sealed tube for 5 d. The solution was concentrated onto 0.6 g silica and applied to a bed of silica. Medium pressure liquid chromatography employing a gradient from 5–10% methanol:dichloromethane afforded 60 mg of an orange solid. NMR (d$_6$-DMSO): 11.80 (s, 1H), 9.20 (d, 1H), 8.45 (s, 1H), 7.95 (d, 1H), 7.55 (d, 1H), 7.40 (dd, 1H), 7.2–7.28 (m, 2H), 6.93 (d, 1H), 4.90 (s, 2H), 4.82 (s, 2H), 4.05 (s, 2H), 3.0 (s, 3H), 2.83 (s, 3H). MS (ES+): m/e 434 (M+Na).

Example 198

The epoxide (42 mg, 0.11 mmol), dimethylamine (3 mL of a 40% solution in water), and ammonium chloride (100 mg) were combined in 10 mL N,N-dimethylformamide and stirred in a sealed tube for 16 h. The mixture was concentrated onto 700 mg silica and applied to a bed of silica. Medium pressure liquid chromatography employing a gradient of 15–25% methanol:dichloromethane afforded approximately 5 mg of the polar desired. NMR (d$_6$-DMSO): 12.1 (br s, 1H), 9.55 (d, 1H), 8.45–8.52 (m, 2H), 7.72 (d, 1H), 7.65 (dd, 1H), 7.35–7.5 (m, 2H), 7.15 (d, 1H), 5.75 (s, 2H), 5.18 (s, 2H), 4.15–4.35 (m, 4H), 2.70 (m, 1H), 2.55 (s, 6H), 2.50 (m, 1H). MS (ES+): m/e 428 (M+1).

Example 199

This compound was prepared by the same procedure as Example 198 using morpholine: MS (ES+): m/e 470 (M+1).

Utility

The compounds of the present invention are useful, inter alia, as therapeutic agents. Particularly, the compounds are useful for kinase inhibition, such as, for example, trk, VEGFR, PDGFR, PKC, MLK, DLK, Tie-2, FLT-3, and CDK1–6. Various compounds of the present invention show enhanced pharmaceutical properties over those disclosed in the art and improved pharmacokinetic properties in mammals. The compounds of the present invention show enhanced pharmaceutical properties over those disclosed in the art, including increased MLK and DLK dual inhibition activity, or increased VEGFR and Tie-2 dual inhibition activity, along with improved pharmacokinetic properties in mammals.

In one embodiment, the present invention provides a method for treating or preventing diseases and disorders, such as those disclosed herein, which comprises administering to a subject in need of such treatment or prevention a therapeutically effective amount of a compound of the present invention.

In an additional embodiment, the present invention provides a method for inhibiting trk kinase activity comprising providing a compound of the present invention in an amount sufficient to result in effective inhibition. Particularly, inhibition of trk implies utility in, for example, diseases of the prostate such as prostate cancer and benign prostate hyperplasia, as well as for the treatment of inflammation, such as neurological inflammation and chronic arthritis inflammation. In a preferred embodiment, the trk kinase receptor is trk A.

The majority of cancers have an absolute requirement for angiogenesis, the process by which new blood vessels are formed. The most potent angiogenic cytokine is vascular endothelial growth factor (VEGF) and there has been substantial research into the development of VEGF/VEGF receptor (VEGFR) antagonists. Receptor tyrosine kinase (RTK) inhibitors could have broad spectrum antitumor activity in patients with advanced pre-treated breast and colorectal carcinoma and Kaposi's sarcoma. Potentially these agents may play a role in the treatment of both early (adjuvant) and advanced cancer. The importance of angiogenesis for the progressive growth and viability of solid tumors is well established. Emerging data suggest an involvement of angiogenesis in the pathophysiology of hematologic malignancies as well. Recently, authors have reported increased angiogenesis in the bone marrow of patients with acute myeloid leukemia (AML) and normalization of bone marrow microvessel density when patients achieved a complete remission (CR) after induction chemotherapy. Tumor angiogenesis depends on the expression of specific mediators that initiate a cascade of events leading to the formation of new microvessels. Among these, VEGF (vascular endothelial growth factor), FGF (fibroblast growth factor) play a pivotal role in the induction of neovascularization in solid tumors. These cytokines stimulate migration and proliferation of endothelial cells and induce angiogenesis in vivo. Recent data suggest an important role for these mediators in hematologic malignancies as well. Isolated AML blasts overexpress VEGF and VEGF receptor 2. Thus, the VEGF/VEGFR-2 pathway can promote the growth of leukemic blasts in an autocrine and paracrine manner. Therefore, neovascularization and angiogenic mediators/receptors may be promising targets for anti-angiogenic and anti-leukemic treatment strategies. Thus, in other embodiments, the present invention provides a method for treating or preventing angiogenic disorders where VEGFR kinase activity contributes to pathological conditions, the method comprising providing a compound of the present invention in an amount sufficient to result in the vascular endothelial growth factor receptor being contacted with an effective inhibitory amount of the compound. Inhibition of VEGFR implies utility in, for example, angiogenic disorders such as cancer of solid tumors, endometriosis, macular degeneration, retinopathy, diabetic retinopathy, psoriasis, hemangioblastoma, as well as other ocular diseases and cancers.

FLT3, a member of the receptor tyrosine kinase (RTK) class III, is preferentially expressed on the surface of a high proportion of acute myeloid leukemia (AML) and B-lineage acute lymphocytic leukemia (ALL) cells in addition to hematopoietic stem cells, brain, placenta and liver. An interaction of FLT3 and its ligand has been shown to play an important role in the survival, proliferation and differentiation of not only normal hematopoetic cells but also leukemia cells. Mutations of the FLT3 gene was first reported as an internal tandem duplication (ITD) of the juxtamembrane (JM) domain-coding sequence, subsequently as a missense mutation of D835 within a kinase domain. ITD- and D835- mutations are essentially found in AML and their frequencies are approximately 20 and 6% of adults with AML, respectively. Thus, mutation of the FLT3 gene is so far the most frequent genetic alteration reported to be involved in AML. Several large-scale studies in well-documented patients published to date have demonstrated that ITD-mutation is strongly associated with leukocytosis and a poor prognosis. An inhibitor compound of FLT3 tyrosine kinase have an application in treatment of leukemia. The present invention provides a method for treating disorders characterized by responsiveness to FLT3 inhibition, the method comprising providing a compound of the present invention in an amount sufficient to result in the inhibition of FLT3.

Platelet-derived growth factor (PDGF) was one of the first polypeptide growth factors identified that signals through a cell surface tyrosine kinase receptor (PDGF-R) to stimulate various cellular functions including growth, proliferation, and differentiation. Since then, several related genes have been identified constituting a family of ligands (primarily PDGF A and B) and their cognate receptors (PDGF-R alpha and beta). To date, PDGF expression has been shown in a number of different solid tumors, from glioblastomas to prostate carcinomas. In these various tumor types, the biologic role of PDGF signaling can vary from autocrine stimulation of cancer cell growth to more subtle paracrine interactions involving adjacent stroma and even angiogenesis. Thus, in additional embodiments, the present invention provides a method for treating or preventing disorders where PDGFR activity contributes to pathological conditions, the method comprising providing a compound of the present invention in an amount sufficient to result in the platelet derived growth factor receptor being contacted with an effective inhibitory amount of the compound. Inhibition of PDGFR implies utility in, for example, various forms of neoplasia, rheumatoid arthritis, chronic arthritis, pulmonary fibrosis, myelofibrosis, abnormal wound healing, diseases with cardiovascular end points, such as atherosclerosis, restenosis, post-angioplasty restenosis, and the like.

In further embodiments, the present invention provides a method for treating or preventing disorders where MLK activity contributes to pathological conditions, such as those listed above, wherein the method comprises providing a compound of the present invention in an amount sufficient to result in the MLK receptor being contacted with an effective inhibitory amount of the compound. Inhibition of MLK implies utility in, for example, forms of cancer where MLKs play a pathological role as well as in neurological disorders.

In still other embodiments, the present invention provides a method for treating disorders characterized by the aberrant activity of trophic factor responsive cells, the method comprising providing a compound of the present invention in an amount sufficient to result in the trophic factor cell receptor being contacted with an effective activity inducing amount of the compound. In certain preferred embodiments, the activity of the trophic factor responsive cells is ChAT activity.

Fibroblast growth factor receptors (FGFR) are members of a family of polypeptides synthesized by a variety of cell types during the processes of embryonic development and in adult tissues. FGFR have been detected in normal and malignant cells and are involved in biological events that include mitogenic and angiogenic activity with a consequent crucial role in cell differentiation and development. To activate signal transduction pathways, FGFR are coupled to fibroblast growth factors (FGF) and heparan sulfate (HS) proteoglycans to form a biologically fundamental ternary complex. Based on these considerations, inhibitors able to block the signaling cascade through a direct interaction with FGFR could have antiangiogenesis and subsequent antitumor activity. Accordingly, the present invention provides a method for treating disorders characterized by the aberrant activity of FGF responsive cells, the method comprising providing a compound of the present invention in an amount sufficient to result in the FGFR being contacted with an effective activity inducing amount of the compound.

The compounds of the present invention can also have positive effects on the function and survival of trophic factor responsive cells by promoting the survival of neurons. With respect to the survival of a cholinergic neuron, for example, the compound may preserve the survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population.

A variety of neurological disorders are characterized by neuronal cells which are dying, injured, functionally compromised, undergoing axonal degeneration, at risk of dying, etc. These neurodegenerative diseases and disorders include, but are not limited to, Alzheimer's disease; motor neuron disorders (e.g. amyotrophic lateral sclerosis); Parkinson's disease; cerebrovascular disorders (e.g., stroke, ischemia); Huntington's disease; AIDS dementia; epilepsy; multiple sclerosis; peripheral neuropathies including diabetic neuropathy and chemotherapy induced peripheral neuropathy, AID related peripheral neuropathy; disorders induced by excitatory amino acids; and disorders associated with concussive or penetrating injuries of the brain or spinal cord.

In other preferred embodiments, the compounds of the present invention are useful for treating or preventing multiple myeloma and leukemias including, but not limited to, acute myelogenous leukemia, chronic myelogenous leukemia, acute lymphocytic leukemia, and chronic lymphocytic leukemia.

In additional embodiments, the present compounds are also useful in the treatment of disorders associated with decreased ChAT activity or the death, injury to spinal cord motoneurons, and also have utility in, for example, diseases associated with apoptotic cell death of the central and peripheral nervous system, immune system and in inflammatory diseases. ChAT catalyzes the synthesis of the neurotransmitter acetylcholine, and it is considered an enzymatic marker for a functional cholinergic neuron. A functional neuron is also capable of survival. Neuron survival is assayed by quantification of the specific uptake and enzymatic conversion of a dye (e.g., calcein AM) by living neurons. The compounds described herein may also find utility in the treatment of disease states involving malignant cell proliferation, such as many cancers.

The compounds of the present invention have important functional pharmacological activities which find utility in a variety of settings, including both research and therapeutic arenas. For ease of presentation, and in order not to limit the range of utilities for which these compounds can be characterized, the activities of the compounds of the present invention can be generally described as follows:

A. Inhibition of enzymatic activity

B. Effect on the function and/or survival of trophic factor responsive cells

C. Inhibition of inflammation-associated responses

D. Inhibition of cell growth associated with hyperproliferative states

E. Inhibition of developmentally programmed motoneuron death

Inhibition of enzymatic activity can be determined using, for example, VEGFR inhibition (e.g., VEGFR2 inhibition), MLK inhibition (e.g., MLK1, MLK2 or MLK3 inhibition), PDGFR kinase inhibition, NGF-stimulated trk phosphorylation, PKC inhibition, or trk tyrosine kinase inhibition assays. Effect on the function and/or survival of trophic factor responsive cells, e.g., cells of a neuronal lineage, can be established using any of the following assays: (1) cultured spinal cord choline acetyltransferase ("ChAT") assay; (2) cultured dorsal root ganglion ("DRG") neurite extension assay; (3) cultured basal forebrain neuron ("BFN") ChAT activity assay. Inhibition of inflammation-associated response can be established using an indoleamine 2,3-dioxygenase ("IDO") mRNA assay. Inhibition of cell growth associated with hyperproliferative states can be determined by measuring the growth of cell lines of interest, such as an AT2 line in the case of prostate cancer. Inhibition of developmentally programmed motoneuron death can be assessed in ovo using embryonic chick somatic motoneurons, which cells undergo naturally occurring death between embryonic days 6 and 10, and analyzing inhibition of such naturally occurring cell death as mediated by the compounds disclosed herein.

The inhibition of enzymatic activity by the compounds of the present invention can be determined using, for example, the following assays:

VEGFR Inhibition Assay
MLK Inhibition Assay
PKC Activity Inhibition Assay
trka Tyrosine Kinase Activity Inhibition Assay
Tie-2 Inhibition Assay
CDK1–6 Inhibition Assay
Inhibition of NGF-stimulated trk phosphorylation in a whole cell preparation
Platelet Derived Growth Factor Receptor (PDGFR) inhibition assay A description of assays that may be used in connection with the present invention are set forth below. They are not intended, nor are they to be construed, as limiting the scope of the disclosure.

Inhibition of trkA Tyrosine Kinase Activity

Selected compounds of the present invention were tested for their ability to inhibit the kinase activity of baculovirus-expressed human trkA cytoplasmic domain using an ELISA-based assay as previously described (Angeles et al., Anal. Biochem. 236: 49–55, 1996). Briefly, the 96-well microtiter plate was coated with substrate solution (recombinant human phospholipase C-γ1/glutathione S-transferase fusion protein (Rotin et al., EMBO J., 11: 559–567, 1992). Inhibition studies were performed in 100 µl assay mixtures containing 50 mM Hepes, pH 7.4, 40 µM ATP, 10 mM $MnCl_2$, 0.1% BSA, 2% DMSO, and various concentrations of inhibitor. The reaction was initiated by addition of trkA kinase and allowed to proceed for 15 minutes at 37° C. An antibody to phosphotyrosine (UBI) was then added, followed by a secondary enzyme-conjugated antibody, alkaline phosphatase-labelled goat anti-mouse IgG (Bio-Rad). The activity of the bound enzyme was measured via an amplified detection system (Gibco-BRL). Inhibition data were analyzed using the sigmoidal dose-response (variable slope) equation in GraphPad Prism. The concentration that resulted in 50% inhibition of kinase activity is referred to as "$IC_{50}$".

Inhibition of Vascular Endothelial Growth Factor Receptor Kinase Activity

Selected compounds of the present invention were examined for their inhibitory effects on the kinase activity of baculovirus-expressed VEGF receptor (human flk-1, KDR, VEGFR2) kinase domain using the procedure described for the trkA kinase ELISA assay described above. The kinase reaction mixture, consisting of 50 mM Hepes, pH 7.4, 40 µM ATP, 10 mM $MnCl_2$, 0.1% BSA, 2% DMSO, and various concentrations of inhibitor, was transferred to PLC-γ/GST-coated plates. VEGFR kinase was added and the reaction was allowed to proceed for 15 min. at 37° C. Detection of phosphorylated product was accomplished by addition of anti-phosphotyrosine antibody (UBI). A secondary enzyme-conjugated antibody was delivered to capture the antibody-phosphorylated PLC-γ/GST complex. The activity of the bound enzyme was measured via an amplified detection system (Gibco-BRL). Inhibition data were analyzed using the sigmoidal dose-response (variable slope) equation in GraphPad Prism.

Inhibition of Mixed Lineage Kinase-1 Activity

The kinase activity of MLK1 was assessed using the Millipore Multiscreen TCA "in-plate" format as described for protein kinase C (Pitt & Lee, J. Biomol. Screening, 1: 47–51, 1996). Briefly, each 50-µl assay mixture contained 20 mM Hepes, pH 7.0, 1 mM EGTA, 10 mM $MgCl_2$, 1 mM DTT, 25 mM β-glycerophosphate, 60 µM ATP, 0.25 µCi [γ-$^{32}$P]ATP, 0.1% BSA, 500 µg/ml myelin basic protein (UBI #13-104), 2% DMSO, 1 µM of test compound, and 1 µg/ml of baculoviral GST-MLK1$_{KD}$. Samples were incubated for 15 min at 37° C. The reaction was stopped by adding ice cold 50% TCA and the proteins were allowed to precipitate for 30 min at 4° C. The plates were then washed with ice cold 25% TCA. Supermix scintillation cocktail was added, and the plates were allowed to equilibrate for 1–2 hours prior to counting using the Wallace MicroBeta 1450 PLUS scintillation counter.

Dual Leucine Zipper Bearing Kinase Assay

Compounds were tested for their ability to inhibit the kinase activity of recombinant baculoviral human DLK, containing the kinase domain and leucine zipper. Activity was measured in 384-well FluoroNunc plates (Cat#460372) using a time-resolved fluorescence readout (PerkinElmer Application Note 1234–968). Plates were coated with 30 µl of the protein substrate MKK7 (Merritt et al. 1999) at a concentration of 20 µg/ml in Tris buffered saline (TBS). Each 30 µl assay contained 20 mM MOPS (pH 7.2), 15 mM $MgCl_2$, 0.1 mM $Na_3VO_4$, 1 mM DTT, 5 mM EGTA, 25 mM β-glycerophosphate, 0.1% BSA, 100 µM ATP, and 2.5% DMSO. Reactions were started by the addition of 10 ng/ml GST-hDLK$_{KD/LZ}$. For $IC_{50}$ determinations, a 10-point dose response curve was generated for each compound. Plates were incubated at 37° C. for 30 minutes, and the reactions stopped by the addition of 100 mM EDTA. Product was detected using Europium-labeled anti-phosphothreonine (Wallac#AD0093; diluted 1:10000 in 3% BSA/T-TBS). Following overnight capture at 4° C., 50 µl enhancement solution (Wallac #1244-105) was added and the plate gently agitated for 5 min. The fluorescence of the resulting solution was then measured using the time-resolved fluorescence (TRF) mode in the Multilabel Reader (Victor2 Model # 1420-018 or Envision Model # 2100). Inhibition data was analyzed using GraphPad PRISM. See also Merritt, S. E., Mata, M., Nihalani, D., Zhu, C., Hu, X., and Holzman, L. B. (1999) The Mixed Lineage Kinase DLK utilizes MKK7 and not MKK4 as Substrate. *J. Biol. Chem.* 274, 10195–10202.

Tie-2 Tyrosine Kinase Assay

Compounds were tested for their ability to inhibit the kinase activity of recombinant baculoviral human $His_6$-Tie2 cytoplasmic domain using a modification of the ELISA described for trkA (Angeles et al., 1996). A 384-well plate format was used for single-point screening while $IC_{50}$s were performed on 96-well plates. For single-point screening, each barcoded 384-well Costar High Binding plate (Cat # 3703) was coated with 50 µl/well of 10 µg/ml substrate solution (recombinant human GST- PLC-γ; Rotin et al., 1992) in Tris-buffered saline (TBS). The Tie2 activity was measured in 50-µl assay mixtures containing 50 mM HEPES (pH 7.2), 40 µM ATP, 10 mM $MnCl_2$, 2.5% DMSO, 0.05% BSA, and 200 ng/ml $His_6$-$Tie2_{CD}$. For $IC_{50}$ determinations, the assays were run as described above but in 96-well Costar High Binding plates (Cat # 3703) and with the volumes doubled. A 10-point dose response curve was generated for each compound. The kinase reaction was allowed to proceed at 37° C. for 20 minutes. The detection antibody, N1-Eu anti-phosphotyrosine (PT66) antibody (Wallac #AD0041), was added at 1:2000 diluted in block buffer [3% BSA in TBS with 0.05% Tween-20 (TBST)]. After one-hour incubation at 37° C., 50 µl of enhancement solution (Wallac #1244-105) was added and the plate was gently agitated. The fluorescence of the resulting solution was then measured using the time-resolved fluorescence (TRF) mode in the Multilabel Reader (Victor2 Model # 1420-018 or Envision Model # 2100). Inhibition data were analyzed using ActivityBase and $IC_{50}$ curves were generated using XLFit. The cited references are as follows:

1. Angeles, T. S., Steffler, C., Bartlett, B. A., Hudkins, R. L., Stephens, R. M., Kaplan, D. R., and Dionne, C. A. (1996) Enzyme-linked immunosorbent assay for trkA tyrosine kinase activity. *Anal. Biochem.* 236, 49–55.
2. Rotin, D., Margolis, B., Mohammadi, M., Daly, R. J., Daum, G., Li, N., Fischer, E. H., Burgess, W. H., Ullrich, A., Schlessinger, J. (1992) SH2 domains prevent tyrosine dephosphorylation of the EGF receptor: identification of Tyr992 as the high-affinity binding site for SH2 domains of phospholipase C-γ. *EMBO J.* 11, 559–567.

Dosage and Formulation

For therapeutic purposes, the compounds of the present invention can be administered by any means that results in the contact of the active agent with the agent's site of action in the body of the subject. The compounds may be administered by any conventional means available for use in conjunction with pharmaceuticals, either as individual therapeutic agents or in combination with other therapeutic agents, such as, for example, analgesics. The compounds of the present invention are preferably administered in therapeutically effective amounts for the treatment of the diseases and disorders described herein to a subject in need thereof.

A therapeutically effective amount can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A preferred daily dose for adult humans includes about 25, 50, 100 and 200 mg, and an equivalent dose in a human child. The compounds may be administered in one or more unit dose forms. The unit dose ranges from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

The compounds of the present invention may be formulated into pharmaceutical compositions by admixture with one or more pharmaceutically acceptable excipients. The excipients are selected on the basis of the chosen route of administration and standard pharmaceutical practice, as described, for example, in *Remington: The Science and Practice of Pharmacy*, $20^{th}$ ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations. Such controlled-release, or extended-release compositions may utilize, for example biocompatible, biodegradable lactide polymers, lactide/glycolide copolymers, polyoxyethylene-polyoxypropylene copolymers, or other solid or semisolid polymeric matrices known in the art.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders and the like.

For oral administration, the tablets, pills, powders, capsules, troches and the like can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; or flavoring agents such as peppermint or cherry flavoring. Capsules may contain any of the afore listed excipients, and may additionally contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers, and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A compound of Formula I:

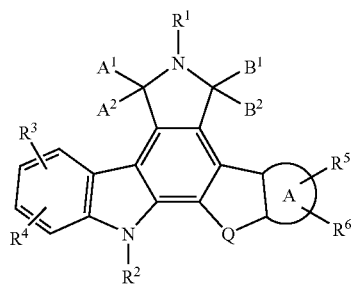

I wherein:
ring A together with the carbon atoms to which it is attached, is a 5-membered aromatic ring in which from 1 to 2 carbon atoms may be replaced by nitrogen atoms;

$A^1$ and $A^2$ are independently selected from H, H; and a group wherein $A^1$ and $A^2$ together form a moiety selected from =O;

$B^1$ and $B^2$ are independently selected from H, H; and a group wherein $B^1$ and $B^2$ together form a moiety selected from =O;

provided that at least one of the pairs $A^1$ and $A^2$, or $B^1$ and $B^2$ forms =O;

$R^1$ is H or optionally substituted alkyl, wherein said optional substituents are one to three $R^{10}$ groups;

$R^2$ is selected from H, $C(=O)R^{2a}$, $C(=O)NR^{2c}R^{2d}$, $SO_2R^{2b}$, $CO_2R^{2b}$, optionally substituted alkyl, optionally substituted alkenyl, optionally substituted alkynyl, optionally substituted cycloalkyl, and optionally substituted heterocycloalkyl, wherein said optional substituents are one to three $R^{10}$ groups;

$R^{2a}$ is selected from optionally substituted alkyl, optionally substituted aryl, $OR^{2b}$, $NR^{2c}R^{2d}$, $(CH_2)_pNR^{2c}R^{2d}$, and $O(CH_2)_pNR^{2c}R^{2d}$, wherein said optional substituents are one to three $R^{10}$ groups;

$R^{2b}$ is selected from H and optionally substituted alkyl, wherein said optional substituents are one to three $R^{10}$ groups;

$R^{2c}$ and $R^{2d}$ are each independently selected from H and optionally substituted alkyl, or together with the nitrogen to which they are attached form an optionally substituted heterocycloalkyl, wherein said optional substituents are one to three $R^{10}$ groups;

at least one of $R^3$, $R^4$, $R^5$, and $R^6$ is selected from $OR^{14}$; $C(=O)R^{22}$; $CH=NR^{26}$; $NR^{11}C(=O)R^{20}$; $NR^{11}C(=O)OR^{15}$; $OC(=O)R^{20}$; $OC(=O)NR^{11}R^{20}$; O-(alkylene)-$R^{24}$; $Z^1$-(alkylene)-$R^{23}$ wherein $Z^1$ is selected from $CO_2$, $O_2C$, $C(=O)$, $NR^{11}$, $NR^{11}C(=O)$, and $NR^{11}C(=O)O$; and (alkylene)-$Z^2$-(alkylene)-$R^{23}$, wherein $Z^2$ is selected from O, $S(O)_y$, $C(=O)NR^{11}$, $NR^{11}C(=O)$, $NR^{11}C(=O)NR^{11}$, $OC(=O)NR^{11}$, $NR^{11}C(=O)O$, wherein said alkylene groups are optionally substituted with one to three $R^{10}$ groups;

the other $R^3$, $R^4$, $R^5$, or $R^6$ moieties can be selected independently from H, $R^{10}$, optionally substituted alkyl, optionally substituted alkenyl, and optionally substituted alkynyl, wherein said optional substituents are one to three $R^{10}$ groups;

Q is selected from an optionally substituted $C_{1-2}$ alkylene, wherein said optional substituents are one to three $R^{10}$ groups;

$R^{10}$ is selected from alkyl, cycloalkyl, spirocycloalkyl, aryl, heteroaryl, heterocycloalkyl, arylalkoxy, F, Cl, Br, I, CN, $CF_3$, $NR^{27A}R^{27B}$, $NO_2$, $OR^{25}$, $OCF_3$, =O, =$NR^{25}$, =N—$OR^{25}$, =N—$N(R^{25})_2$, $OC(=O)R^{25}$, $OC(=O)NHR^{11}$, O—$Si(R^{16})_4$, O-tetrahydropyranyl, ethylene oxide, $NR^{16}C(=O)R^{25}$, $NR^{16}CO_2R^{25}$, $NR^{16}C(=O)NR^{27A}R^{27B}$, $NHC(=NH)NH_2$, $NR^{16}S(O)_2R^{25}$, $S(O)_yR^{25}$, $CO_2R^{25}$, $C(=O)NR^{27A}R^{27B}$, $C(=O)R^{25}$, $CH_2OR^{25}$, $(CH_2)_pOR^{25}$, $CH=NNR^{27A}R^{27B}$, $CH=NOR^{25}$, $CH=NR^{25}$, $CH=NNHCH(N=NH)NH_2$, $S(=O)_2NR^{27A}R^{27B}$, $P(=O)(OR^{25})_2$, $OR^{13}$, and a monosaccharide wherein each hydroxyl group of the monosaccharide is independently either unsubstituted or is replaced by H, alkyl, alkylcarbonyloxy, or alkoxy;

$R^{11}$ is selected from H and optionally substituted alkyl, wherein said optional substituents are one to three $R^{10}$ groups;

$R^{12}$ is selected from optionally substituted alkyl, optionally substituted aryl, and optionally substituted heteroaryl, wherein said optional substituents are one to three $R^{10}$ groups;

$R^{13}$ is the residue of an amino acid after the removal of the hydroxyl moeity from the carboxyl group thereof;

$R^{14}$ is optionally substituted heteroaryl, wherein said optional substituents is one to three $R^{10}$ groups;

$R^{15}$ is optionally substituted alkyl, wherein said optional substituents is one to three $R^{10}$ groups;

$R^{16}$ is H or alkyl;

$R^{17}$ is selected from optionally substituted alkyl, optionally substituted aryl, optionally substituted heteroaryl, optionally substituted cycloalkyl, and optionally substituted heterocycloalkyl, wherein said optional substituents are one to three $R^{10}$ groups;

$R^{18}$ is selected from H, optionally substituted alkyl, optionally substituted aryl, optionally substituted heteroaryl, optionally substituted cycloalkyl, and optionally substituted heterocycloalkyl, wherein said optional substituents are one to three $R^{10}$ groups;

$R^{19}$ is selected from optionally substituted cycloalkyl, optionally substituted heterocycloalkyl, and optionally substituted heteroaryl, wherein said optional substituents are one to three $R^{10}$ groups;

$R^{20}$ is selected from optionally substituted aryl, optionally substituted heteroaryl, optionally substituted cycloalkyl, and optionally substituted heterocycloalkyl, wherein said optional substituents are one to three $R^{10}$ groups;

$R^{21}$ is selected from H, optionally substituted alkyl, optionally substituted alkenyl, optionally substituted alkynyl, optionally substituted aryl, optionally substituted arylalkyl, optionally substituted heteroaryl, optionally substituted cycloalkyl, and optionally substituted heterocycloalkyl, wherein said optional substituents are one to three $R^{10}$ groups;

$R^{22}$ is selected from optionally substituted aryl, and optionally substituted heteroaryl, wherein said optional substituents are one to three $R^{10}$ groups;

$R^{23}$ is selected from optionally substituted alkenyl, optionally substituted alkynyl, optionally substituted aryl, optionally substituted heteroaryl, optionally substituted cycloalkyl, optionally substituted heterocycloalkyl, $OR^{21}$, $O(CH_2)_pOR^{21}$, $(CH_2)_pOR^{21}$, $SR^{18}$, $SOR^{17}$, $SO_2R^{18}$, CN, $N(R^{20})_2$, $CHOH(CH_2)_pN(R^{11})_2$, $C(=O)N(R^{18})_2$, $NR^{18}C(=O)R^{18}$, $NR^{18}C(=O)N(R^{18})_2$, $C(=NR^{18})OR^{18}$, $C(R^{12})=NOR^{18}$, $NHOR^{21}$, $NR^{18}C(=NR^{18})N(R^{18})_2$, NHCN, $CONR^{18}OR^{18}$, $CO_2R^{18}$, $OCOR^{17}$, $OC(=O)N(R^{18})_2$, $NR^{18}C(=O)OR^{17}$, and $C(=O)R^{18}$, wherein said optional substituents are one to three $R^{10}$ groups;

$R^{24}$ is selected from optionally substituted alkenyl, optionally substituted aryl, optionally substituted heteroaryl, optionally substituted cycloalkyl, optionally substituted heterocycloalkyl, CN, $OR^{21}$, $O(CH_2)_pOR^{21}$, $(CH_2)_pOR^{21}$, $SR^{19}$, $SOR^{17}$, $SO_2R^{18}$, $N(R^{18})_2$, $CHOH(CH_2)_pN(R^{11})_2$, $NR^{18}C(=O)R^{18}$, $NR^{18}C(=O)N(R^{18})_2$, $C(=NR^{18})OR^{18}$, $NHOR^{21}$, $NR^{18}C(=NR^{18})N(R^{18})_2$, NHCN, $C(=O)N(R^{18})_2$, $C(=O)NR^{27A}R^{27B}$, $C(=O)NR^{11}R^{28}$, $C(=O)NR^{18}OR^{18}$, $C(=O)NR^{11}N(R^{11})_2$, $C(=O)NR^{11}(alkylene)NR^{27A}R^{27B}$, $CO_2R^{18}$, $OCOR^{17}$, $OC(=O)N(R^{18})_2$, $NR^{18}C(=O)OR^{17}$, $C(=O)NR^{11}R^{18}$ and $C(=O)R^{18}$, wherein said optional substituents are one to three $R^{10}$ groups;

$R^{25}$ is H, alkyl, aryl, heteroaryl, cycloalkyl, or heterocycloalkyl;

$R^{26}$ is selected from optionally substituted cycloalkyl and optionally substituted heterocycloalkyl, wherein said optional substituents are one to three $R^{10}$ groups;

$R^{27A}$ and $R^{27B}$ are each independently selected from H and alkyl, or together with the nitrogen to which they are attached form an optionally substituted heterocycloalkyl, wherein said optional substituents are selected from alkyl, aryl and heteroaryl;

$R^{28}$ is optionally substituted arylalkyl, wherein said optional substituent is one to three $R^{10}$ groups;

p is independently selected from 1, 2, 3, and 4;

y is independently selected from 0, 1 and 2; and provided that:

when $A^1, A^2$ is =O; $B^1$, $B^2$ are independently H or OH, or $B^1$, $B^2$ combine to form =O; rings A and B are each phenylene; Q is CH—$R^a$; and one of $R^2$ or $R^a$ is H and the other is optionally substituted

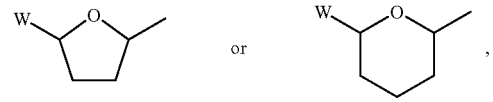

wherein W is optionally substituted $C_1$ alkyl, or $NR^{27A}R^{27B}$; then any of $R^3$, $R^4$, $R^5$, and $R^6$ cannot include $OR^{14}$ or O-(alkylene)-$R^{24}$; and a stereoisomer or a pharmaceutically acceptable salt form thereof.

2. The compound of claim 1 wherein ring A is a pyrazolylene.

3. The compound of claim 1 wherein $R^2$ is H, optionally substituted alkyl, optionally substituted alkenyl, optionally substituted alkynyl, or optionally substituted cycloalkyl.

4. The compound of claim 1 wherein at least one of $R^3$, $R^4$, $R^5$, and $R^6$ is $OR^{14}$; $C(=O)R^{22}$; $NR^{11}C(=O)R^{20}$; $NR^{11}C(=O)OR^{15}$; $OC(=O)R^{20}$; or $OC(=O)NR^{11}R^{20}$.

5. The compound of claim 1 wherein $R^{14}$ is benzoxazolyl, benzothiazolyl, pyrimidyl, pyrazinyl or triazinyl; $R^{22}$ is a 5-membered heteroaryl group; $R^{20}$ is heterocycloalkyl or heteroaryl; $R^{23}$ is heteroaryl or heterocycloalkyl; $R^{24}$ is heteroaryl; and $R^{26}$ is heterocycloalkyl, wherein each of said $R^{14}$, $R^{22}$, $R^{20}$, $R^{23}$, $R^{24}$ and $R^{26}$ moieties is optionally substituted with 1 to 3 $R^{10}$ groups.

6. The compound of claim 1 having a structure of Formula II:

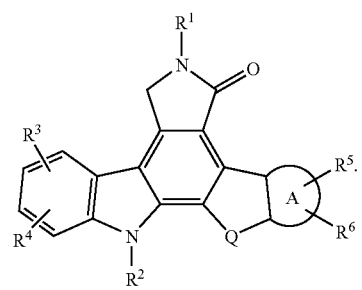

7. The compound of claim 6 wherein ring A is a pyrazolylene.

8. The compound of claim 6 wherein at least one of $R^3$, $R^4$, $R^5$, and $R^6$ is $OR^{14}$, wherein $R^{14}$ is benzoxazole, benzothiazole, pyrimidine, pyrazine or triazine; $C(=O)R^{22}$, wherein $R^{22}$ is a 5-membered heteroaryl group; $NR^{11}C(=O)R^{20}$, wherein $R^{20}$ is heteroaryl; $NR^{11}C(=O)OR^{15}$; $OC(=O)R^{20}$, wherein $R^{20}$ is heterocycloalkyl; or $OC(=O)NR^{11}R^{20}$, wherein $R^{20}$ is cycloalkyl, wherein each of said $R^{14}$, $R^{22}$, and $R^{20}$ moieties is optionally substituted with 1 to 3 $R^{10}$ groups.

9. The compound of claim 6 having a structure of Formula III:

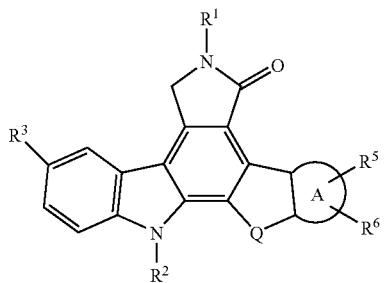

wherein ring A is a pyrazolylene, and $R^1$ is H or alkyl.

10. The compound of claim 9 having a structure of Formula V:

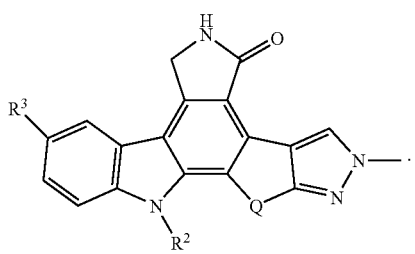

11. The compound of claim 9 having Formula VI:

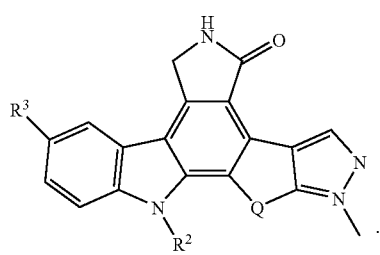

12. The compound of claim 9 wherein $R^2$ is H, $C(=O)R^{2a}$, $C(=O)NR^{2c}R^{2d}$, $SO_2R^{2b}$, $CO_2R^{2b}$, optionally substituted alkyl, optionally substituted alkenyl, optionally substituted alkynyl, or optionally substituted cycloalkyl.

13. The compound of claim 9 wherein at least one of $R^3$, $R^4$, $R^5$, and $R^6$ is $OR^{14}$, wherein $R^{14}$ is benzoxazole, benzothiazole, pyrimidine, pyrazine or triazine; $C(=O)R^{22}$, wherein $R^{22}$ is a 5-membered heteroaryl group; $NR^{11}C(=O)R^{20}$, wherein $R^{20}$ is heteroaryl; $NR^{11}C(=O)OR^{15}$; $OC(=O)R^{20}$, wherein $R^{20}$ is heterocycloalkyl; or $OC(=O)NR^{11}R^{20}$, wherein $R^{20}$ is cycloalkyl, wherein each of said $R^{14}$, $R^{22}$, and $R^{20}$ moieties is optionally substituted with 1 to 3 $R^{10}$ groups.

14. The compound of claim 13 wherein Q is $CH_2CH_2$ and $R^2$ is H or optionally substituted alkyl.

15. The compound of claim 1 wherein the compounds are selected in accordance with the following table:

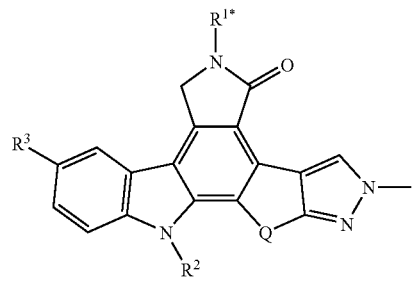

*$R^1$ is H, unless otherwise noted

| Ex. No. | $R^3$ | $R^2$ | Q |
|---|---|---|---|
| 13 | pyrimidin-2-yloxy- | H | $CH_2CH_2$ |
| 14 | pyrimidin-2-yloxy- | $CH_2CH_3$ | $CH_2CH_2$ |

-continued

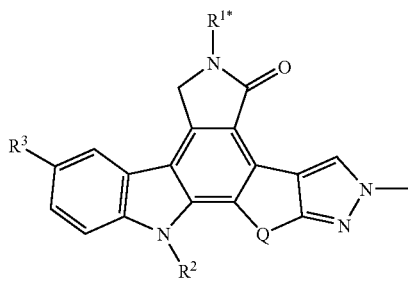

*R¹ is H, unless otherwise noted

| Ex. No. | R³ | R² | Q |
|---|---|---|---|
| 15 | 2-pyrimidinyl-O-CH< | CH₃ | CH₂CH₂ |
| 16 | 2-pyrimidinyl-O-CH< | cyclopentyl-CH₂ | CH₂CH₂ |
| 17 | 2-pyrazinyl-O-CH< | H | CH₂CH₂ |
| 18 | 2-pyrimidinyl-O-CH< | CH₂CH₂CH₂CH₃ | CH₂CH₂ |
| 19 | 2-pyrimidinyl-O-CH< | CH(CH₃)₂ | CH₂CH₂ |
| 20 | 2-pyrimidinyl-O-CH< | cyclopropyl-CH₂ | CH₂CH₂ |
| 21 | 2-pyrimidinyl-O-CH< | R² = cyclopropyl-CH₂; *R¹ = cyclopropyl-CH₂ | CH₂CH₂ |
| 22 | 2-pyrimidinyl-O-CH₂CH₃ 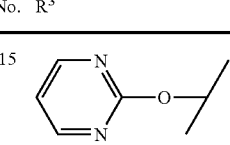 | CH₂CH(CH₃)₂ | CH₂CH₂ |
| 23 | 2-pyrimidinyl-O-CH₃ | CH₂CH₃ | CH₂CH₂ |

-continued
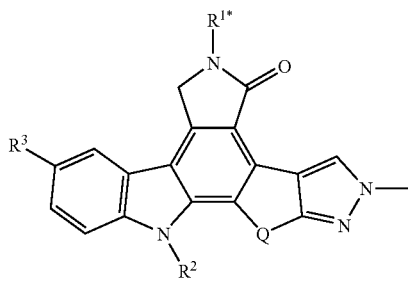
*R¹ is H, unless otherwise noted
| Ex. No. | R³ | R² | Q |
|---|---|---|---|
| 24 | MeO-triazine-OMe (2,4-dimethoxy-1,3,5-triazin-6-yl-oxy) | $CH_2CH(CH_3)_2$ | $CH_2CH_2$ |
| 25 | 2-furyl-C(O)- | $CH_2CH_3$ | $CH_2CH_2$ |
| 26 | 2-thienyl-C(O)- | H | $CH_2CH_2$ |
| 27 | 2-thienyl-C(O)- | $CH_2CH_3$ | $CH_2CH_2$ |
| 28 | 2-furyl-C(O)- | H | $CH_2CH_2$ |
| 29 | 2-furyl-C(O)- | $CH_2CH_2CH_3$ | $CH_2CH_2$ |
| 30 | 2-furyl-C(O)- | $CH_2CH(CH_3)_2$ | $CH_2CH_2$ |
| 31 | 2-thienyl-C(O)- | $CH_2CH(CH_3)_2$ | $CH_2CH_2$ |

-continued

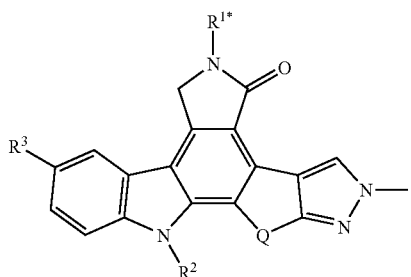

*R[1] is H, unless otherwise noted

| Ex. No. | R[3] | R[2] | Q |
|---|---|---|---|
| 32 | 2-acetylfuran | CH$_2$CH=CH$_2$ | CH$_2$CH$_2$ |
| 33 | 2-acetylfuran | CH$_2$COOEt | CH$_2$CH$_2$ |
| 34 | 2-acetylfuran | CH$_2$COOH | CH$_2$CH$_2$ |
| 35 | 3-chloro-2-acetylthiophene | CH$_2$CH(CH$_3$)$_2$ | CH$_2$CH$_2$ |
| 36 | 3-acetylthiophene | CH$_2$CH(CH$_3$)$_2$ | CH$_2$CH$_2$ |
| 37 | 3-acetylfuran | CH$_2$CH(CH$_3$)$_2$ | CH$_2$CH$_2$ |
| 38 | 3-bromo-2-acetylthiophene | CH$_2$CH(CH$_3$)$_2$ | CH$_2$CH$_2$ |
| 39 | 2-acetylthiophene | CH$_2$CH$_2$CH$_3$ | CH$_2$CH$_2$ |
| 40 | 2-acetylthiophene | CH(CH$_3$)$_2$ | CH$_2$CH$_2$ |

-continued

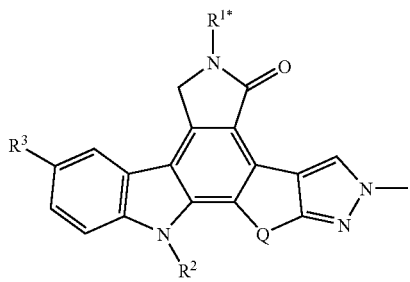

*R¹ is H, unless otherwise noted

| Ex. No. | R³ | R² | Q |
|---|---|---|---|
| 41 | 3-Cl, 4-SO₂—, 2-acetyl thiophene | CH₂CH(CH₃)₂ | CH₂CH₂ |
| 42 | 3-Br, 2-acetyl thiophene | CH₂CH₂NMe₂ | CH₂CH₂ |
| 43 | 2-acetyl thiophene | (CH₂)₂-pyrrolidine | CH₂CH₂ |
| 44 | 2-acetyl furan | (CH₂)₂-pyrrolidine | CH₂CH₂ |
| 45 | 4-methyl, 2-acetyl thiophene | CH₂CH(CH₃)₂ | CH₂CH₂ |
| 46 | 2-acetyl thiophene | (CH₂)₆-pyrrolidine | CH₂CH₂ |
| 47 | 3-methyl, 2-acetyl thiophene | (CH₂)₂-pyrrolidine | CH₂CH₂ |
| 48 | 4-methyl, 2-acetyl thiophene | (CH₂)₂-pyrrolidine | CH₂CH₂ |
| 49 | 3-Cl, 2-acetyl thiophene | (CH₂)₂-pyrrolidine | CH₂CH₂ |

-continued

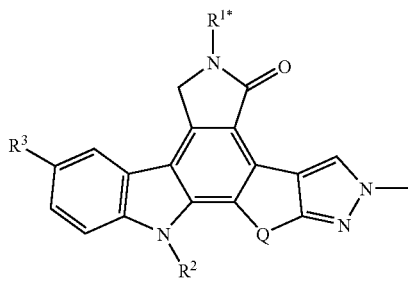

*$R^1$ is H, unless otherwise noted

| Ex. No. | $R^3$ | $R^2$ | Q |
|---|---|---|---|
| 50 | isopropyl-O-C(O)-NH- | $CH_2CH_2CH_3$ | $CH_2CH_2$ |
| 51 | ethyl-O-C(O)-NH- | $CH_2CH_2CH_3$ | $CH_2CH_2$ |
| 52 | isobutyl-O-C(O)-NH- | $CH_2CH_2CH_3$ | $CH_2CH_2$ |
| 53 | n-propyl-O-C(O)-NH- | $CH_2CH_2CH_3$ | $CH_2CH_2$ |
| 54 | F-CH$_2$CH$_2$-O-C(O)-NH- | $CH_2CH_2CH_3$ | $CH_2CH_2$ |
| 55 | Cl-CH$_2$CH$_2$-O-C(O)-NH- | $CH_2CH_2CH_3$ | $CH_2CH_2$ |
| 56 | ethyl-O-C(O)-NH- | $CH(CH_3)_2$ | $CH_2CH_2$ |
| 57 | isobutyl-O-C(O)-NH- | $CH_2CH(CH_3)_2$ | $CH_2CH_2$ |
| 58 | isopropyl-O-C(O)-NH- | $CH_2CH(CH_3)_2$ | $CH_2CH_2$ |
| 59 | n-propyl-O-C(O)-NH- | $CH_2CH(CH_3)_2$ | $CH_2CH_2$ |
| 60 | ethyl-O-C(O)-NH- | $CH_2CH(CH_3)_2$ | $CH_2CH_2$ |

-continued

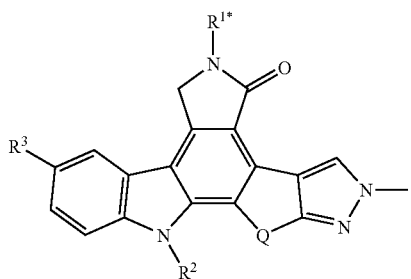

*$R^1$ is H, unless otherwise noted

| Ex. No. | $R^3$ | $R^2$ | Q |
|---|---|---|---|
| 61 | isopropyl-O-C(O)-NH- | $CH(CH_3)_2$ | $CH_2CH_2$ |
| 62 | Br, -CH2CH2-O-C(O)-NH-CH3 | $CH_2CH_2CH_3$ | $CH_2CH_2$ |
| 63 | F, -CH2CH2-O-C(O)-NH-CH3 | $CH_2CH(CH_3)_2$ | $CH_2CH_2$ |
| 64 | Cl, -CH2CH2-O-C(O)-NH-CH3 | $CH_2CH(CH_3)_2$ | $CH_2CH_2$ |
| 65 | Br, -CH2CH2-O-C(O)-NH-CH3 | $CH_2CH(CH_3)_2$ | $CH_2CH_2$ |
| 66 | isobutyl-O-C(O)-NH-CH3 | $CH(CH_3)_2$ | $CH_2CH_2$ |
| 67 | pyrrolidinyl-CH2CH2-O-C(O)-NH-CH3 | $CH(CH_3)_2$ | $CH_2CH_2$ |
| 68 | piperidinyl-CH2CH2-O-C(O)-NH-CH3 | $CH(CH_3)_2$ | $CH_2CH_2$ |
| 69 | 2-pyridyl-CH2CH2-O-C(O)-NH-CH3 | $CH(CH_3)_2$ | $CH_2CH_2$ |
| 70 | pyrrolidinyl-C(O)-O- | $CH_2CH_3$ | $CH_2CH_2$ |

-continued

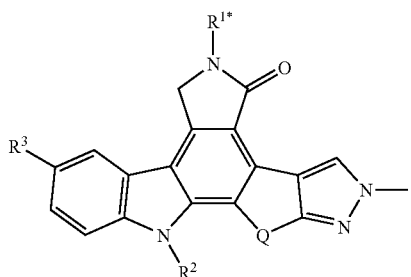

*R¹ is H, unless otherwise noted

| Ex. No. | R³ | R² | Q |
|---|---|---|---|
| 71 | pyrrolidine-N-C(=O)- | CH₂CH(CH₃)₂ | CH₂CH₂ |
| 72 | pyrrolidine-N-C(=O)-O-CH₃ | CH(CH₃)₂ | CH₂CH₂ |
| 73 | 1-methylpiperidin-4-yl-N(CH₃)-C(=O)- | CH₂CH(CH₃)₂ | CH₂CH₂ |
| 74 | 4-pyridyl-C(=O)-NH- | CH(CH₃)₂ | CH₂CH₂ |
| 75 | 2-thienyl-C(=O)-NH- | CH₂CH₃ | CH₂CH₂ |
| 76 | 2-furyl-C(=O)-NH- | CH₂CH₂CH₃ | CH₂CH₂ |
| 77 | 3-pyridyl-C(=O)-NH- | CH(CH₃)₂ | CH₂CH₂ |
| 78 | 4-pyridyl-C(=O)-NH- | CH(CH₃)₂ | CH₂CH₂ |
| 79 | 2-thienyl-C(=O)-NH- | CH₂CH(CH₃)₂ | CH₂CH₂ |
| 80 | 2-furyl-C(=O)-NH- | CH₂CH(CH₃)₂ | CH₂CH₂ |

-continued

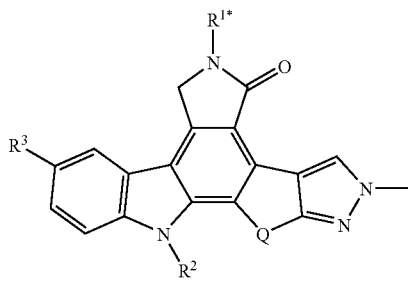

*R¹ is H, unless otherwise noted

| Ex. No. | R³ | R² | Q |
|---|---|---|---|
| 81 | isoxazole-C(O)NH- | CH₂CH₂CH₃ | CH₂CH₂ |
| 82 | isoxazole-C(O)NH- | CH₂CH(CH₃)₂ | CH₂CH₂ |

16. The compound of claim 10 wherein the compounds are selected in accordance with the following table:

| R³ | R² | Q |
|---|---|---|
| pyrimidin-2-yloxy-CH₂- | H | CH₂CH₂ |
| pyrimidin-2-yloxy-CH₂- | CH₂CH₃ | CH₂CH₂ |
| pyrimidin-2-yloxy-CH₂- | CH₃ | CH₂CH₂ |
| pyrimidin-2-yloxy-CH₂- | cyclopentyl-CH₂ | CH₂CH₂ |
| pyrimidin-2-yloxy-CH₂- | H | CH₂CH₃ |

-continued

| R³ | R² | Q |
|---|---|---|
| pyrimidin-2-yloxy-CH₂- | CH₂CH₂H₂CH₃ | CH₂CH₂ |
| pyrimidin-2-yloxy-CH₂- | CH(CH₃)₂ | CH₂CH₂ |
| pyrimidin-2-yloxy-CH₂- | cyclopropyl-CH₂ | CH₂CH₂ |
| pyrimidin-2-yloxy-CH₂- | R¹, R² = CH₂-cyclopropyl | CH₂CH₂ |
| pyrimidin-2-yloxy-CH₂- | CH₂CH(CH₃)₂ | CH₂CH₂ |

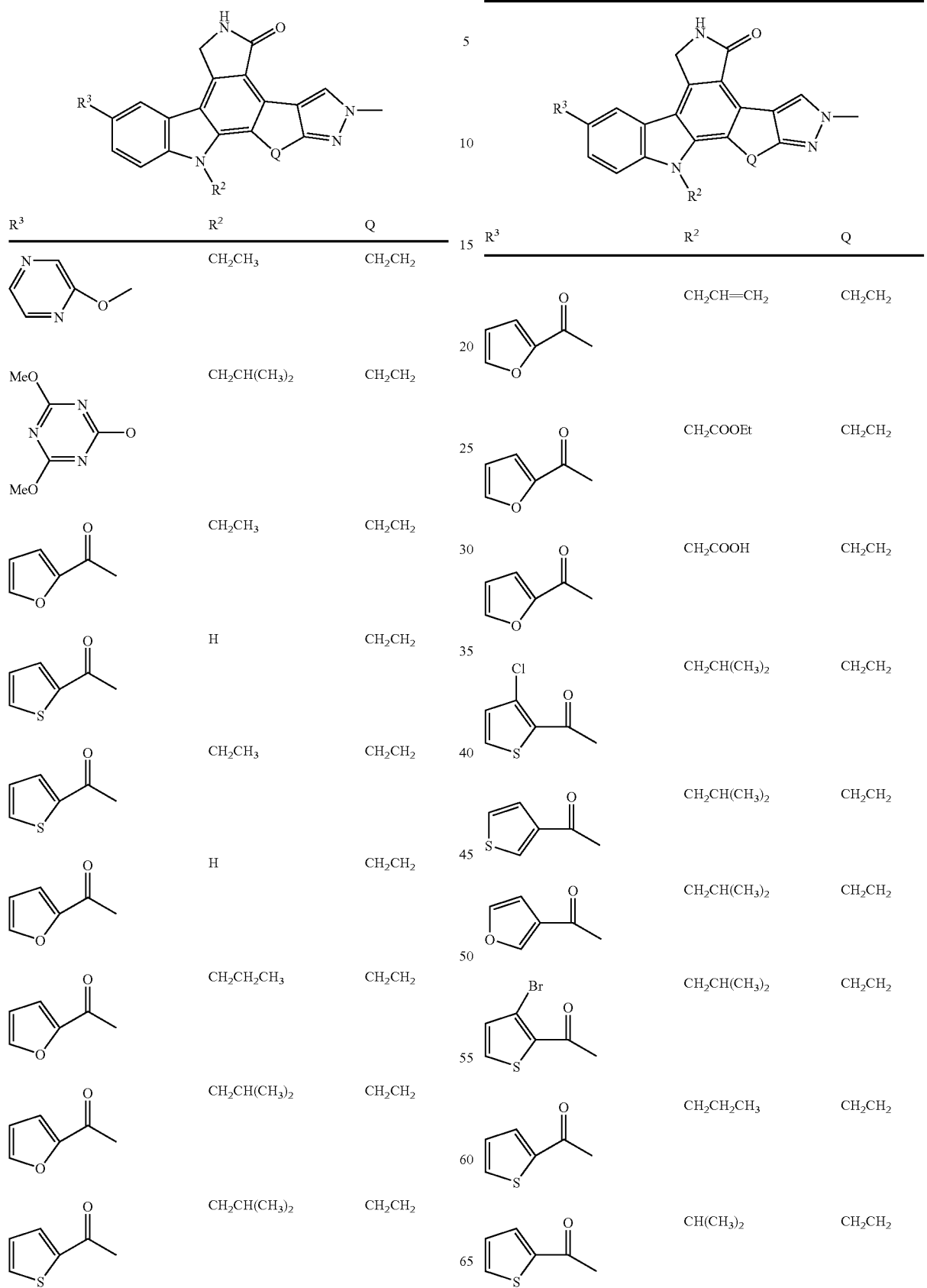

-continued

| R³ | R² | Q |
|---|---|---|
| 2-methoxypyrazinyl | CH₂CH₃ | CH₂CH₂ |
| 4,6-dimethoxy-1,3,5-triazin-2-yl | CH₂CH(CH₃)₂ | CH₂CH₂ |
| 2-furanylcarbonyl | CH₂CH₃ | CH₂CH₂ |
| 2-thienylcarbonyl | H | CH₂CH₂ |
| 2-thienylcarbonyl | CH₂CH₃ | CH₂CH₂ |
| 2-furanylcarbonyl | H | CH₂CH₂ |
| 2-furanylcarbonyl | CH₂CH₂CH₃ | CH₂CH₂ |
| 2-furanylcarbonyl | CH₂CH(CH₃)₂ | CH₂CH₂ |
| 2-thienylcarbonyl | CH₂CH(CH₃)₂ | CH₂CH₂ |
| 2-furanylcarbonyl | CH₂CH=CH₂ | CH₂CH₂ |
| 2-furanylcarbonyl | CH₂COOEt | CH₂CH₂ |
| 2-furanylcarbonyl | CH₂COOH | CH₂CH₂ |
| 3-chloro-2-thienylcarbonyl | CH₂CH(CH₃)₂ | CH₂CH₂ |
| 3-thienylcarbonyl | CH₂CH(CH₃)₂ | CH₂CH₂ |
| 3-furanylcarbonyl | CH₂CH(CH₃)₂ | CH₂CH₂ |
| 3-bromo-2-thienylcarbonyl | CH₂CH(CH₃)₂ | CH₂CH₂ |
| 2-thienylcarbonyl | CH₂CH₂CH₃ | CH₂CH₂ |
| 2-thienylcarbonyl | CH(CH₃)₂ | CH₂CH₂ |

-continued

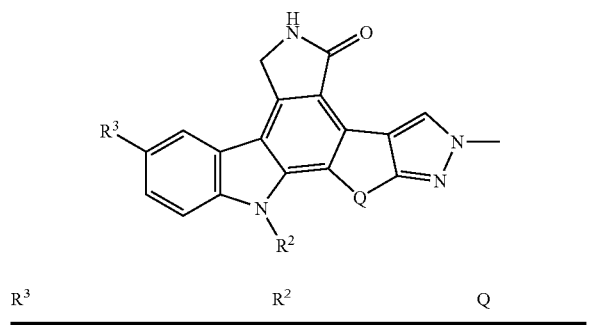

| R³ | R² | Q |
|---|---|---|
| 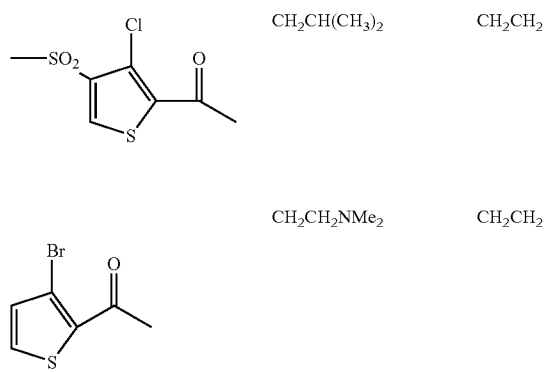 (—SO₂-thiophene with Cl, acetyl) | CH₂CH(CH₃)₂ | CH₂CH₂ |
| (3-Br-thiophen-2-yl)carbonyl | CH₂CH₂NMe₂ | CH₂CH₂ |
| (thiophen-2-yl)carbonyl | (CH₂)₂-pyrrolidine | CH₂CH₂ |
| (furan-2-yl)carbonyl | (CH₂)₂-pyrrolidine | CH₂CH₂ |
| (4-methylthiophen-2-yl)carbonyl | CH₂CH(CH₃)₂ | CH₂CH₂ |
| (thiophen-2-yl)carbonyl | (CH₂)₆-pyrrolidine | CH₂CH₂ |
| (3-methylthiophen-2-yl)carbonyl | (CH₂)₂-pyrrolidine | CH₂CH₂ |

-continued

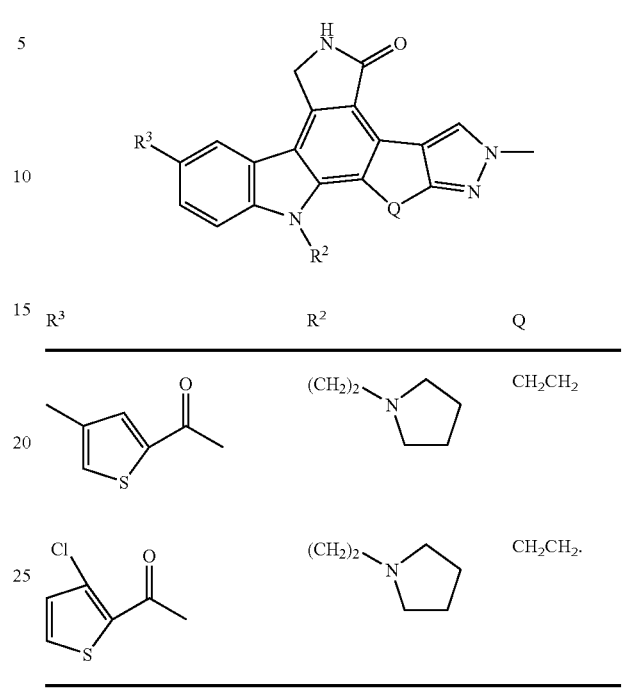

| R³ | R² | Q |
|---|---|---|
| (4-methylthiophen-2-yl)carbonyl | (CH₂)₂-pyrrolidine | CH₂CH₂ |
| (3-chlorothiophen-2-yl)carbonyl | (CH₂)₂-pyrrolidine | CH₂CH₂. |

17. The compound of claim 1 wherein the compounds are selected in accordance with the following table:

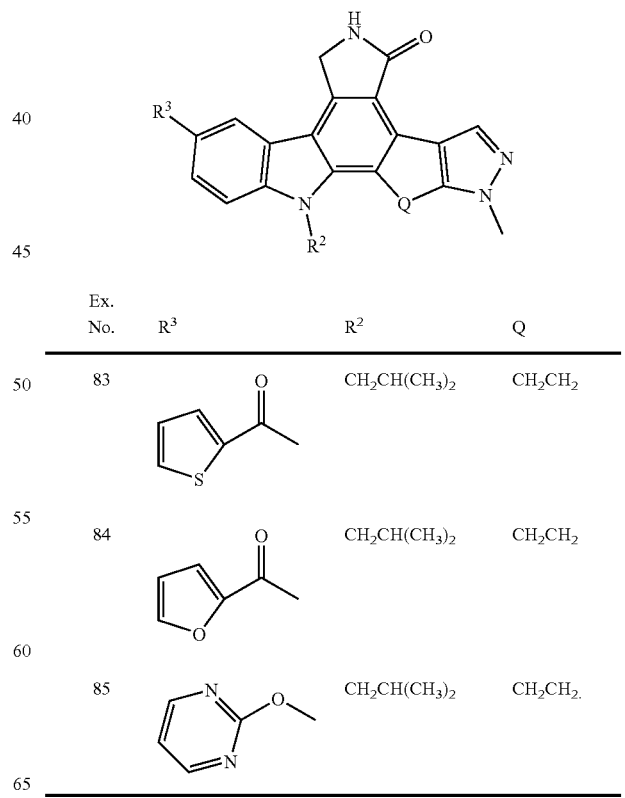

| Ex. No. | R³ | R² | Q |
|---|---|---|---|
| 83 | (thiophen-2-yl)carbonyl | CH₂CH(CH₃)₂ | CH₂CH₂ |
| 84 | (furan-2-yl)carbonyl | CH₂CH(CH₃)₂ | CH₂CH₂ |
| 85 | (2-methoxypyrimidin-yl) | CH₂CH(CH₃)₂ | CH₂CH₂. |

18. The compound of claim 1 wherein the compounds are selected in accordance with the following table:
| Example No. | Structure |
|---|---|
| 87 | 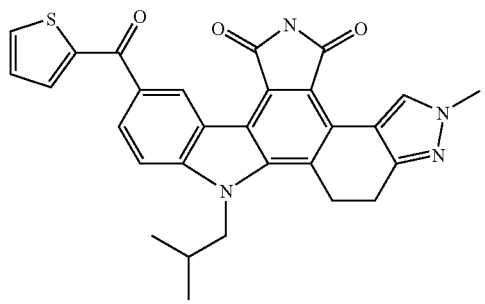 |
| 88 | 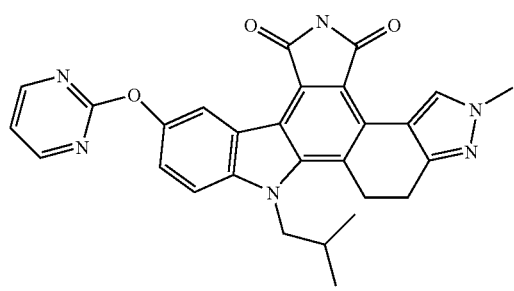 |
| 92 | 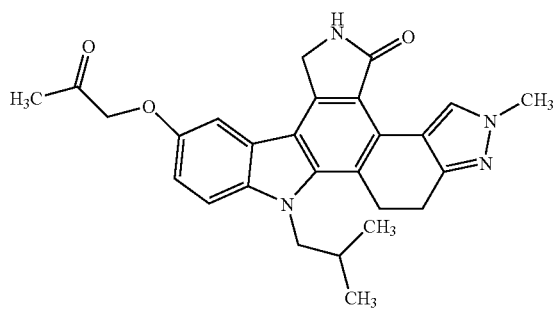 |
| 93 | 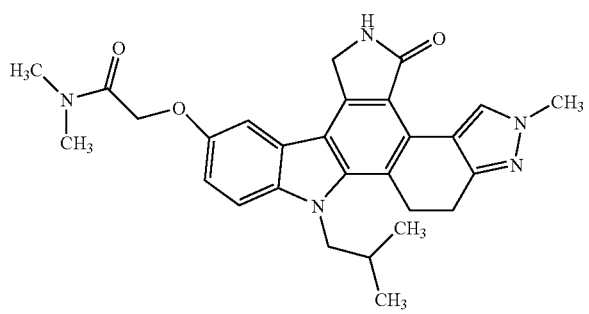 |

-continued
| Example No. | Structure |
|---|---|
| 94 | 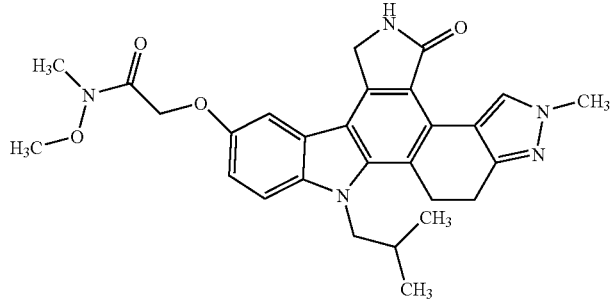 |
| 95 | 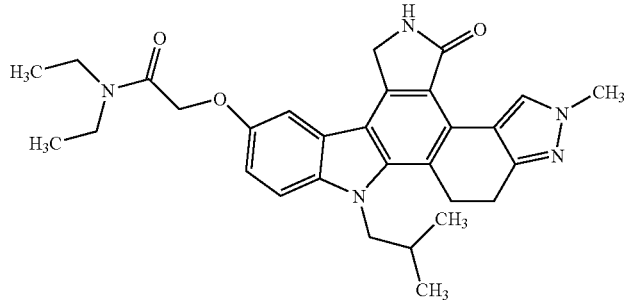 |
| 96 | 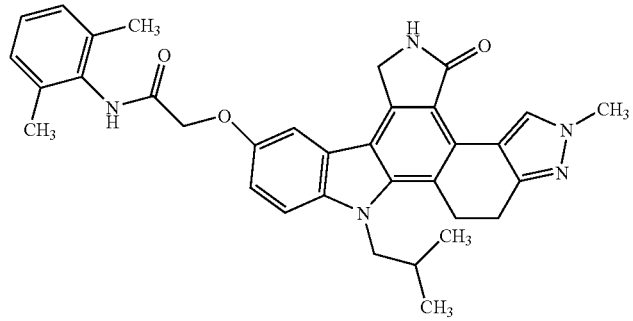 |
| 97 | 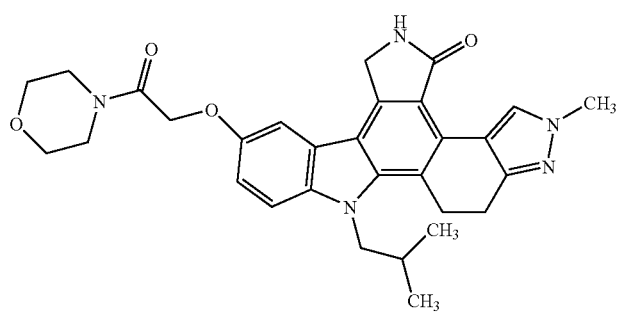 |
| 98 | 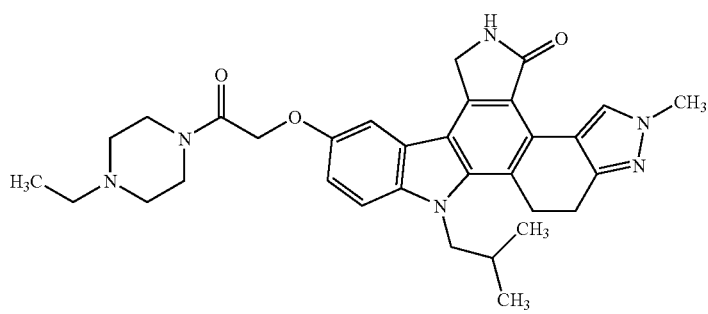 |

-continued
| Example No. | Structure |
|---|---|
| 99 | 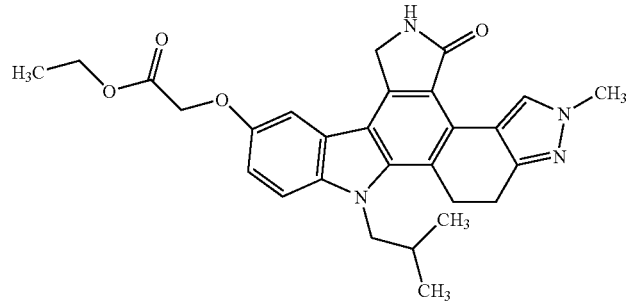 |
| 100 | 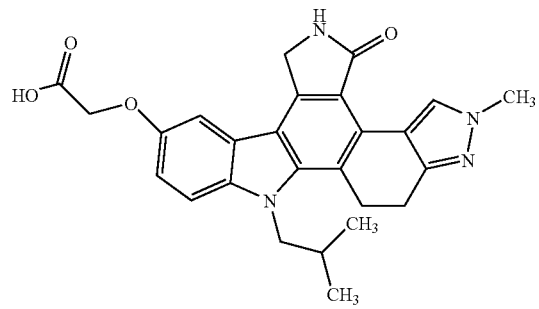 |
| 101 | 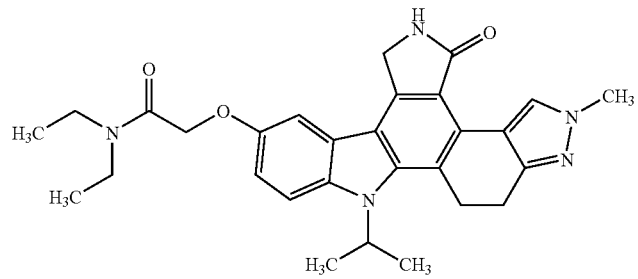 |
| 102 | 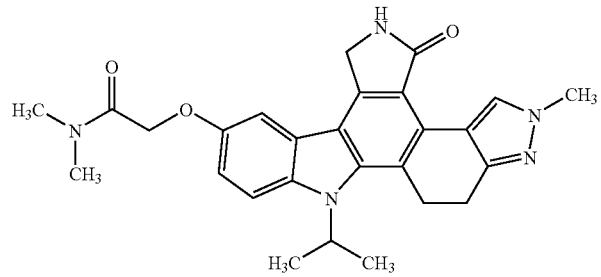 |
| 103 | 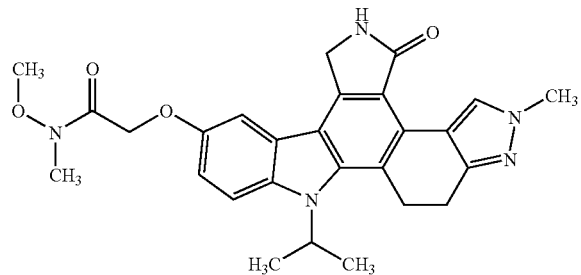 |

-continued
| Example No. | Structure |
|---|---|
| 104 | 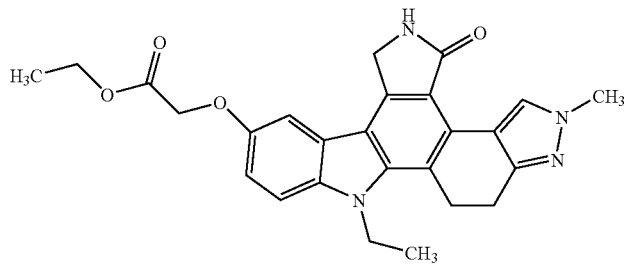 |
| 105 | 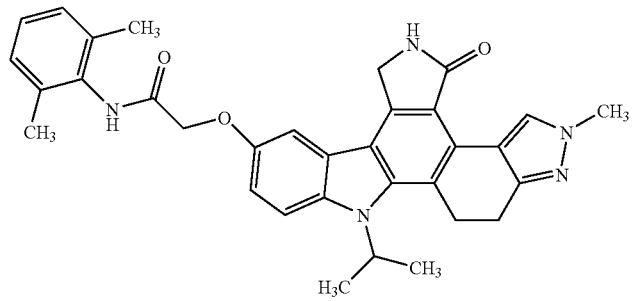 |
| 106 | 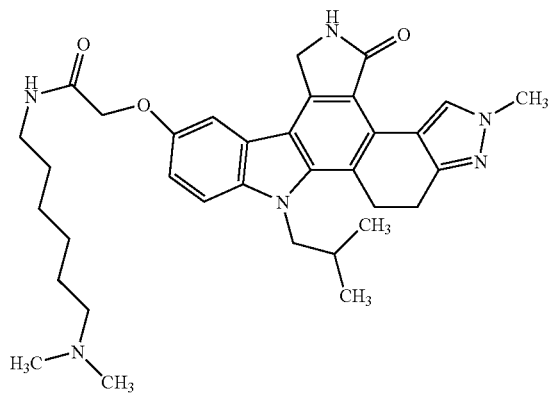 |
| 107 | 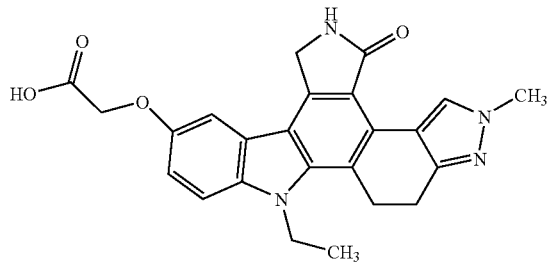 |
| 108 | 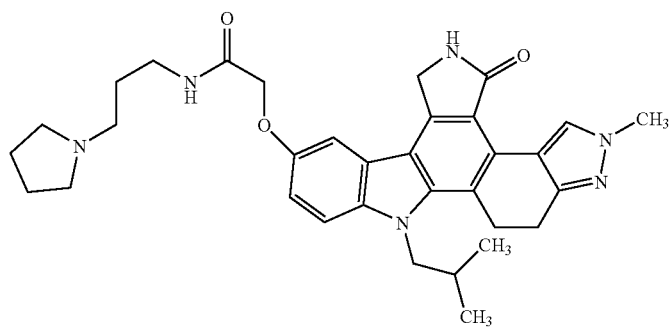 |

US 7,241,779 B2
137                                                                 138
-continued
| Example No. | Structure |
|---|---|
109 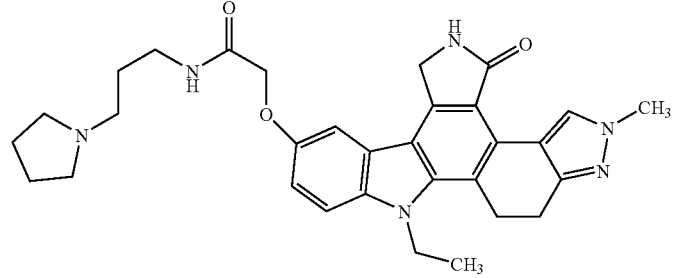
110 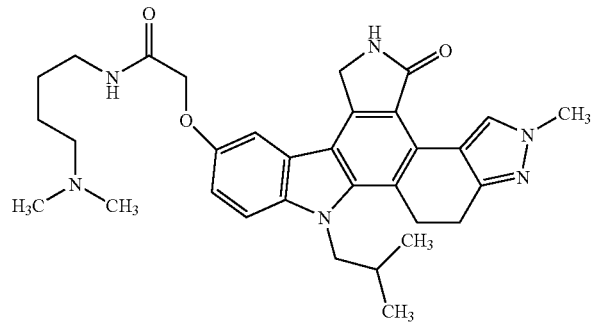
111 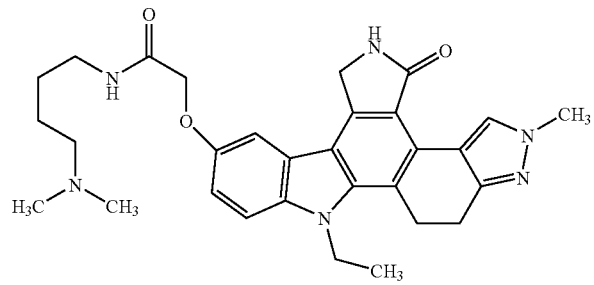
112 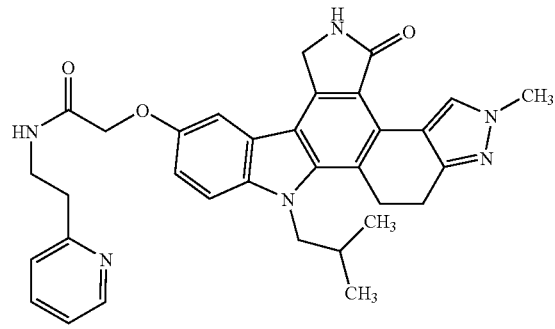

| Example No. | Structure |
|---|---|
| 113 | 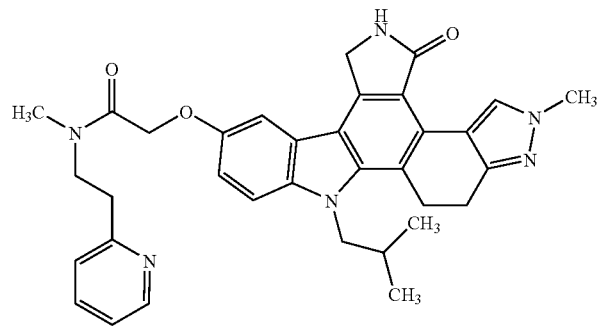 |
| 114 | 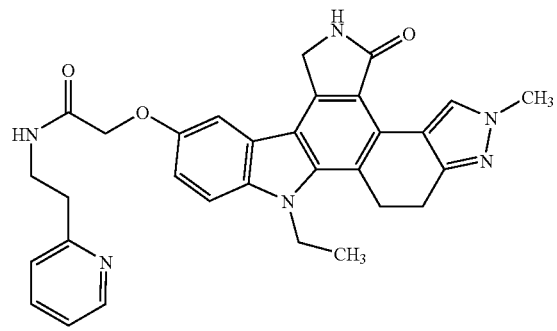 |
| 115 | 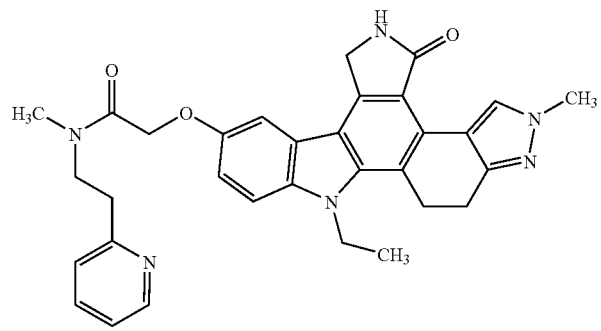 |
| 116 | 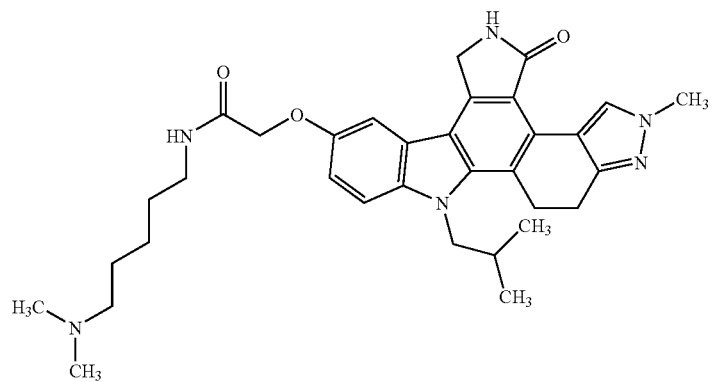 |

| Example No. | Structure |
|---|---|
| 117 | 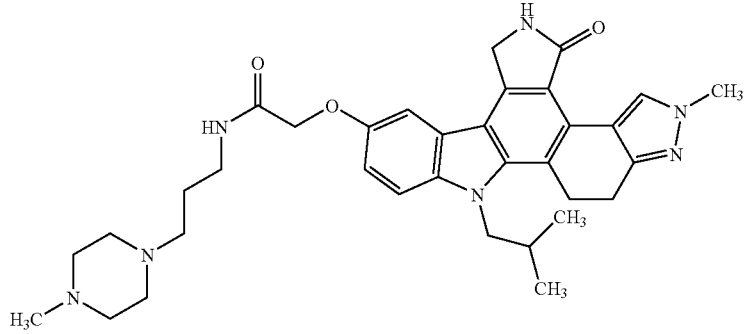 |
| 118 | 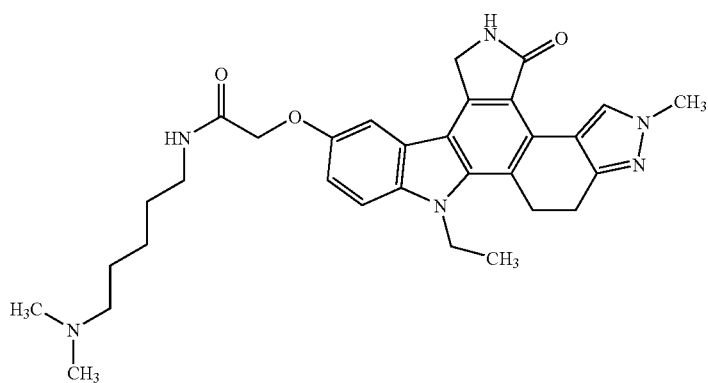 |
| 119 | 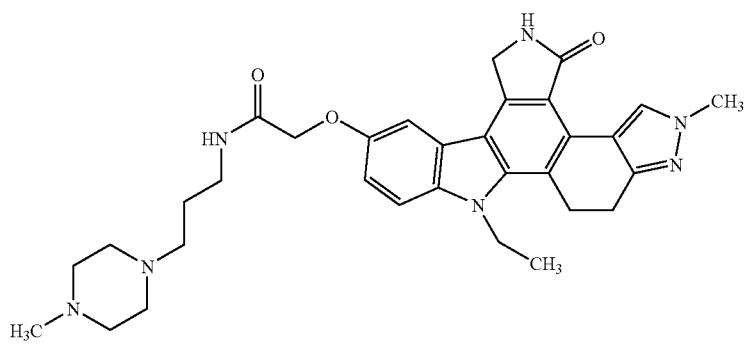 |
| 120 | 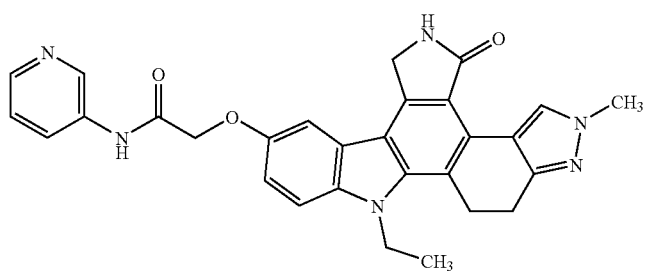 |

| Example No. | Structure |
|---|---|
| 121 | 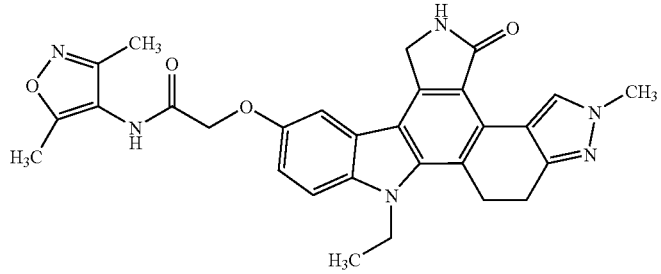 |
| 122 | 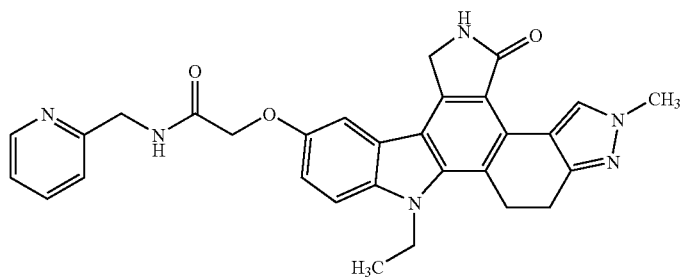 |
| 123 | 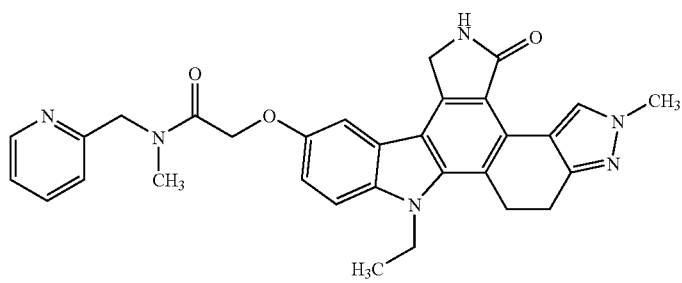 |
| 124 | 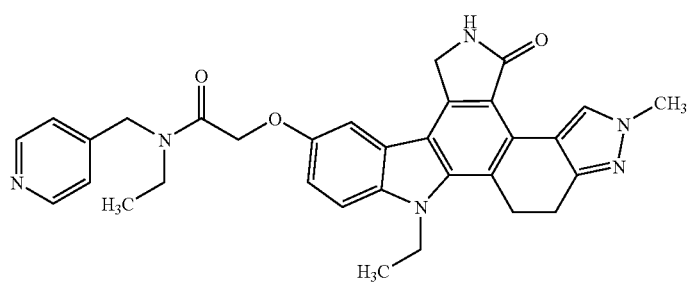 |
| 125 | 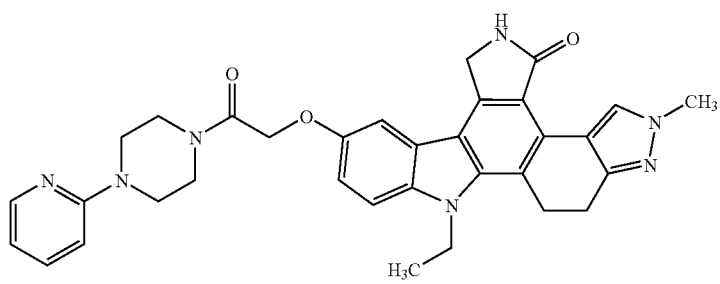 |

-continued
| Example No. | Structure |
|---|---|
| 126 | 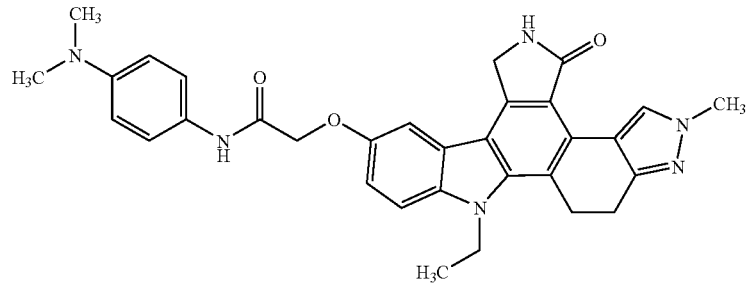 |
| 127 | 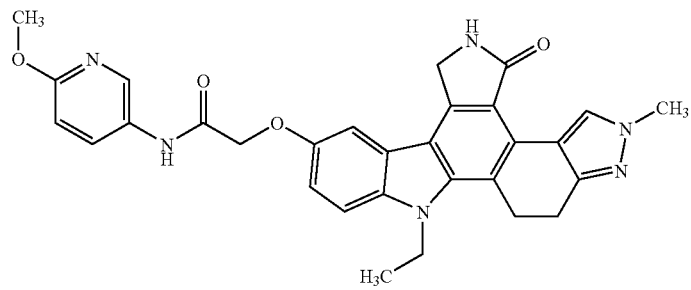 |
| 128 | 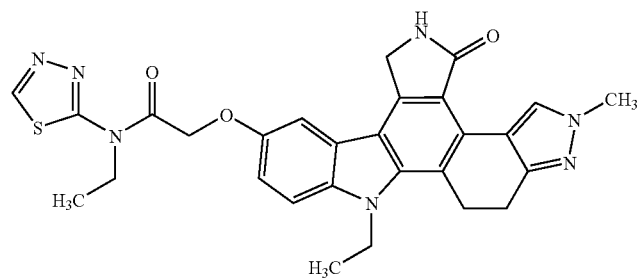 |
| 129 | 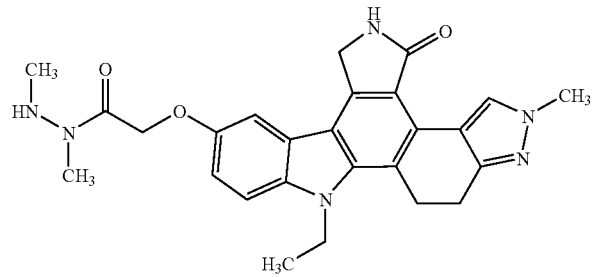 |
| 130 | 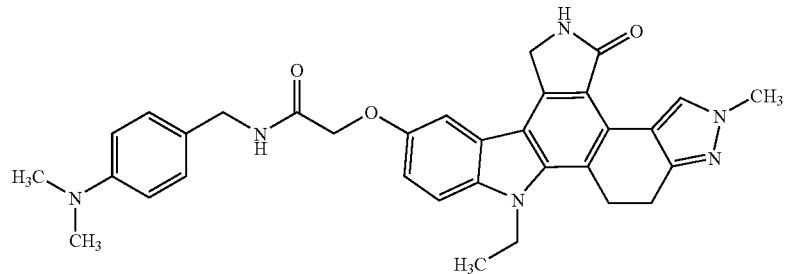 |

| Example No. | Structure |
|---|---|
| 131 | 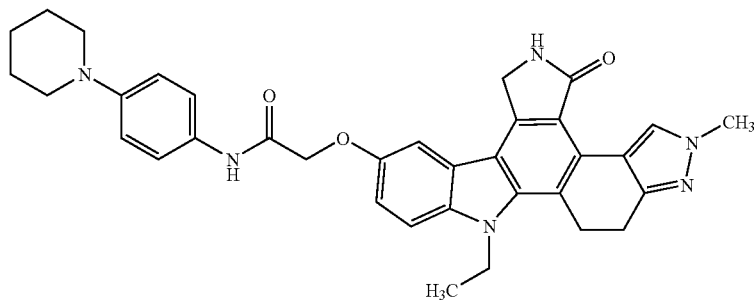 |
| 132 | 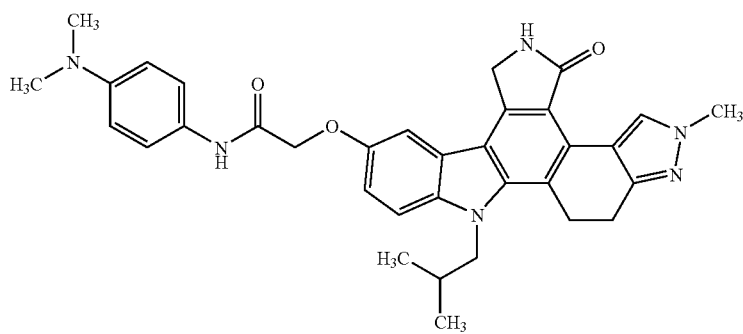 |
| 133 | 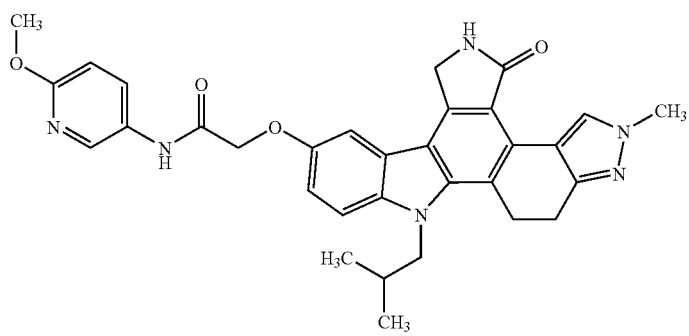 |
| 134 | 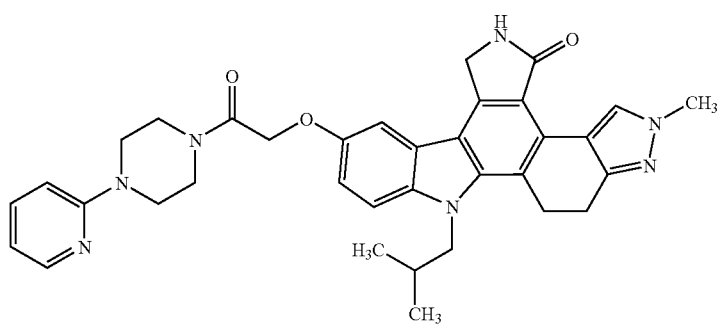 |

-continued
| Example No. | Structure |
|---|---|
| 135 | 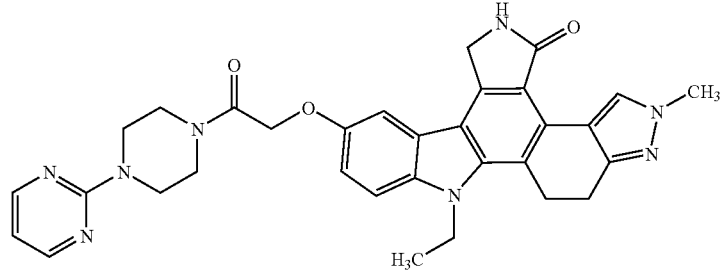 |
| 200 | 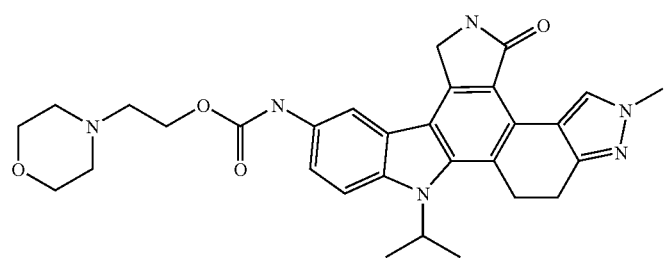 |
| 201 | 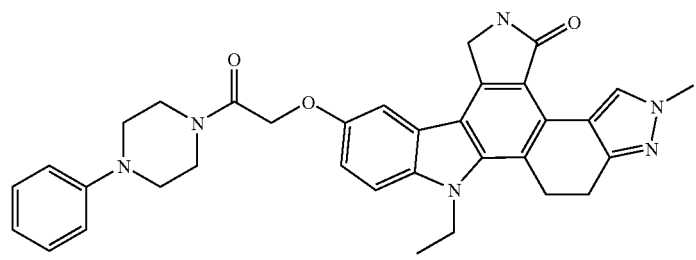 |
| 203 | 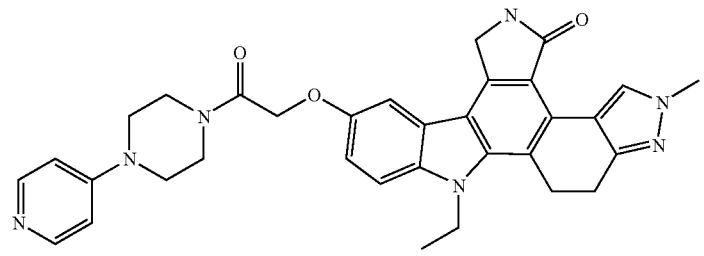 |
| 204 | 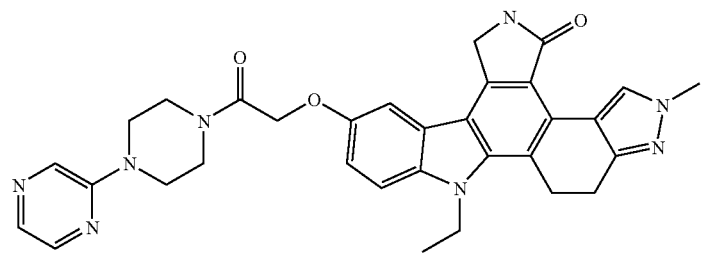 |

| Example No. | Structure |
|---|---|
| 208 | 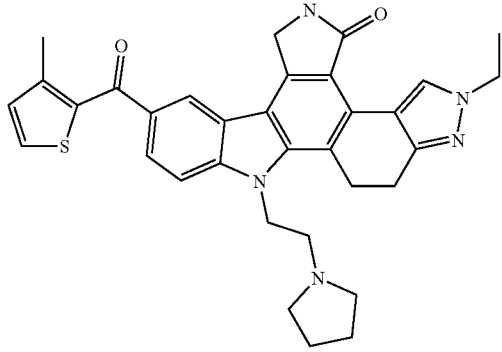 |
| 210 | 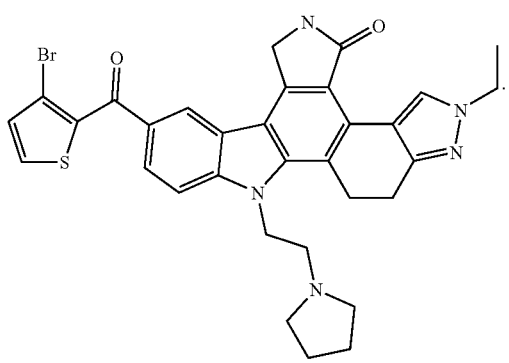 |

19. A pharmaceutical composition comprising a compound of claim 1 and at least one pharmaceutically acceptable excipient.

20. A method for treating solid tumors, comprising administering to a subject in need of such treatment a therapeutically effective amount of a compound of claim 1.

21. A compound selected in accordance with the following table:

| Example No. | Structure |
|---|---|
| 202 | 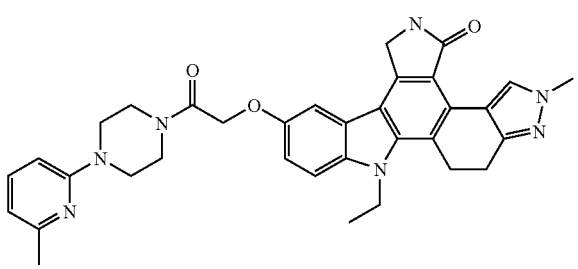 |
| 205 | 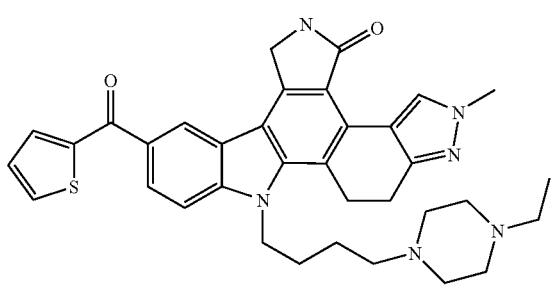 |

-continued
| Example No. | Structure |
|---|---|
| 206 | 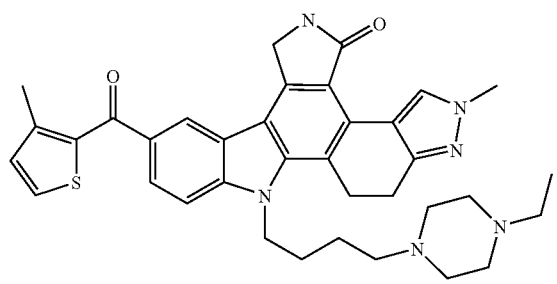 |
| 207 | 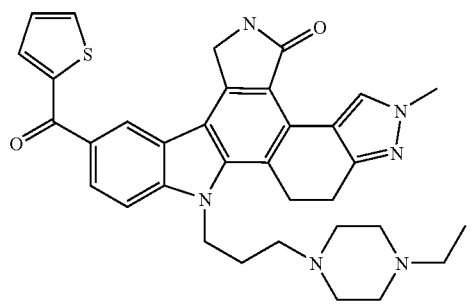 |
| 209 | 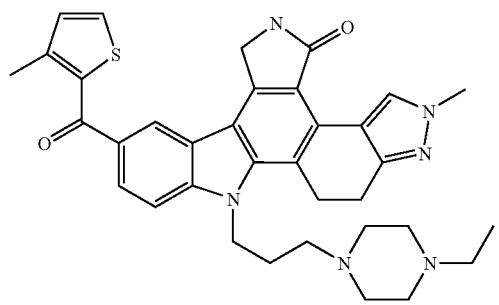 |
| 211 | 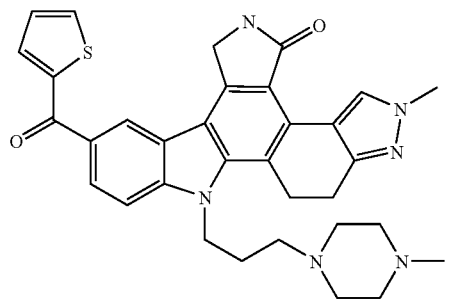 |
| 212 | 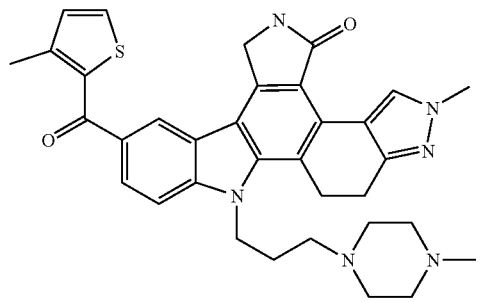 |
* * * * *